(12) United States Patent
von Roemeling et al.

(10) Patent No.: US 12,178,821 B2
(45) Date of Patent: Dec. 31, 2024

(54) COMBINATION THERAPIES FOR THE TREATMENT OF CANCER

(71) Applicant: Curis, Inc., Lexington, MA (US)

(72) Inventors: Reinhard von Roemeling, Ridgefield, CT (US); Andrey Ugolkov, Vernon Hills, IL (US); Robert Martell, Hinesburg, MA (US)

(73) Assignee: Curis, Inc., Lexington, MA (US)

( * ) Notice: Subject to any disclaimer, the term of this patent is extended or adjusted under 35 U.S.C. 154(b) by 0 days.

(21) Appl. No.: 17/680,995

(22) Filed: Feb. 25, 2022

(65) Prior Publication Data

US 2022/0331330 A1 Oct. 20, 2022

Related U.S. Application Data

(60) Provisional application No. 63/172,593, filed on Apr. 8, 2021.

(51) Int. Cl.
| | | |
|---|---|---|
| *A61K 31/5377* | (2006.01) | |
| *A61K 31/5386* | (2006.01) | |
| *A61K 31/7068* | (2006.01) | |
| *A61K 31/7072* | (2006.01) | |
| *A61K 31/7076* | (2006.01) | |
| *A61K 45/06* | (2006.01) | |
| *A61P 35/00* | (2006.01) | |

(52) U.S. Cl.
CPC ...... *A61K 31/5377* (2013.01); *A61K 31/5386* (2013.01); *A61K 31/7068* (2013.01); *A61K 31/7072* (2013.01); *A61K 31/7076* (2013.01); *A61K 45/06* (2013.01); *A61P 35/00* (2018.01)

(58) Field of Classification Search
CPC ................................................. A61K 31/5377
See application file for complete search history.

(56) References Cited

U.S. PATENT DOCUMENTS

| | | | |
|---|---|---|---|
| 5,494,911 | A | 2/1996 | Bartlett et al. |
| 7,338,950 | B2 | 3/2008 | Kelly et al. |
| 9,732,095 | B2 | 8/2017 | Gummadi et al. |
| 9,855,273 | B2 | 1/2018 | Starczynowski et al. |
| 10,047,104 | B2 | 8/2018 | Gummadi et al. |
| 10,160,753 | B2 | 12/2018 | Gummadi et al. |
| 10,640,517 | B2 | 5/2020 | Gummadi et al. |
| 10,758,518 | B2 * | 9/2020 | Booher ............ A61K 31/496 |
| 10,995,100 | B2 | 5/2021 | Gummadi et al. |
| 11,419,875 | B2 | 8/2022 | Gummadi et al. |
| 11,691,987 | B2 | 7/2023 | Gummadi et al. |
| 2005/0192293 | A1 | 9/2005 | Kelly et al. |
| 2006/0014747 | A1 | 1/2006 | Krueger et al. |
| 2006/0160861 | A1 | 7/2006 | Bohlmann et al. |
| 2009/0069288 | A1 | 3/2009 | Breinlinger et al. |
| 2010/0160388 | A1 | 6/2010 | Brotherton-Pleiss et al. |
| 2010/0210619 | A1 | 8/2010 | Bombrun et al. |
| 2011/0224137 | A1 | 9/2011 | Ting et al. |
| 2012/0015962 | A1 | 1/2012 | Arora et al. |
| 2012/0053345 | A1 | 3/2012 | Ericson et al. |
| 2013/0035326 | A1 | 2/2013 | Abraham et al. |
| 2015/0094315 | A1 | 4/2015 | Choi et al. |
| 2016/0326151 | A1 | 11/2016 | Gummadi et al. |
| 2017/0152263 | A1 | 6/2017 | Gummadi et al. |
| 2018/0022758 | A1 | 1/2018 | Gummadi et al. |
| 2018/0201609 | A1 | 7/2018 | Gummadi et al. |
| 2018/0208605 | A1 | 7/2018 | Gummadi et al. |
| 2018/0289685 | A1 | 10/2018 | Bothe et al. |
| 2020/0190112 | A1 | 6/2020 | Gummadi et al. |
| 2021/0290628 | A1 | 9/2021 | Gummadi et al. |
| 2022/0056046 | A1 | 2/2022 | Gummadi et al. |
| 2022/0331330 | A1 | 10/2022 | von Roemeling |
| 2022/0339161 | A1 | 10/2022 | Gummadi et al. |
| 2023/0310444 | A1 | 10/2023 | von Roemeling et al. |
| 2023/0331740 | A1 | 10/2023 | Gummadi et al. |
| 2023/0414582 | A1 | 12/2023 | von Roemeling et al. |

FOREIGN PATENT DOCUMENTS

| | | |
|---|---|---|
| CN | 103608017 A | 2/2014 |
| EP | 1627869 A1 | 2/2006 |
| GB | 2406856 A | 4/2005 |
| JP | 2008-239617 A | 10/2008 |
| KR | 20130128693 A | 11/2013 |
| WO | WO-2004/007457 A2 | 1/2004 |
| WO | WO-2004/007458 A1 | 1/2004 |
| WO | WO-2004/098518 A2 | 11/2004 |
| WO | WO-2004/103954 A1 | 12/2004 |
| WO | WO-2004/108133 A2 | 12/2004 |
| WO | WO-05032493 A2 | 4/2005 |
| WO | WO-2005/0107460 A1 | 11/2005 |
| WO | WO-2006/048249 A1 | 5/2006 |
| WO | WO-2006/053227 A2 | 5/2006 |

(Continued)

OTHER PUBLICATIONS

Pleyer et al., "Azacitidine for Front-Line Therapy of Patients with AML", International Journal of Molecular Sciences, Feb. 15, 2017 (Year: 2017).*

"Relapse and Refractory AML treatments", Blood Cancer UK, Mar. 30, 2020 (Year: 2020).*

Booher et al., "Combination of IRAK4 Inhibitor CA-4948 with BCL2 Inhibitor Venetoclax Induces Tumor Regression in an ABC-DLBCL Xenograft Model", Blood, 130(1): 1534, (2017).

Doonan et al., "CA-4948 for the treatment of melanoma brain metastasis," Central Nervous System Tumors: 1 page (Published Apr. 16, 2022).

International Search Report and Written Opinion for Application No. PCT/US2022/017902 dated Aug. 3, 2022.

(Continued)

*Primary Examiner* — Andrew D Kosar
*Assistant Examiner* — Gillian A Hutter
(74) *Attorney, Agent, or Firm* — Foley Hoag LLP; David P. Halstead; Alexander J. Chatterley

(57) ABSTRACT

The present disclosure relates to methods of treating certain diseases and disorders (e.g., cancer) with a combination of an IRAK4 inhibitor, a BCL-2 inhibitor, and a nucleoside analog.

30 Claims, 2 Drawing Sheets

(56) References Cited

FOREIGN PATENT DOCUMENTS

| | | | |
|---|---|---|---|
| WO | WO-2006/066173 A2 | 6/2006 | |
| WO | WO-2006/066174 A1 | 6/2006 | |
| WO | WO-2006/066795 A1 | 6/2006 | |
| WO | WO-2007/058626 A1 | 5/2007 | |
| WO | WO-2007/095124 A2 | 8/2007 | |
| WO | WO-2007/112914 A2 | 10/2007 | |
| WO | WO-2007/117465 A2 | 10/2007 | |
| WO | WO-2007/121154 A2 | 10/2007 | |
| WO | WO-2008/030579 A2 | 3/2008 | |
| WO | WO-2008/030584 A2 | 3/2008 | |
| WO | WO-2008/061109 A2 | 5/2008 | |
| WO | WO-2008073825 A1 | 6/2008 | |
| WO | WO-2008/156614 A2 | 12/2008 | |
| WO | WO-2009/012312 A1 | 1/2009 | |
| WO | WO-2009/019167 A1 | 2/2009 | |
| WO | WO-2009/102468 A1 | 8/2009 | |
| WO | WO-2010/008847 A2 | 1/2010 | |
| WO | WO-2010/071819 A1 | 6/2010 | |
| WO | WO-2011/046954 A1 | 4/2011 | |
| WO | WO-2011/133750 A1 | 10/2011 | |
| WO | WO-2011/137219 A1 | 11/2011 | |
| WO | WO-2011/163640 A1 | 12/2011 | |
| WO | WO-2012007375 A1 | 1/2012 | |
| WO | WO-2012/068546 A1 | 5/2012 | |
| WO | WO-2012/084704 A1 | 6/2012 | |
| WO | WO-2012/142125 A2 | 10/2012 | |
| WO | WO-2013/042137 A1 | 3/2013 | |
| WO | WO-2013/056070 A2 | 4/2013 | |
| WO | WO-2013/059587 A1 | 4/2013 | |
| WO | WO-2013/068458 A1 | 5/2013 | |
| WO | WO-2014/003483 A1 | 1/2014 | |
| WO | WO-2014/011902 A1 | 1/2014 | |
| WO | WO-2014/070979 A1 | 5/2014 | |
| WO | WO-2014/190163 A2 | 11/2014 | |
| WO | WO-2015/038503 A1 | 3/2015 | |
| WO | WO-2015/091426 A1 | 6/2015 | |
| WO | WO-2015/104662 A1 | 7/2015 | |
| WO | WO-2015/104688 A1 | 7/2015 | |
| WO | WO-2015/119998 A1 | 8/2015 | |
| WO | WO-2015/193846 A1 | 12/2015 | |
| WO | WO-2016/083433 A1 | 6/2016 | |
| WO | WO-2017/009798 A1 | 1/2017 | |
| WO | WO-2017009806 A1 * | 1/2017 | ......... A61K 31/4355 |
| WO | WO-2017/023941 A1 | 2/2017 | |
| WO | WO-2018/081738 A1 | 5/2018 | |
| WO | WO-2018178947 A2 * | 10/2018 | ........... A61K 31/416 |
| WO | WO-2019089580 A1 * | 5/2019 | ........... A61K 31/437 |
| WO | WO-2020/113233 A1 | 6/2020 | |
| WO | WO-2020264499 A1 * | 12/2020 | ......... A61K 31/4545 |
| WO | WO-2022/031330 A1 | 2/2022 | |
| WO | WO-2022/108996 A1 | 5/2022 | |
| WO | WO-2022/216379 A1 | 10/2022 | |
| WO | WO-2023/220227 A1 | 11/2023 | |

OTHER PUBLICATIONS

Issue Notification for U.S. Appl. No. 16/498,866 dated Aug. 3, 2022.
International Preliminary Report on Patentability for Application No. PCT/US2021/059668 dated Feb. 24, 2022.
Iqbal et al., "Preliminary safety and efficacy data on two patients with relapsed/refractory CNS lymphoma treated with emavusertib (CA-4948) and ibrutinib combination: a subset analysis of TakeAim Lymphoma trial," CURIS Presentation: 1 pg (Nov. 17, 2022).
Issue Notice for U.S. Appl. No. 17/245,611 dated Jun. 14, 2023.
Martell., "Discovery and Development of IRAK4 Inhibitor Emavusertib", Curis Presentation: 36 pages (Sep. 29, 2022).
Martell., "Emavusertib," Curis Presentation: 15 pages (Oct. 7, 2022).
Metzeler et al., "ASH Poster #4077: Molecular characterization of clinical response in relapsed/refractory acute myeloid leukemia and high-risk myelodysplastic syndrome patients treated with single agent emavusertib," Pre-ASH Meeting Slideshow, 12 pages (Dec. 1, 2022).
Metzeler et al., "Molecular characterization of clinical response in relapsed/refractory acute myeloid leukemia and high-risk myelodysplastic syndrome patients treated with single agent emavusertib," American Society of Hematology poster, published Nov. 16, 2022 (1 page).
Metzeler et al., "Molecular characterization of clinical response in relapsed/refractory acute myeloid leukemia and high-risk myelodysplastic syndrome patients treated with single agent emavusertib," Curis Inc. Presentation published Nov. 16, 2022 (9 pages).
Von Roemeling et al., "Clinical Activity of IRAK4 Inhibitor, Emavusertib (CA-4948)," Curis Presentation published Oct. 29, 2022 (15 pages).
Zhang, Z. et al. Targeting NF-KB pathway for the therapy of diseases: mechanism and clinical study. Sig Transduct Target Ther 5, 209 (2020).
Bennett et al., "IRAK1 and IRAK4 as emerging therapeutic targets in hematologic malignancies." Current Opinion in Hematology, vol. 29, No. 1, p. 8 (2022).
Booher et al., "Preclinical activity of IRAK4 kinase inhibitor CA-4948 alone or in combination with targeted therapies and preliminary phase 1 clinical results in non-Hodgkin lymphoma." Blood, vol. 132, No. 4168 (2018).
Gao et al., "Inhibition of IL-1 Receptor-Associated Kinase 1 Decreases Murine Acute Graft-versus-Host Disease While Preserving the Graft-versus-Lymphoma Effect." Transplantation and Cellular Therapy, vol. 28, No. 3, pp. 134-e1.(2022).
Gupta et al., "Interleukin-1-receptor kinase 4 inhibition: achieving immunomodulatory synergy to mitigate the impact of COVID-19." Frontiers in Immunology, vol. 12, No. 693085. (2021).
International Search Report and Written Opinion for Application No. PCT/US2023/021812 dated Aug. 6, 2023.
McElroy, "Interleukin-1 receptor-associated kinase 4 (IRAK4) inhibitors: an updated patent review (2016-2018)." Expert opinion on therapeutic patents, vol. 29, No. 4, pp. 243-259.(2019).
Von Roemeling, "IRAK-4 as a therapeutic target in primary CNS lymphoma", University of Florida, Curis, Presentation 28 slides (2022).
Zhang et al "Canonical NF-?B Signalling Is a Potential Target in FLT3/ITD AML." Blood, vol. 120, No. 21, p. 2447 (2012).
Anonymous, "Chronic myelomonocytic leukaemia", Leukaemia Foundation, Retrieved from the Internet: https://www.leukaemia.org.au/blood-cancer/myelodysplastic-syndromes/chronic-myelomonocytic-leukaemia/, pp. 1-2 (2019).
Extended European Search Report for EP Application No. 23173240.5 dated Nov. 11, 2023.
Zhang et al., "Innate immune mediator, Interleukin-1 receptor accessory protein (IL1RAP), is expressed and pro-tumorigenic in pancreatic cancer," Journal of Hematology & Oncology, 15: Article 70 pp. 1-5 (2022).
Curis, "Dec. 2020 Key Opinion Leader Event," (22 pages) (2020).
Dadabayev, "DAKA nVision+ System, Peroxidase," Biocompare, (7 pages) (2004).
Huang et al., "Posttranslational modifications of NF-kappaB: another layer of regulation for NF-kappaB signaling pathway," Cell Signalling, 22(9): 1282-90 (2010).
International Search Report and Written Opinion for International Application No. PCT/US2021/059668 mailed Feb. 24, 2022.
Lange et al., "Preclinical evaluation of a novel interleukin-1 receptor-associated kinase 4 (IRAK4) inhibitor in combination with PI3K inhibitor copanlisib or BTK inhibitors in ABC-DLBCL," Abstract, Cancer Res, 78(13) (5 pages) (2018).
Santa Cruz Biotechnology, "p-NFkB p50 (A-8): sc-271908," (1 page) (2012).
Ugolkov et al., "Identification of NF-kB phospho-p50 as a potential predictive biomarker for IRAK4 inhibitor CA-4948 in patients with Non-Hodgkin's lymphoma," AACR Annual Meeting 2021, Poster No. 385.
Viatour et al., "Phosphorylation of NF-kappaB and IkappaB proteins: implications in cancer and inflammation," Trends Biochem Sci, 30(1): 43-52 (2005).

(56) References Cited

OTHER PUBLICATIONS

Yu et al., "Targeting NF-kB pathway for the therapy of diseases: mechanism and clinical study," Sig Transduct Target Ther, 5(209) (23 pages) (2020).
Rhyasen., "IRAK family kinases as therapeutic targets for Myelodysplastic Syndrome and Acute Myeloid Leukemia" University of Cincinnati: 132 pages (2014).
Abu-Duhier et al., "FLT3 internal tandem duplication mutations in adult acute myeloid leukemia define a high-risk group," British Journal of Haematology, 111: 190-195 (2000).
Alder, C. M. et al., "Identification of a Novel and Selective Series of ltk Inhibitors via a Template-Hopping Strategy", *Med. Chem. Lett.*, 4:948-952 (American Chemical Society, 2013).
Bains et al., "FLT3 and NPM1 Mutations in Myelodysplastic Syndromes: Frequency and Potential Value for Predicting Progression to Acute Myeloid Leukemia," American Journal of Clinical Pathology, 135(1): 62-69 (2011).
Balasubramanian et al., "Abstract 3646: Novel IRAK-4 inhibitors exhibit highly potent anti-proliferative activity in DLBCL cell lines with activating MYD88 L265P mutation," Cancer Research, 75(15 Suppl):Abstract 3646 (2015).
Bhagat et al., "Abstract 2570: IMO-8400, a selective antagonist of TLRs 7, 8 and 9, inhibits MYD88 L265P mutation-driven signaling and cell survival: A potential novel approach for treatment of B-cell lymphomas harboring MYD88 L265P mutation," Cancer Res, 74(19): 2570 (3 pages) (2014).
Booher et al., "Combination of IRAK4 (CA-4948) and BTK (Vecabrutinib) Inhibitors Show Superior Efficacy in Preclinical Models of ABC DLBCL Tumors Containing MYD88-L265P Mutations," Hematological Oncology, 37(S2): 512-512 (2019).
Chen et al., "Design and Synthesis of a Series of Non-Peptide High-Affinity Human Corticotropin-Releasing Factor1 Receptor Antagonists," J Med Chem, 39:4358-4360 (1996).
Chen et al., "Design and synthesis of Imidazo[1,2-b]pyridazine IRAK4 inhibitors for the treatment of mutant MYD88 L265P diffuse large B-cell lymphoma," Eur J Med Chem, 190: 11209 (33 pages) (2020).
Choudhary et al., "Abstract 127: Efficacy of novel IRAK4 inhibitor CA4948 in AML and MDS," Proceedings of the American Association for Cancer Research Annual Meeting 2017; Apr. 1-5, 2017; Washington, DC. Philadelphia (PA): AACR; Cancer Res 2017;77(13 Suppl):Abstract 127 (2017).
Choudhary et al., "SF3B1 Mutations Induce Oncogenetic IRAK4 Isoforms and Activate Targetable Innate Immune Pathways in MDS and AML," Blood, 134(Supplement 1): 4224 (5 pages) (2019).
Clinical study NCT04278768 (V3), "An Open Label Dose Escalation Trial of CA-4948 in Patients With Acute Myelogenous Leukemia or Myelodysplastic Syndrome," Clinical Trials (6 pages) (2020).
Curis Corporate Presentation, NASDAQ:CRIS, Jul. 1, 2020.
Curis Inc. First Quarter 2020 Financial Results, May 12, 2020.
Das et al., "Effects of Positional and Geometrical isomerism on the Biological Activity of Some Novel Oxazolidinones," Bioorg Med Chem Lett, 15:337-343 (2005).
Das et al., "Impact Analysis of SARS-CoV2 on Signaling Pathways During COVID19 Pathogenesis Using Codon Usage Assisted Host-Viral Protein Interactions," BioRxiv, (27 pages) (2020).
Davids et al., "Phase I First-in-Human Study of Venetoclax in Patients With Relapsed or Refractory Non-Hodgkin Lymphoma," J Clin Oncol, 35(8): 826-833 (2015).
Ex Parte Cao, Decision rendered by the Board of Patent Appeals and Interferences in U.S. Appl. No. 10/696,862 on Sep. 21, 2011.
Extended European Search Report for EP Application No. 18777745.3 mailed Jul. 27, 2020.
Extended European Search Report for EP Application No. 18873778.7 dated Jul. 23, 2021.
Extended European Search Report for EP Application No. 20211096.1 dated Feb. 12, 2021.

Extended European Search Report issued by the European Patent Office in corresponding Application No. EP 16823970 issued Jun. 25, 2019.
Extended European Search Report issued by the European Patent Office in corresponding Application No. EP 18190333 issued Mar. 13, 2019.
Extended European Search Report issued by the European Patent Office in corresponding Application No. PCT/IB2015054620 dated Jan. 16, 2018.
Extended European Search Report issued by the European Patent Office in corresponding International Application No. PCT/IB2015/050217, dated May 2, 2017.
Extended European Search Report received for EP Patent Application No. 16823968, mailed Dec. 10, 2018.
Faison, "Curis: Differentiated IRAK4 Inhinitor To Drive Value Creation in the Near Term," Seeking Alpha, Mar. 1, 2021.
Fathi et al., "Treatment of FLT3-ITD acute myeloid leukemia," Am. J. Blood. Res., 1(2): 175-189 (2011).
Garcia-Manero et al., "#2863: A Phase 1, Open Label Dose Escalation Trial Evaluating the Safety, Pharmacokinetics, Pharmacodynamics, and Clinical Activity of Orally Administered CA-4948 in Patients with Acute Myelogenous Leukemia or Myelodysplastic Syndrome," American Society of Hematology, Presentation by Curis Inc. published on Nov. 19, 2020 (10 pages).
Garcia-Manero et al., "A Phase 1, Dose Escalation Trial With Novel Oral IRAK4 Inhibitor CA-4948 In Patients With Acute Myelogenous Leukemia or Myelodysplastic Syndrome—Interim Report," Curis Inc. Presentation published Jun. 11, 2021 (22 pages).
Garcia-Manero., "Spliceosome Mutations, IRAK4 and CA-4948 in MDS and AML," Curis Inc. Presentation published Apr. 24, 2021 (22 pages).
Genung et al., "Chapter Four—Small Molecule Inhibition of Interleukin-1 Receptor-Associated Kinase 4 (IRAK4)," Progress in Medicinal Chemistry, 56: 117-163 (2017).
Gerecitano et al., "A Phase 1 Study of Venetoclax (ABT-199/GDC-0199) Monotherapy in Patients with Relapsed/Refractory Non-Hodgkin Lymphoma," Blood, 126(23):254 (2015).
Golub et al., "Molecular classification of cancer: Class discovery and class prediction by gene expression monitoring," Science, 286: 531-537 (1999).
International Search Report and Written Opinion for International Application No. PCT/IB2016/054203 mailed Sep. 23, 2016.
International Search Report and Written Opinion for International Application No. PCT/IB2016/054229 mailed Nov. 15, 2016.
International Search Report and Written Opinion for International Application No. PCT/US/2018/058194 mailed Feb. 3, 2019.
International Search Report and Written Opinion for International Application No. PCT/US2021/030192 mailed Jun. 25, 2021.
International Search Report from parent PCT application PCT/IB2015/050217 dated Apr. 29, 2015.
International Search Report from parent PCT application PCT/IB2015/054620 dated Oct. 19, 2015.
International Search Report from published parent PCT application PCT/IB2015/050119 dated Mar. 19, 2015.
Kelly et al., "Selective interleukin-1 receptor-associated kinase 4 inhibitors for the treatment of autoimmune disorders and lymphoid malignancy," J Exp Med, 212(13): 2189-2201 (2015).
Knapper et al., "An evaluation of the tyrosine kinase inhibitor pacritinib in patients with relapsed FLT3-mutated acute myeloid leukaemia (the UK NCRI AML17 study)," Haematologica, 101(1): 40 (2016).
Lala at al., "Role of nitric oxide in tumor progression: Lessons from experimental tumors," Cancer and Metastasis Reviews, 17(1):91-106 (1998).
Landgren et al., "MYD88 and beyond: novel opportunities for diagnosis, prognosis and treatment in Waldenström's Macroglobulinemia," Leukemia, 28(9): 1799-1803 (2014).
Lane, "IRAK4 inhibition in AML, MDS and B cell Cancers," Curis Presentation Published Sep. 29, 2021.
Li et al., "Inhibition of IRAK1/4 sensitizes T cell acute lymphoblastic leukemia to chemotherapies," Journal of Clinical Investigation, 125(3): 1081-1097 (2015).

(56) References Cited

OTHER PUBLICATIONS

Li et al., "Synergistic induction of apoptosis in high-risk DLBCL by BCL2 inhibition with ABT-199 combined with pharmacologic loss of MCL1," Leukemia, 29:1702-1712 (2015).
Nowakowski et al., "# 2945: A Multi-Center, Dose-Finding Study to Assess Safety, Tolerability, Pharmacokinetics and Preliminary Efficacy of a novel IRAK4 inhibitor CA-4948 in combination with ibrutinib, in Patients with Relapsed or Refractory Hematologic Malignancies," American Society of Hematology, Presentation by Curis Inc. published on Nov. 19, 2020 (12 pages).
Nowakowski et al., "# 703: Safety, Pharmacokinetics and Activity of CA-4948, an IRAK4 Inhibitor For Treatment of Patients with Relapsed or Refractory Hematologic Malignancies: Results from the Phase 1 Study," American Society of Hematology, Presentation by Curis Inc. published on Nov. 19, 2020 (13 pages).
Partial Search Report and Written Opinion for EP Patent Application No. EP16823970, mailed Mar. 19, 2019.
Rao et al., "Abstract C191: Efficacy of novel IRAK4 inhibitors in ABC-DLBCL and AML models," Proceedings of the AACR-NCI-EORTC International Conference: Molecular Targets and Cancer Therapeutics; Nov. 5-9, 2015; Boston, MA. Philadelphia (PA): AACR; Mol Cancer Ther, 14(12 Suppl 2):Abstract C191 (2015).
Rao Gummadi et al., "Discovery of CA-4948, an Orally Bioavailable IRAK4 Inhibitor for Treatment of Hematologic Malignancies," ACS Medicinal Chemistry Letters: 8 pages (2020).
STN Registry database entry: [online] 2011, CAS RN 1301085-08-4 (Search date: Feb. 9, 2019).
STN Registry database entry: [online] 2011, CAS RN 1421459-19-9 (Search date: Feb. 9, 2019).
STN Registry database entry: [online] 2011, CAS RN 1421491-68-0 (Search date: Feb. 9, 2019).
STN Registry database entry: [online] 2011, CAS RN 1421497-05-3 (Search date: Feb. 9, 2019).
STN Registry database entry: [online] 2014, CAS RN 1178067-91-8 (Search date: Feb. 9, 2019).
STN Registry database entry: [online] 2014, CAS RN 1184469-61-1 (Search date: Feb. 9, 2019).
STN Registry database entry: [online] 2014, CAS RN 1223638-97-8 (Search date: Feb. 9, 2019).
STN Registry database entry: [online] 2014, CAS RN 1252319-44-0 (Search date: Feb. 9, 2019).
STN Registry database entry: [online] 2014, CAS RN 1274105-18-8 (Search date: Feb. 9, 2019).
STN Registry database entry: [online] 2014, CAS RN 1282974-67-7 (Search date: Feb. 9, 2019).
STN Registry database entry: [online] 2014, CAS RN 1333957-90-6 (Search date: Feb. 9, 2019).
STN Registry database entry: [online] 2014, CAS RN 1346410-97-6 (Search date: Feb. 9, 2019).
STN Registry database entry: [online] 2014, CAS RN 1367793-38-1 (Search date: Feb. 9, 2019).
STN Registry database entry: [online] 2014, CAS RN 1368333-88-3 (Search date: Feb. 9, 2019).
STN Registry database entry: [online] 2014, CAS RN 1369195-81-2 (Search date: Feb. 9, 2019).
STN Registry database entry: [online] 2014, CAS RN 1381262-66-3 (Search date: Feb. 9, 2019).
STN Registry database entry: [online] 2014, CAS RN 1381667-74-0 (Search date: Feb. 9, 2019).
STN Registry database entry: [online] 2014, CAS RN 1396710-33-0 (Search date: Feb. 9, 2019).
STN Registry database entry: [online] 2014, CAS RN 1405289-53-3 (Search date: Feb. 9, 2019).
STN Registry database entry: [online] 2014, CAS RN 1414842-47-9 (Search date: Feb. 9, 2019).
STN Registry database entry: [online] 2014, CAS RN 1414842-48-0 (Search date: Feb. 9, 2019).
STN Registry database entry: [online] 2014, CAS RN 1421504-43-9 (Search date: Feb. 9, 2019).
STN Registry database entry: [online] 2014, CAS RN 1421508-39-5 (Search date: Feb. 9, 2019).
STN Registry database entry: [online] 2014, CAS RN 1423498-44-5 (Search date: Feb. 9, 2019).
STN Registry database entry: [online] 2014, CAS RN 1522249-43-9 (Search date: Feb. 9, 2019).
STN Registry database entry: [online] 2014, CAS RN 1548563-20-7 (Search date: Feb. 9, 2019).
STN Registry database entry: [online] 2014, CAS RN 1570255-99-0 (Search date: Feb. 9, 2019).
STN Registry database entry: [online] 2014, CAS RN 1575185-05-5 (Search date: Feb. 9, 2019).
STN Registry database entry: CAS RN 1181327-83-2 (Entered STN: Sep. 8, 2009). (Year: 2009).
STN Registry database entry: CAS RN 1301085-08-4 (Entered STN: May 26, 2011). (Year: 2011).
Sun et al., "Synthesis, in Vitro Evaluation and Cocrystal Structure of 4-Oxo-[1]benzopyrano[4,3-c]pyrazole Cryptosporidium parvum Inosine 5'-Monophosphate Dehydrogenase (CpIMPDH) Inhibitors," J Med Chem, 57:10544-10550 (2014).
Takami et al., "Design and synthesis of Rho kinase inhibitors (I)," Bioorg Med Chem, 12:2115-2137 (2004).
Ugolkov et al., "Identification of NF-kappaB phospho-p50 as a predictive biomarker for IRAK4 inhibitor CA-4948 in patients with Non-Hodgkin's lymphoma," American Associates for Cancer Research, published on Nov. 19, 2020 (1 page).
Von Roemeling et al., "The IRAK4 inhibitor CA-4948 demonstrates antitumor activity in a preclinical model of CNS lymphoma," Molecular Targets and Cancer Therapeutics, Curis Presentation published Oct. 7, 2021 (9 pages).
Wang et al., "Crystal Structures of IRAK-4 Kinase in Complex with Inhibitors: A Serine/Threonine Kinase with Tyrosine as a Gatekeeper," Structure 14, 1835-1844 (2006).
Younes et al., "Phase 1 Dose-Finding Study Investigating CA-4948, an IRAK4 Kinase Inhibitor, in Patients with R/R NHL: Report of Initial Efficacy and Updated Safety Information," Blood, 134(1): 5327 (3 pages) (2019).
Zhang et al., "Design, synthesis and evaluation of bicyclic benzamides as novel 5-HT1F receptor agonists," Bioorg Med Chem Lett, 14(24):6011-6016 (2004).
Blackmon et al., "Test then erase? Current status and future opportunities for Measurable Residual Disease testing in Acute Myeloid Leukemia", Acta Haematologica, pp. 1-14, (2023).
Burguera et al., "Trial in Progress: A Phase 1b Single-Arm, Open-Label Study of Emavusertib (CA-4948) in Combination with Azacitidine and Venetoclax in Acute Myeloid Leukemia Patients in Complete Response with Measurable Residual Disease." Blood 142 (2023): 5975.
Grommes et al., "Emavusertib (CA-4948) in Combination with Ibrutinib in Relapsed/Refractory Primary Central Nervous System Lymphoma (R/R PCNSL) patients." American Society of Clinical Oncology. (2024).
Metzeler et al., "Predictive biomarkers of response to the IRAK4/FLT3 inhibitor emavusertib in hematological malignancies." American Society of Clinical Oncology. (2024).
Winer et al., "Preliminary Safety, Efficacy and Molecular Characterization of Emavusertib (CA-4948) in Relapsed/Refractory (R/R) Acute Myeloid Leukemia (AML) Patients with FLT3 Mutation (FLT3m)" American Society of Clinical Oncology. (2024).

\* cited by examiner

COMBINATION THERAPIES FOR THE TREATMENT OF CANCER

RELATED APPLICATIONS

This application claims the benefit of priority to U.S. Provisional Application No. 63/172,593, filed Apr. 8, 2021; the contents of which are fully incorporated by reference herein.

BACKGROUND

Interleukin-1 (IL-1) Receptor-Associated Kinase 4 (IRAK4) is a serine/threonine kinase enzyme that plays an essential role in signal transduction by Toll/IL-1 receptors (TIRs). Diverse IRAK enzymes are key components in the signal transduction pathways mediated by interleukin-1 receptor (IL-1R) and Toll-like receptors (TLRs) (Janssens, S, et al. Mol. Cell. 11, 2003, 293-302). There are four members in the mammalian IRAK family: IRAK-1, IRAK-2, IRAK-M and IRAK4. These proteins are characterized by a typical N-terminal death domain that mediates interaction with MyD88-family adaptor proteins and a centrally located kinase domain. The IRAK proteins, as well as MyD88, have been shown to play a role in transducing signals other than those originating from IL-1R receptors, including signals triggered by activation of IL-18 receptors (Kanakaraj, et al. J. Exp. Med. 189(7):1999, 1129-38) and LPS receptors (Yang, et al., J. Immunol. 163, 1999, 639-643). Out of four members in the mammalian IRAK family, IRAK4 is considered to be the "master IRAK". Under overexpression conditions, all IRAKs can mediate the activation of nuclear factor-κB (NF-κB) and stress-induced mitogen activated protein kinase (MAPK)-signaling cascades. However, only IRAK-1 and IRAK4 have been shown to have active kinase activity. While IRAK-1 kinase activity could be dispensable for its function in IL-1-induced NF-kB activation (Kanakaraj et al, J. Exp. Med. 187(12), 1998, 2073-2079) and (Xiaoxia Li, et al. Mol. Cell. Biol. 19(7), 1999, 4643-4652), IRAK4 requires its kinase activity for signal transduction (Li S, et al. Proc. Natl. Acad. Sci. USA 99(8), 2002, 5567-5572) and (Lye, E et al, J. Biol. Chem. 279(39); 2004, 40653-8). Given the central role of IRAK4 in Toll-like/IL-1R signalling and immunological protection, IRAK4 inhibitors have been implicated as valuable therapeutics in inflammatory diseases, sepsis and autoimmune disorders (Wietek C, et al, Mol. Interv. 2: 2002, 212-215).

Mice lacking IRAK4 are viable and show complete abrogation of inflammatory cytokine production in response to IL-1, IL-18 or LPS (Suzuki et al. Nature, 416(6882), 2002, 750-756). Similarly, human patients lacking IRAK4 are severely immune-compromised and are not responsive to these cytokines (Medvedev et al. J. Exp. Med., 198(4), 2003, 521-531 and Picard et al. Science 299(5615), 2003, 2076-2079). Knock-in mice containing inactive IRAK4 were completely resistant to lipopolysaccharide- and CpG-induced shock (Kim T W, et al. J Exp Med 204: 2007, 1025-36) and (Kawagoe T, et al. J Exp Med 204(5): 2007, 1013-1024) and illustrated that IRAK4 kinase activity is essential for cytokine production, activation of MAPKs and induction of NF-κB regulated genes in response to TLR ligands (Koziczak-Holbro M, et al. J Biol Chem; 282(18): 2007; 13552-13560). Inactivation of IRAK4 kinase (IRAK4 KI) in mice leads to resistance to EAE due to reduction in infiltrating inflammatory cells into CNS and reduced antigen specific CD4+ T-cell mediated IL-17 production (Kirk A et al. The Journal of Immunology, 183(1), 2009, 568-577).

Non-Hodgkin lymphoma (NHL) is the most common hematologic malignancy in adults with approximately 78 thousand new cases and 20 thousand deaths estimated for 2020 in the United States. The molecular pathology driving NHL is varied, although a common theme is over activity of the NFκB signaling pathway. Specific molecular changes have been identified that drive this pathway is subsets of NHL. For example, Diffuse large B-cell lymphoma (hereafter also referred to as "DLBCL") is an aggressive lymphoma that can arise in lymph nodes or outside of the lymphatic system, in the gastrointestinal tract, testes, thyroid, skin, breast, bone, or brain. DLBCL is a cancer of B cells, a type of white blood cell responsible for producing antibodies. It is the most common type of non-Hodgkin's lymphoma among adults, with an annual incidence of 7-8 cases per 100,000 people per year. This cancer occurs primarily in older individuals, with a median age of diagnosis at approximately 70 years of age, though it can also occur in children and young adults in rare cases. DLBCL is an aggressive tumor and the first sign of this illness is typically the observation of a rapidly growing mass. The five-year survival rate is only 58%. DLBCL has subtypes that are named according to their cell of origin and include germinal center B-cell-like (GCB) and activated B-cell-like (ABC). They differ in having a worse prognosis and, in some cases, requiring particularized approaches to treatment.

Another example of a NHL is Waldenstrom's macroglobulinemia (WM). WM is a non-Hodgkin's lymphoma that affects two types of B cells, lymphoplasmacytoid cells and plasma cells. WM is characterized by having high levels of a circulating antibody, immunoglobulin M (IgM), which is made and secreted by the cells involved in the disease. WM is a rare disease, with only about 1,500 cases per year in the United States. There is no single accepted treatment for WM and a marked variation in clinical outcome due to gaps in knowledge of the disease's molecular basis. Objective response rates are high (>80%) but complete response rates are low (0-15%).

Other types of non-Hodgkin's lymphoma include mantle cell lymphoma (MCL), marginal zone lymphoma (MZL), follicular lymphoma (FL), chronic lymphocytic leukemia (CLL), small lymphocytic lymphoma (SLL), CNS lymphoma, and testicular lymphoma. Non-Hodgkin's lymphoma can be caused by a variety of factors such as infections agents (Epstein-Barr virus, hepatitis C virus and human T-Cell leukemia virus), radiation and chemotherapy treatments, and autoimmune diseases. As a group, non-Hodgkin's lymphoma affects 2.1% of the US population during their life. The percentage of people who survive beyond five years after diagnosis is 71%. In view of the foregoing, there is a clear and unmet need for additional therapies for the treatment of cancers and other diseases associated with IRAK4.

SUMMARY

In one aspect, the present disclosure provides methods of treating cancer in a subject, comprising conjointly administering to the subject an IRAK4 inhibitor or an IRAK4 degrader, a BCL-2 inhibitor, and a nucleoside analog.

In another aspect, the present disclosure provides methods of treating cancer in a subject, comprising conjointly administering to the subject an IRAK4 inhibitor or an IRAK4 degrader and a nucleoside analog.

DETAILED DESCRIPTION

Figure 1A:
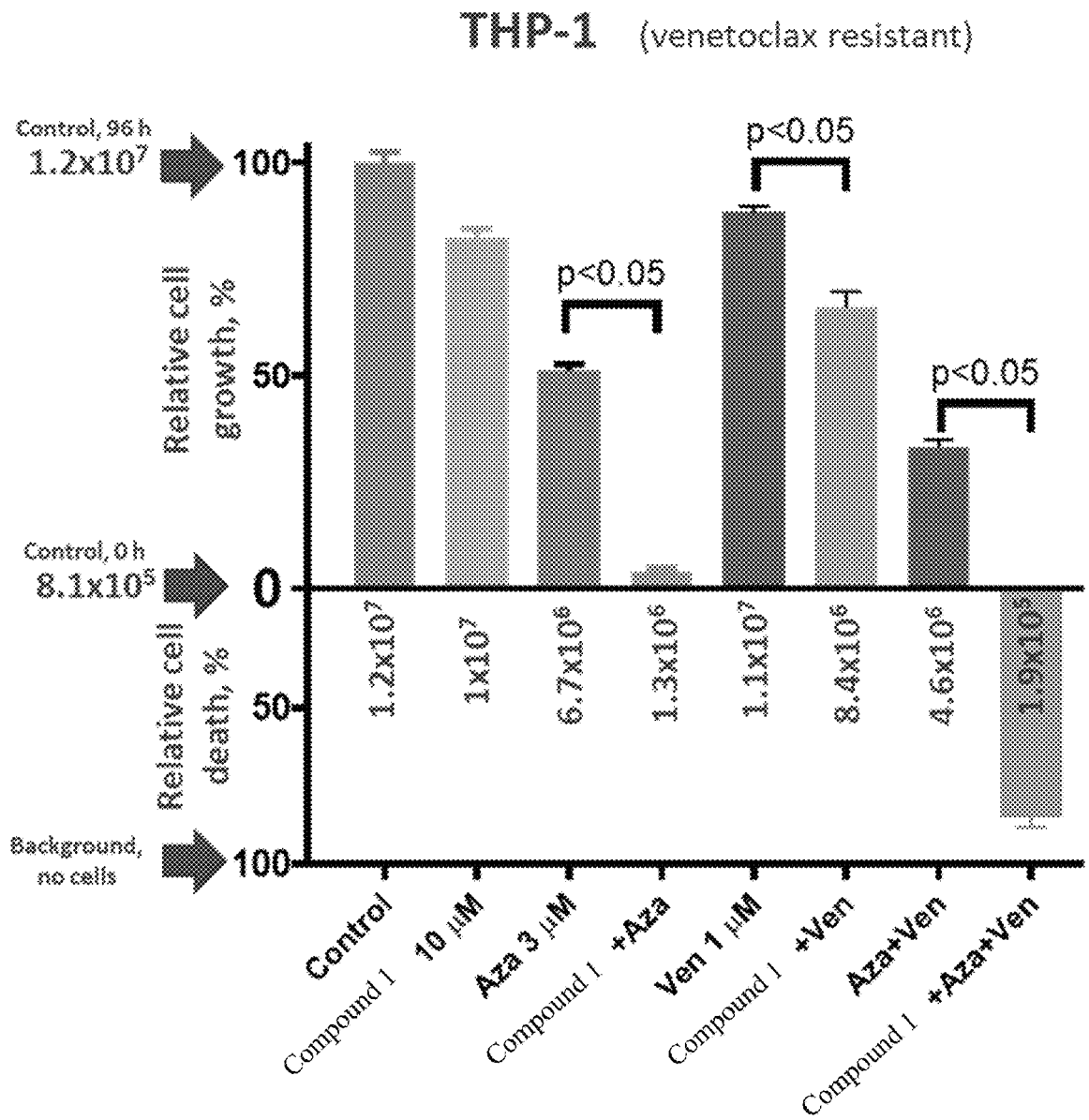
FIG. 1A shows the efficacy of certain therapies in a venetoclax resistant THP-1 cell line. Cells were treated continuously with clinically relevant drug concentration for 96 hrs. Relative cell viability was measured by CellTiter Glo assay (Promega, Madison, WI) at 0 and at 96 hrs according to manufacturer's instructions. All values are presented as mean±SE. Cell viability assay data were analyzed with one-way ANOVA. P values less than 0.05 were considered significant. Statistical analysis was performed using Graph-Pad Prism 8.0 software. The combination of Compound 1, azacitidine, and venetoclax showed synergistic efficacy.
Figure 1B:
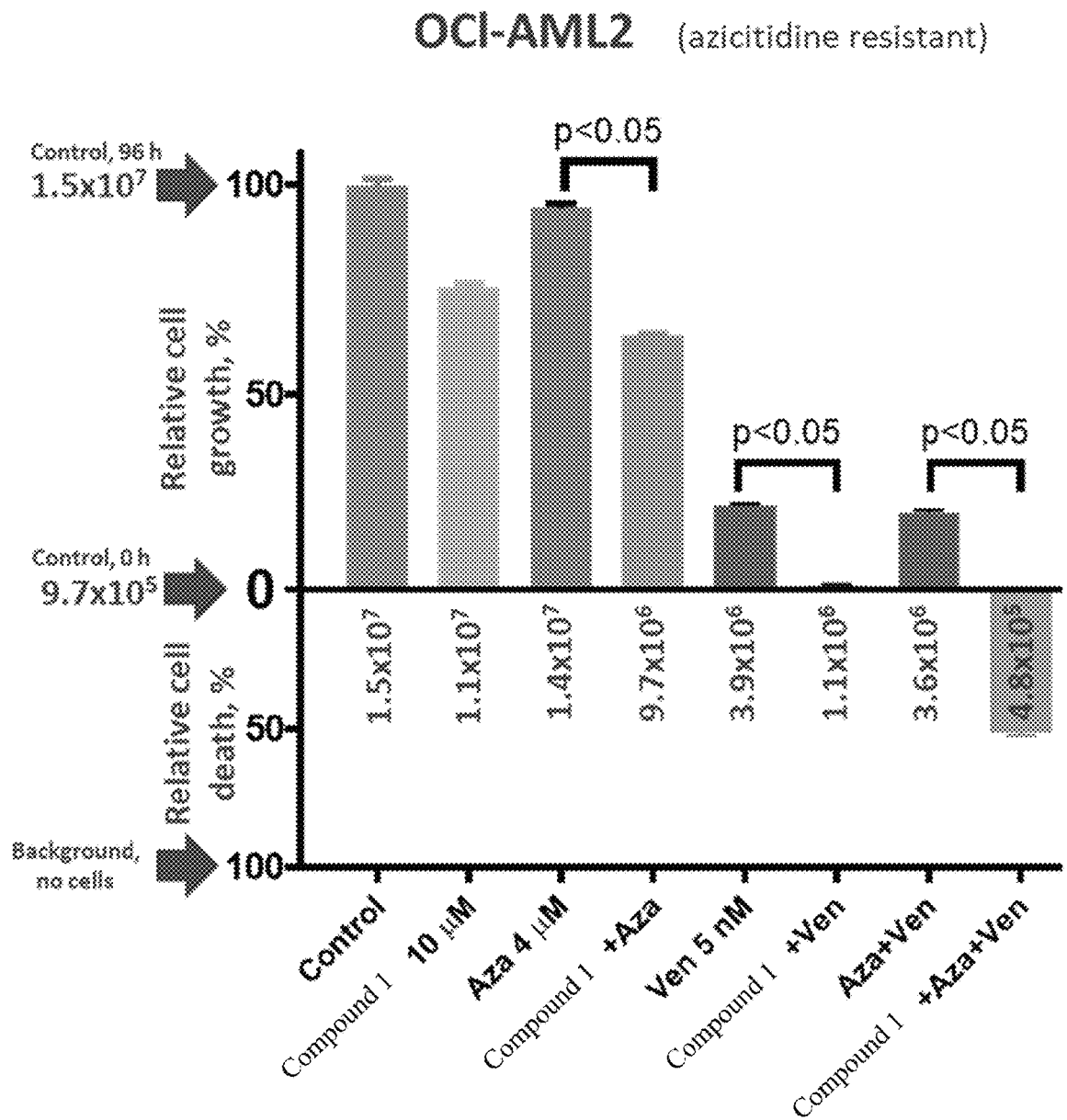
FIG. 1B shows the efficacy of certain therapies in a azacitidine resistant OCI-AML2 cell line. Cells were treated continuously with clinically relevant drug concentration for 96 hrs. Relative cell viability was measured by CellTiter Glo assay (Promega, Madison, WI) at 0 and at 96 hrs according to manufacturer's instructions. All values are presented as mean±SE. Cell viability assay data were analyzed with one-way ANOVA. P values less than 0.05 are considered significant. Statistical analysis was performed using Graph-Pad Prism 8.0 software. The combination of Compound 1, azacitidine, and venetoclax showed synergistic efficacy.

IL-1R associated kinase 4 (IRAK4) is a serine/threonine kinase that is a key component of the myddosome complex. The myddosome, a key component of the innate immune system, transmits intracellular signals from IL-1R and Toll-Like Receptors (TLR), resulting in NFκB activation. This pathway is also oncogenic in a number of malignancies. In greater than 90% of WM cases, a common activating missense mutation in the adapter protein Myeloid Differentiation Primary Response 88 (MYD88), occurs in which leucine is substituted for proline at position 265 (L265P) leading to uncontrolled proliferation. MYD88 is composed of a death domain at the N terminus, an intermediate linker domain, and a Toll/interleukin-1 receptor domain at the C terminus (FIG. 2). Toll-like receptor (TLR) and the inter-leukin 1 family of receptors (IL-1R) signaling occurs through MYD88. MYD88 is involved in the assembly and activation of IL-1R associated kinase 4 (IRAK4) which stimulates NF-κB mediated anti-apoptotic signaling cascades. IL-1R associated kinase 1 (IRAK1) is recruited by MYD88 via direct interaction with IRAK4, the most proximal IRAK. IRAK1 activation ultimately results in formation of the TRAF6-TAK1-IKK (tumor necrosis factor receptor associated factor 6-transforming growth factor beta-activated kinase 1-IkB kinase), activation of the NF-κB pathway, and promotion of cell survival.

Oncogenic signaling is transmitted by the myddosome, which requires IRAK4 for activation. TLRs are widely expressed on tumor cells, regulating growth and other tumor functions. MYD88 is a known oncogene which is mutated in a number of malignancies and requires IRAK4. The long form of IRAK4 (IRAK4-L) is itself known to be oncogenic in AML and MDS, where over half of cases overexpress IRAK4-L. Compound 1 is the first clinical candidate targeting IRAK4 to be evaluated in cancer patients and disclosed herein is evidence that targeting IRAK4 results in anti-cancer activity in a patient.

In one aspect, the present disclosure provides methods of treating cancer in a subject, comprising conjointly administering to the subject an IRAK4 inhibitor or an IRAK4 degrader, a BCL-2 inhibitor, and a nucleoside analog.

In certain preferred embodiments, the methods comprise conjointly administering to the subject an IRAK4 inhibitor, a BCL-2 inhibitor, and a nucleoside analog.

In another aspect, the present disclosure provides methods of treating cancer in a subject, comprising conjointly administering to the subject an IRAK4 inhibitor or an IRAK4 degrader and a nucleoside analog.

In certain preferred embodiments, the methods comprise conjointly administering to the subject an IRAK4 inhibitor and a nucleoside analog.

In certain preferred embodiments, the IRAK4 inhibitor is

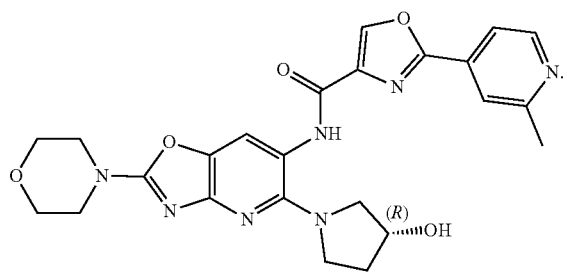

In other preferred embodiments, the IRAK4 inhibitor is

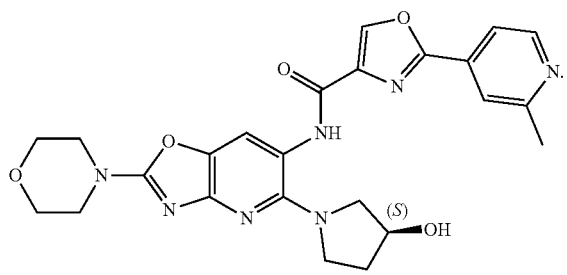

In yet other preferred embodiments, the IRAK4 inhibitor is

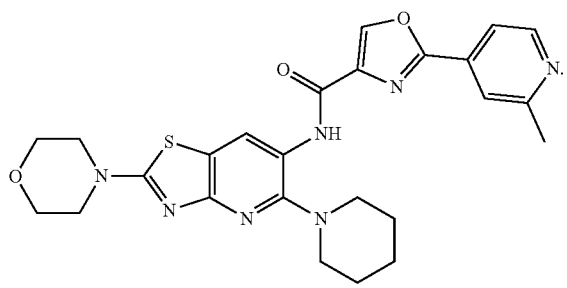 [SMILES: Cc1cc(-c2nc(C(=O)Nc3cc4sc(N5CCOCC5)nc4nc3N3CCCCC3)co2)ccn1]

In yet other preferred embodiments, the IRAK4 inhibitor is

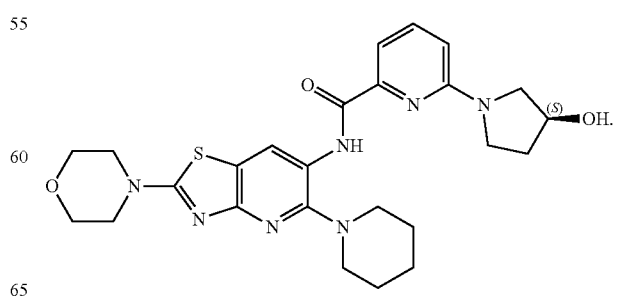

In yet other preferred embodiments, the IRAK4 inhibitor is

[Chemical structure]

In certain preferred embodiments, the BCL-2 inhibitor is venetoclax.

In certain preferred embodiments, the nucleoside analog is azacitidine.

In certain particularly preferred embodiments, the IRAK4 inhibitor is

[Chemical structure]

the BCL-2 inhibitor is venetoclax; and
the nucleoside analog is azacitidine.

In other particularly preferred embodiments, the IRAK4 inhibitor is

[Chemical structure]

and
the nucleoside analog is azacitidine.

IRAK4 Inhibitors of the Disclosure

In certain embodiments, the IRAK4 inhibitor has as structure represented by formula (I) or a pharmaceutically acceptable salt thereof:

[Chemical structure of Formula (1)]

or a pharmaceutically acceptable salt thereof;
wherein
$Z_1$ is an optionally substituted heteroaryl;
$Z_2$ is an optionally substituted heterocycloalkyl, optionally substituted heteroaryl or a direct bond;
$R_1$ is alkyl, cyano, —$NR_aR_b$, or optionally substituted groups selected from cycloalkyl, aryl or heterocyclyl; wherein the substituent, at each occurrence, independently is alkyl, alkoxy, halogen, hydroxyl, hydroxyalkyl, amino, aminoalkyl, nitro, cyano, haloalkyl, haloalkoxy, —OCO—$CH_2$—O-alkyl, —OP(O)(O-alkyl)$_2$ or —$CH_2$—OP(O)(O-alkyl)$_2$;
$R_2$, at each occurrence, independently is an optionally substituted group selected from alkyl or cycloalkyl; wherein the substituent, at each occurrence, is independently halogen, alkoxy, hydroxyl, hydroxyalkyl, haloalkyl or haloalkoxy;
$R_3$, at each occurrence, independently is hydrogen, halogen, alkyl, haloalkyl, haloalkoxy, alkoxy, —$NR_aR_b$, hydroxyl or hydroxyalkyl;
$R_a$ is hydrogen or alkyl;
$R_b$ is hydrogen, alkyl, acyl, hydroxyalkyl, —$SO_2$-alkyl or optionally substituted cycloalkyl; and
'm' and 'n' are independently 1 or 2.

In certain embodiments, $Z_1$ is a 5- or 6-membered optionally substituted heteroaryl.

In certain embodiments, $Z_1$ is an optionally substituted heteroaryl; wherein the optional substituent is alkyl.

In certain embodiments, $Z_1$ is selected from tetrazolyl, thienyl, triazolyl, pyrrolyl, pyridyl, pyranyl, pyrazinyl, pyridazinyl, pyrimidyl, imidazolyl, oxadiazolyl, thiadiazolyl, thiazolyl, isothiazolyl, oxazolyl, furanyl and pyrazolyl.

In certain embodiments, $Z_1$ is selected from pyridyl, oxazolyl and furanyl; wherein the pyridyl group is optionally substituted with alkyl; in particular alkyl is methyl.

In certain embodiments, $Z_2$ is a 5- or 6-membered heteroaryl selected from tetrazolyl, thienyl, triazolyl, pyrrolyl, pyridyl, pyranyl, pyrazinyl, pyridazinyl, pyrimidyl, imidazolyl, oxadiazolyl, thiadiazolyl, thiazolyl, isothiazolyl, oxazolyl, furanyl or pyrazolyl.

In certain embodiments, $Z_2$ is a 5- or 6-membered heterocycloalkyl selected from azetidinyl, oxetanyl, imidazolidinyl, pyrrolidinyl, oxazolidinyl, thiazolidinyl, pyrazolidinyl, tetrahydrofuranyl, piperidinyl, piperazinyl, tetrahydropyranyl, morpholinyl, thiomorpholinyl or 1,4-dioxanyl.

In certain embodiments, $Z_2$ is pyridyl, pyrazolyl or pyrrolidinyl.

In certain embodiments, $Z_2$ is a direct bond.

In certain embodiments, the IRAK4 inhibitor has a structure represented by formula (IA):

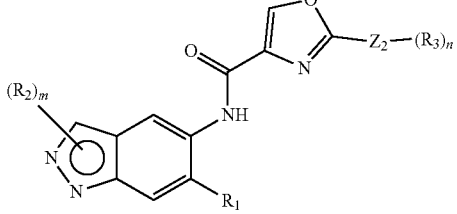

(IA)

or a pharmaceutically acceptable salt thereof.

In certain embodiments, the IRAK4 inhibitor has a structure represented by formula (IB):

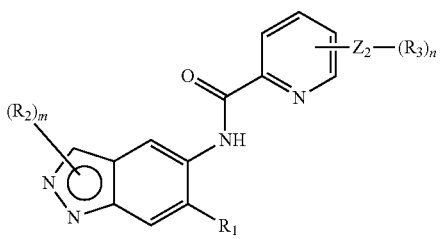

(IB)

or a pharmaceutically acceptable salt thereof.

In certain embodiments, the IRAK4 inhibitor has a structure represented by formula (IC):

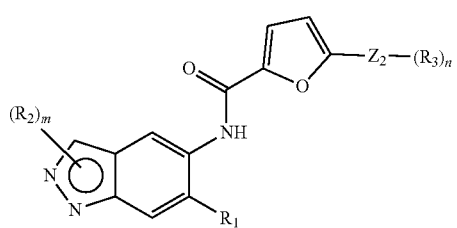

(IC)

or a pharmaceutically acceptable salt thereof.

In certain embodiments,

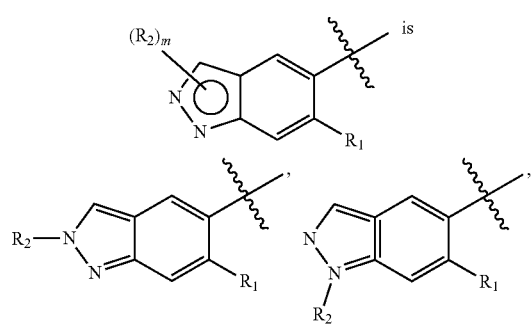 is

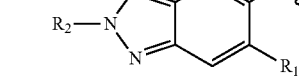

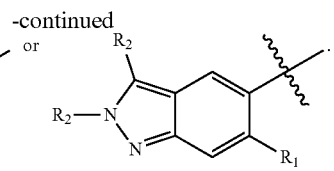

In certain embodiments, $Z_2$ is pyridyl.

In certain embodiments, $Z_2$ is pyrazolyl.

In certain embodiments, $Z_2$ is pyrrolidinyl.

In certain embodiments, $R_1$ is optionally substituted heterocyclyl; wherein the substituent is halogen, hydroxyl, hydroxyalkyl, amino, aminoalkyl, —OCO—CH$_2$—O-alkyl, —OP(O)(O-alkyl)$_2$ or —CH$_2$—OP(O)(O-alkyl)$_2$.

In certain embodiments, $R_1$ is optionally substituted azetidinyl, piperidinyl, morpholinyl, pyrrolidinyl or azepanyl; wherein the substituent is amino, halogen, hydroxyl, hydroxyalkyl, aminoalkyl, —OCO—CH$_2$—O-alkyl, —OP(O)(O-alkyl)$_2$ or —CH$_2$—OP(O)(O-alkyl)$_2$.

In certain embodiments, $R_1$ is optionally substituted piperidinyl; wherein the substituent is hydroxyl.

In certain embodiments, $R_1$ is optionally substituted phenyl; wherein the substituent is halogen.

In certain embodiments, $R_1$ is cycloalkyl.

In certain embodiments, $R_1$ is cyclopropyl or cyclohexyl.

In certain embodiments, $R_1$ is —NR$_a$R$_b$; R$_a$ is hydrogen; R$_b$ is optionally substituted cycloalkyl; wherein the substituent is hydroxyl.

In certain embodiments, $R_1$ is cyano.

In certain embodiments, $R_2$ is optionally substituted alkyl; wherein substituent is alkoxy.

In certain embodiments, $R_2$ is cycloalkyl.

In certain embodiments, $R_3$ is hydrogen, halogen, alkyl, alkoxy, —NR$_a$R$_b$, hydroxyl or hydroxyalkyl; R$_a$ is hydrogen or alkyl; and R$_b$ is hydrogen, alkyl, acyl, hydroxyalkyl or —SO$_2$-alkyl.

In certain embodiments, $Z_1$ is optionally substituted pyridyl; Ring $Z_2$ is pyridyl, pyrazolyl, pyrrolidinyl or direct bond; R$_1$ is an optionally substituted group selected from cyclopropyl, piperidinyl, morpholinyl or pyrrolidinyl; R$_2$ is optionally substituted alkyl or cycloalkyl; R$_3$ is hydrogen, halogen, alkyl, alkoxy, —NR$_a$R$_b$, hydroxyl or hydroxyalkyl; R$_a$ is hydrogen or alkyl; and R$_b$ is hydrogen or hydroxyalkyl.

In certain embodiments, $Z_1$ is oxazolyl; $Z_2$ is pyridyl, pyrazolyl or pyrrolidinyl; R$_1$ is cyano, —NR$_a$R$_b$, or an optionally substituted group selected from cyclopropyl, cyclohexyl, phenyl, azetidinyl, piperidinyl, morpholinyl or pyrrolidinyl; R$_2$ is optionally substituted alkyl or cycloalkyl; R$_3$ is hydrogen, halogen, alkyl, alkoxy, —NR$_a$R$_b$, hydroxyl or hydroxyalkyl; R$_a$ is hydrogen or alkyl; and R$_b$ is hydrogen, alkyl, acyl, hydroxyalkyl, —SO$_2$-alkyl or optionally substituted cycloalkyl.

In certain embodiments, R$_3$ is —NR$_a$R$_b$; R$_a$ is hydrogen or alkyl; and R$_b$ is hydrogen, alkyl, acyl, hydroxyalkyl, —SO$_2$-alkyl or optionally substituted cycloalkyl; wherein the optional substituent is hydroxyl;

In certain embodiments, 'n' is 1.

In certain embodiments, 'n' is 2.

In certain embodiments, 'm' is 1.

In certain embodiments, 'm' is 2.

In certain embodiments, the IRAK4 inhibitor is:

N-(2-methyl-6-(piperidin-1-yl)-2H-indazol-5-yl)-6-(1H-pyrazol-4-yl)picolinamide;
N-(2-methyl-6-(piperidin-1-yl)-2H-indazol-5-yl)-2-(2-methylpyridin-4-yl)oxazole-4-carboxamide;
N-(1-methyl-6-(piperidin-1-yl)-1H-indazol-5-yl)-2-(2-methylpyridin-4-yl)oxazole-4-carboxamide;
N-(2-cyclopentyl-6-(piperidin-1-yl)-2H-indazol-5-yl)-2-(2-methylpyridin-4-yl)oxazole-4-carboxamide;
N-(6-cyano-2-cyclopentyl-2H-indazol-5-yl)-2-(2-methylpyridin-4-yl)oxazole-4-carboxamide;
N-(2-cyclopentyl-6-cyclopropyl-2H-indazol-5-yl)-2-(2-methylpyridin-4-yl)oxazole-4-carboxamide;
N-(2-cyclopentyl-6-cyclopropyl-2H-indazol-5-yl)-6-(1H-pyrazol-4-yl)picolinamide;
N-(2-cyclopentyl-6-morpholino-2H-indazol-5-yl)-2-(2-methylpyridin-4-yl)oxazole-4-carboxamide;
6'-amino-N-(2-cyclopentyl-6-morpholino-2H-indazol-5-yl)-[2,3'-bipyridine]-6-carboxamide2,2,2-trifluoroacetate;
N-(6-(3-fluorophenyl)-2-methyl-2H-indazol-5-yl)-2-(2-methylpyridin-4-yl)oxazole-4-carboxamide;
N-(6-cyclohexyl-2-methyl-2H-indazol-5-yl)-2-(2-methylpyridin-4-yl)oxazole-4-carboxamide hydrochloride;
6'-fluoro-N-(2-methyl-6-(piperidin-1-yl)-2H-indazol-5-yl)-[2,3'-bipyridine]-6-carboxamide hydrochloride;
N-(6-cyclohexyl-2-methyl-2H-indazol-5-yl)-6-(1H-pyrazol-4-yl)picolinamide hydrochloride;
2'-fluoro-N-(2-methyl-6-(piperidin-1-yl)-2H-indazol-5-yl)-[2,3'-bipyridine]-6-carboxamide;
2-(2-chloropyridin-4-yl)-N-(2-methyl-6-(piperidin-1-yl)-2H-indazol-5-yl)oxazole-4-carboxamide hydrochloride;
N-(6-cyclopropyl-2-methyl-2H-indazol-5-yl)-2-(2-methylpyridin-4-yl)oxazole-4-carboxamide hydrochloride;
N-(1-cyclopentyl-6-cyclopropyl-1H-indazol-5-yl)-6-(1-methyl-1H-pyrazol-4-yl)picolinamide;
N-(2-cyclopentyl-6-cyclopropyl-2H-indazol-5-yl)-6-(1-methyl-1H-pyrazol-4-yl)picolinamide;
6-(1-methyl-1H-pyrazol-4-yl)-N-(2-methyl-6-(piperidin-1-yl)-2H-indazol-5-yl)picolinamide;
N-(2-cyclopentyl-6-cyclopropyl-2H-indazol-5-yl)-2-(6-methoxypyridin-3-yl)oxazole-4-carboxamide;
2-(6-methoxypyridin-3-yl)-N-(2-methyl-6-(piperidin-1-yl)-2H-indazol-5-yl)oxazole-4-carboxamide;
N-(2-methyl-6-(piperidin-1-yl)-2H-indazol-5-yl)-2-(3-methylpyridin-4-yl)oxazole-4-carboxamide;
6-bromo-N-(2-methyl-6-(piperidin-1-yl)-2H-indazol-5-yl)picolinamide;
6-chloro-5-methyl-N-(2-methyl-6-(piperidin-1-yl)-2H-indazol-5-yl)picolinamide
N-(2-methyl-6-(piperidin-1-yl)-2H-indazol-5-yl)-2-(6-methylpyridin-3-yl)oxazole-4-carboxamide;
N-(2-cyclopentyl-6-cyclopropyl-2H-indazol-5-yl)-2-(2-methylpyridin-3-yl)oxazole-4-carboxamide;
N-(2-cyclopentyl-6-cyclopropyl-2H-indazol-5-yl)-2-(3-methylpyridin-4-yl)oxazole-4-carboxamide;
N-(2-cyclopentyl-6-cyclopropyl-2H-indazol-5-yl)-2-(6-methylpyridin-3-yl)oxazole-4-carboxamide;
6'-amino-3-methyl-N-(2-methyl-6-(piperidin-1-yl)-2H-indazol-5-yl)-[2,3'-bipyridine]-6-carboxamide hydrochloride;
5-methyl-6-(1-methyl-1H-pyrazol-4-yl)-N-(2-methyl-6-(piperidin-1-yl)-2H-indazol-5-yl)picolinamide;
N-(1-cyclopropyl-6-(piperidin-1-yl)-1H-indazol-5-yl)-2-(2-methylpyridin-4-yl)oxazole-4-carboxamide hydrochloride;
2-(2-hydroxypyridin-3-yl)-N-(2-methyl-6-(piperidin-1-yl)-2H-indazol-5-yl)oxazole-4-carboxamide;
(S)-6-(3-aminopyrrolidin-1-yl)-N-(2-methyl-6-(piperidin-1-yl)-2H-indazol-5-yl)picolinamide 2,2,2-trifluoroacetate;
(S)-6-(1-(2-hydroxypropyl)-1H-pyrazol-4-yl)-N-(2-methyl-6-(piperidin-1-yl)-2H-indazol-5-yl)picolinamide;
N-(1,6-dicyclopropyl-1H-indazol-5-yl)-2-(6-methoxypyridin-3-yl)oxazole-4-carboxamide;
N-(1,6-dicyclopropyl-1H-indazol-5-yl)-2-(2-methylpyridin-4-yl)oxazole-4-carboxamide hydrochloride;
(S)-N-(6-cyclopropyl-1-methyl-1H-indazol-5-yl)-6-(3-hydroxypyrrolidin-1-yl)picolinamide;
(R)-6-(3-hydroxypyrrolidin-1-yl)-N-(2-methyl-6-(piperidin-1-yl)-2H-indazol-5-yl)picolinamide;
(S)-6-(3-hydroxypyrrolidin-1-yl)-N-(2-methyl-6-(piperidin-1-yl)-2H-indazol-5-yl)picolinamide;
6-(3-hydroxypyrrolidin-1-yl)-N-(2-methyl-6-(piperidin-1-yl)-2H-indazol-5-yl)picolinamide;
(S)-6-(3-aminopyrrolidin-1-yl)-N-(6-cyclopropyl-1-methyl-1H-indazol-5-yl)picolinamide;
(R)-6-(3-aminopyrrolidin-1-yl)-N-(2-methyl-6-(piperidin-1-yl)-2H-indazol-5-yl)picolinamide;
(R)-6-(1-(2-hydroxypropyl)-1H-pyrazol-4-yl)-N-(2-methyl-6-(piperidin-1-yl)-2H-indazol-5-yl)picolinamide;
(S)-2-(3-aminopyrrolidin-1-yl)-N-(2-methyl-6-(piperidin-1-yl)-2H-indazol-5-yl)oxazole-4-carboxamide;
N-(6-cyclopropyl-1-methyl-1H-indazol-5-yl)-2-(2-methylpyridin-4-yl)oxazole-4-carboxamide;
(S)-N-(6-cyclopropyl-1-methyl-1H-indazol-5-yl)-6-(1-(2-hydroxypropyl)-1H-pyrazol-4-yl)picolinamide;
(S)-N-(6-cyclopropyl-2-methyl-2H-indazol-5-yl)-6-(1-(2-hydroxypropyl)-1H-pyrazol-4-yl)picolinamide;
(S)-6-(3-aminopyrrolidin-1-yl)-N-(6-cyclopropyl-2-methyl-2H-indazol-5-yl)picolinamide;
(S)-N-(6-cyclopropyl-2-methyl-2H-indazol-5-yl)-6-(3-hydroxypyrrolidin-1-yl)picolinamide;
(S)-N-(6-cyclopropyl-1-methyl-1H-indazol-5-yl)-2-(3-hydroxypyrrolidin-1-yl)oxazole-4-carboxamide;
(S)-2-(3-aminopyrrolidin-1-yl)-N-(6-cyclopropyl-1-methyl-1H-indazol-5-yl)oxazole-4-carboxamide;
(S)-2-(3-hydroxypyrrolidin-1-yl)-N-(2-methyl-6-(piperidin-1-yl)-2H-indazol-5-yl)oxazole-4-carboxamide;
(S)-N-(6-cyclopropyl-1-methyl-1H-indazol-5-yl)-2-(1-(2-hydroxypropyl)-1H-pyrazol-4-yl)oxazole-4-carboxamide;
(S)-2-(3-aminopyrrolidin-1-yl)-N-(6-cyclopropyl-2-methyl-2H-indazol-5-yl)oxazole-4-carboxamide;
(S)-N-(6-cyclopropyl-2-methyl-2H-indazol-5-yl)-2-(3-hydroxypyrrolidin-1-yl)oxazole-4-carboxamide;
(S)-6-(1-(2-hydroxypropyl)-1H-pyrazol-4-yl)-N-(2-methyl-6-(piperidin-1-yl)-2H-indazol-5-yl)picolinamide;
6-((2-hydroxypropyl)amino)-N-(2-methyl-6-(piperidin-1-yl)-2H-indazol-5-yl)picolinamide;
N-(6-(4-hydroxypiperidin-1-yl)-2-methyl-2H-indazol-5-yl)-2-(2-methylpyridin-4-yl)oxazole-4-carboxamide;
N-(6-(azetidin-1-yl)-1-methyl-1H-indazol-5-yl)-2-(2-methylpyridin-4-yl)oxazole-4-carboxamide;
N-(6-(azetidin-1-yl)-2-methyl-2H-indazol-5-yl)-2-(2-methylpyridin-4-yl)oxazole-4-carboxamide;
N-(6-(3-hydroxyazetidin-1-yl)-2-methyl-2H-indazol-5-yl)-2-(2-methylpyridin-4-yl)oxazole-4-carboxamide;
N-(1-methyl-6-(pyrrolidin-1-yl)-1H-indazol-5-yl)-2-(2-methylpyridin-4-yl)oxazole-4-carboxamide;
N-(2-methyl-6-(pyrrolidin-1-yl)-2H-indazol-5-yl)-2-(2-methylpyridin-4-yl)oxazole-4-carboxamide;
(S)-N-(6-(3-hydroxypyrrolidin-1-yl)-2-methyl-2H-indazol-5-yl)-2-(2-methylpyridin-4-yl)oxazole-4-carboxamide;
(R)-N-(6-(3-hydroxypyrrolidin-1-yl)-2-methyl-2H-indazol-5-yl)-2-(2-methylpyridin-4-yl)oxazole-4-carboxamide;
N-(2-methyl-6-(piperidin-1-yl)-2H-indazol-5-yl)-5-(2-methylpyridin-4-yl)furan-2-carboxamide;
N-(6-(4-hydroxypiperidin-1-yl)-2-methyl-2H-indazol-5-yl)-5-(2-methylpyridin-4-yl)furan-2-carboxamide;
N-(6-(3-hydroxypiperidin-1-yl)-2-methyl-2H-indazol-5-yl)-2-(2-methylpyridin-4-yl)oxazole-4-carboxamide;
(R)-N-(6-(3-hydroxypiperidin-1-yl)-2-methyl-2H-indazol-5-yl)-5-(2-methylpyridin-4-yl)furan-2-carboxamide;
N-(6-(3-hydroxypiperidin-1-yl)-2-methyl-2H-indazol-5-yl)-5-(2-methylpyridin-4-yl)furan-2-carboxamide;
N-(6-(azepan-1-yl)-2-methyl-2H-indazol-5-yl)-2-(2-methylpyridin-4-yl)oxazole-4-carboxamide;
N-(6-(azepan-1-yl)-1-methyl-1H-indazol-5-yl)-2-(2-methylpyridin-4-yl)oxazole-4-carboxamide;
N-(2,3-dimethyl-6-(piperidin-1-yl)-2H-indazol-5-yl)-2-(2-methylpyridin-4-yl)oxazole-4-carboxamide;
N-(1,3-dimethyl-6-(piperidin-1-yl)-1H-indazol-5-yl)-2-(2-methylpyridin-4-yl)oxazole-4-carboxamide;
N-(6-(4-hydroxypiperidin-1-yl)-1-(2-methoxyethyl)-1H-indazol-5-yl)-2-(2-methylpyridin-4-yl)oxazole-4-carboxamide;
N-(6-(4-hydroxypiperidin-1-yl)-2-(2-methoxyethyl)-2H-indazol-5-yl)-2-(2-methylpyridin-4-yl)oxazole-4-carboxamide;
N-(6-(4-hydroxypiperidin-1-yl)-1-methyl-1H-indazol-5-yl)-2-(2-methylpyridin-4-yl)oxazole-4-carboxamide;
N-(6-(4-fluoropiperidin-1-yl)-1-methyl-1H-indazol-5-yl)-2-(2-methylpyridin-4-yl)oxazole-4-carboxamide;
N-(6-(3-fluoropiperidin-1-yl)-2-methyl-2H-indazol-5-yl)-2-(2-methylpyridin-4-yl)oxazole-4-carboxamide;

N-(6-(4-(hydroxymethyl)piperidin-1-yl)-2-methyl-2H-indazol-5-yl)-2-(2-methylpyridin-4-yl)oxazole-4-carboxamide;
N-(6-(4-hydroxypiperidin-1-yl)-1,3-dimethyl-1H-indazol-5-yl)-2-(2-methylpyridin-4-yl)oxazole-4-carboxamide;
N-(6-(3-(hydroxymethyl)piperidin-1-yl)-2-methyl-2H-indazol-5-yl)-2-(2-methylpyridin-4-yl)oxazole-4-carboxamide;
N-(6-(4-hydroxypiperidin-1-yl)-2,3-dimethyl-2H-indazol-5-yl)-2-(2-methylpyridin-4-yl)oxazole-4-carboxamide;
2-(2-acetamidopyridin-4-yl)-N-(2-methyl-6-(piperidin-1-yl)-2H-indazol-5-yl)oxazole-4-carboxamide;
2-(2-acetamidopyridin-4-yl)-N-(6-(3-fluoropiperidin-1-yl)-2-methyl-2H-indazol-5-yl)oxazole-4-carboxamide;
2-(2-aminopyridin-4-yl)-N-(2-methyl-6-(piperidin-1-yl)-2H-indazol-5-yl)oxazole-4-carboxamide hydrochloride;
N-(6-(4-fluoropiperidin-1-yl)-1,3-dimethyl-1H-indazol-5-yl)-2-(2-methylpyridin-4-yl)oxazole-4-carboxamide;
N-(6-(((1R,4R)-4-hydroxycyclohexyl)amino)-2-methyl-2H-indazol-5-yl)-2-(2-methylpyridin-4-yl)oxazole-4-carboxamide;
N-(6-(4-(hydroxymethyl)piperidin-1-yl)-1-methyl-1H-indazol-5-yl)-2-(2-methylpyridin-4-yl)oxazole-4-carboxamide;
2-(2-aminopyridin-4-yl)-N-(6-(4-fluoropiperidin-1-yl)-2-methyl-2H-indazol-5-yl)oxazole-4-carboxamide hydrochloride;
N-(6-(4-fluoropiperidin-1-yl)-2-methyl-2H-indazol-5-yl)-2-(2-methylpyridin-4-yl)oxazole-4-carboxamide hydrochloride;
(S)-N-(6-(4-(hydroxymethyl)piperidin-1-yl)-2-methyl-2H-indazol-5-yl)-6-(1-(2-hydroxypropyl)-1H-pyrazol-4-yl)picolinamide;
2-(2-aminopyridin-4-yl)-N-(6-(4-hydroxypiperidin-1-yl)-2-methyl-2H-indazol-5-yl)oxazole-4-carboxamide hydrochloride;
N-(6-(4-(hydroxymethyl)piperidin-1-yl)-1-(2-methoxyethyl)-1H-indazol-5-yl)-2-(2-methylpyridin-4-yl)oxazole-4-carboxamide;
(S)-N-(6-(4-(hydroxymethyl)piperidin-1-yl)-1-methyl-1H-indazol-5-yl)-6-(1-(2-hydroxypropyl)-1H-pyrazol-4-yl)picolinamide;
N-(6-(4-(hydroxymethyl)piperidin-1-yl)-2-(2-methoxyethyl)-2H-indazol-5-yl)-2-(2-methylpyridin-4-yl)oxazole-4-carboxamide;
N-(6-(4-(hydroxymethyl)piperidin-1-yl)-2-methyl-2H-indazol-5-yl)-2-(2-methoxypyridin-4-yl)oxazole-4-carboxamide;
2-(2-acetamidopyridin-4-yl)-N-(6-(4-(hydroxymethyl)piperidin-1-yl)-2-methyl-2H-indazol-5-yl)oxazole-4-carboxamide;
2-(2-aminopyridin-4-yl)-N-(6-(4-(hydroxymethyl)piperidin-1-yl)-1-methyl-1H-indazol-5-yl)oxazole-4-carboxamide hydrochloride;
2-(2-aminopyridin-4-yl)-N-(6-(4-(hydroxymethyl)piperidin-1-yl)-2-methyl-2H-indazol-5-yl)oxazole-4-carboxamide hydrochloride;
N-(6-(4-hydroxypiperidin-1-yl)-1-methyl-1H-indazol-5-yl)-2-(2-methoxypyridin-4-yl)oxazole-4-carboxamide;
2-(2-aminopyridin-4-yl)-N-(6-(3-hydroxypiperidin-1-yl)-2-methyl-2H-indazol-5-yl)oxazole-4-carboxamide hydrochloride;
2-(2-methoxypyridin-4-yl)-N-(2-methyl-6-(piperidin-1-yl)-2H-indazol-5-yl)oxazole-4-carboxamide;
2-(2-aminopyridin-4-yl)-N-(6-(3-fluoropiperidin-1-yl)-2-methyl-2H-indazol-5-yl)oxazole-4-carboxamide hydrochloride;
(R)-2-(2-aminopyridin-4-yl)-N-(6-(3-hydroxypyrrolidin-1-yl)-2-methyl-2H-indazol-5-yl)oxazole-4-carboxamide hydrochloride;
1-(1,3-dimethyl-5-(2-(2-methylpyridin-4-yl)oxazole-4-carboxamido)-1H-indazol-6-yl)piperidin-4-yl 2-methoxyacetate;
N-(6-(4-hydroxypiperidin-1-yl)-2-methyl-2H-indazol-5-yl)-2-(2-methoxypyridin-4-yl)oxazole-4-carboxamide hydrochloride;
N-(6-(4-aminopiperidin-1-yl)-1-(2-methoxyethyl)-1H-indazol-5-yl)-2-(2-methylpyridin-4-yl)oxazole-4-carboxamide hydrochloride;
N-(6-(4-aminopiperidin-1-yl)-2-methyl-2H-indazol-5-yl)-2-(2-methylpyridin-4-yl)oxazole-4-carboxamide hydrochloride;
N-(6-(4-(hydroxymethyl)piperidin-1-yl)-1-(2-methoxyethyl)-3-methyl-1H-indazol-5-yl)-2-(2-methylpyridin-4-yl)oxazole-4-carboxamide;
N-(6-(4-(hydroxymethyl)piperidin-1-yl)-1,3-dimethyl-1H-indazol-5-yl)-2-(2-methylpyridin-4-yl)oxazole-4-carboxamide;
2-(2-aminopyridin-4-yl)-N-(6-(4-(hydroxymethyl)piperidin-1-yl)-1,3-dimethyl-1H-indazol-5-yl)oxazole-4-carboxamide;
N-(6-(4-hydroxypiperidin-1-yl)-1-methyl-1H-indazol-5-yl)-2-(2-hydroxypyridin-4-yl)oxazole-4-carboxamide;
2-(2,6-dimethylpyridin-4-yl)-N-(6-(4-hydroxypiperidin-1-yl)-1-methyl-1H-indazol-5-yl)oxazole-4-carboxamide;
(S)-N-(6-(3-hydroxypyrrolidin-1-yl)-1-methyl-1H-indazol-5-yl)-2-(2-methylpyridin-4-yl)oxazole-4-carboxamide;
N-(6-(4-hydroxypiperidin-1-yl)-1-(2-methoxyethyl)-3-methyl-1H-indazol-5-yl)-2-(2-methylpyridin-4-yl)oxazole-4-carboxamide;
N-(1-(2-hydroxyethyl)-6-(4-hydroxypiperidin-1-yl)-1H-indazol-5-yl)-2-(2-methylpyridin-4-yl)oxazole-4-carboxamide;
N-(6-(4-aminopiperidin-1-yl)-2-(2-methoxyethyl)-2H-indazol-5-yl)-2-(2-methylpyridin-4-yl)oxazole-4-carboxamide hydrochloride;
2-(2,6-dimethylpyridin-4-yl)-N-(2-methyl-6-(piperidin-1-yl)-2H-indazol-5-yl)oxazole-4-carboxamide hydrochloride;
2-(2-(dimethylamino)pyridin-4-yl)-N-(2-methyl-6-(piperidin-1-yl)-2H-indazol-5-yl)oxazole-4-carboxamide;
N-(6-(4-hydroxypiperidin-1-yl)-1-methyl-1H-indazol-5-yl)-2-(2-(methylamino)pyridin-4-yl)oxazole-4-carboxamide;
N-(2-methyl-6-(piperidin-1-yl)-2H-indazol-5-yl)-2-(2-(methylamino)pyridin-4-yl)oxazole-4-carboxamide;
N-(6-(4-hydroxypiperidin-1-yl)-2-methyl-2H-indazol-5-yl)-2-(2-(methylsulfonamido)pyridin-4-yl)oxazole-4-carboxamide;
2-(2-(dimethylamino)pyridin-4-yl)-N-(6-(4-hydroxypiperidin-1-yl)-1-methyl-1H-indazol-5-yl)oxazole-4-carboxamide;
N-(6-(4-(aminomethyl)piperidin-1-yl)-1-(2-methoxyethyl)-1H-indazol-5-yl)-2-(2-methylpyridin-4-yl)oxazole-4-carboxamide;
2-(2,6-dimethylpyridin-4-yl)-N-(6-(4-hydroxypiperidin-1-yl)-2-methyl-2H-indazol-5-yl)oxazole-4-carboxamide;
2-(2,6-dimethylpyridin-4-yl)-N-(6-(4-fluoropiperidin-1-yl)-2-methyl-2H-indazol-5-yl)oxazole-4-carboxamide;
Diethyl (1-(1-methyl-5-(2-(2-methylpyridin-4-yl)oxazole-4-carboxamido)-1H-indazol-6-yl)piperidin-4-yl)phosphate; and
Diethyl ((1-(2-methyl-5-(2-(2-methylpyridin-4-yl)oxazole-4-carboxamido)-2H-indazol-6-yl)piperidin-4-yl)methyl)phosphate;

or a pharmaceutically acceptable salt or a stereoisomer thereof.

In other embodiments, the IRAK4 inhibitor is represented by formula (II):

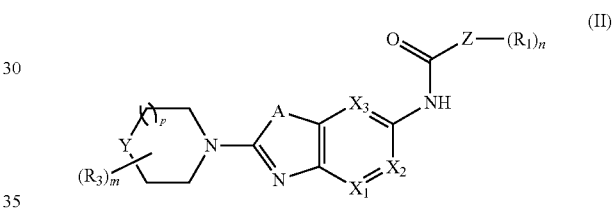

or a pharmaceutically acceptable salt thereof;
wherein,
$X_1$ and $X_3$ independently are CH or N; $X_2$ is $CR_2$ or N; provided one and not more than one of $X_1$, $X_2$ or $X_3$ is N;
A is O or S;
Y is —$CH_2$— or O;
Z is aryl or heterocyclyl;
$R_1$, at each occurrence, is independently halo or optionally substituted heterocyclyl; wherein the substituent is alkyl, alkoxy, aminoalkyl, halo, hydroxyl, hydroxyalkyl or —$NR_aR_b$;
$R_2$ is hydrogen, optionally substituted cycloalkyl, optionally substituted aryl, optionally substituted heterocyclyl or —$NR_aR_b$; wherein the substituent is alkyl, amino, halo or hydroxyl;
$R_3$, at each occurrence, is alkyl or hydroxyl;
$R_a$ and $R_b$ are independently hydrogen, alkyl, acyl or heterocyclyl;
'm' and 'n' are independently 0, 1 or 2; and
'p' is 0 or 1.
In certain embodiments, the moiety

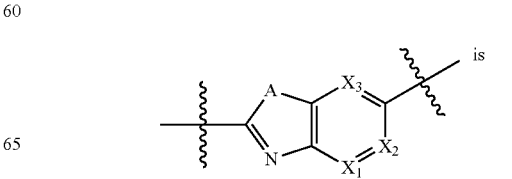

is

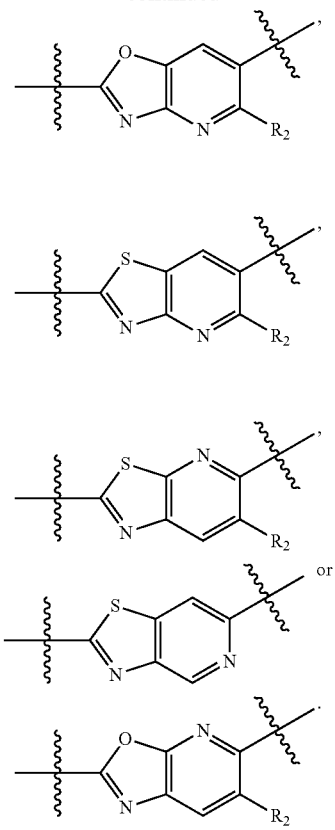

In certain embodiments, Z is aryl or 5- or 6-membered heterocyclyl.

In certain embodiments, Z is phenyl, furanyl, thienyl, pyrrolyl, pyrazolyl, imidazolyl, oxazolyl, isoxazolyl, thiazolyl, isothiazolyl, 1H-tetrazolyl, oxadiazolyl, triazolyl, pyridyl, pyrimidinyl, pyrazinyl, pyridazinyl, oxetanyl, imidazolidinyl, pyrrolidinyl, oxazolidinyl, thiazolidinyl, pyrazolidinyl, tetrahydrofuranyl, piperidinyl, piperazinyl, tetrahydropyranyl, morpholinyl, thiomorpholinyl, 1,4-dioxanyl, dioxidothiomorpholinyl, oxapiperazinyl, oxapiperidinyl, tetrahydrofuryl, tetrahydropyranyl, tetrahydrothiophenyl or dihydropyranyl; each of which is optionally substituted with alkyl, alkoxy, halo, hydroxyl, hydroxyalkyl or —NR$_a$R$_b$; R$_a$ and R$_b$ are independently are hydrogen, alkyl or acyl.

In certain embodiments, Z is phenyl, oxazolyl, furanyl, thienyl or pyridyl; each of which is optionally substituted with one or more R$_1$.

In certain embodiments,

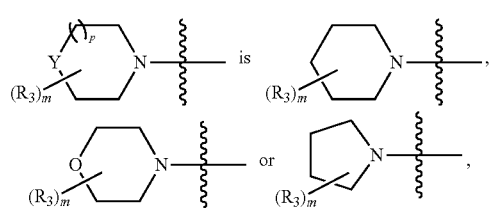

In certain embodiments, the IRAK4 inhibitor has a structure represented by formula (OIA):

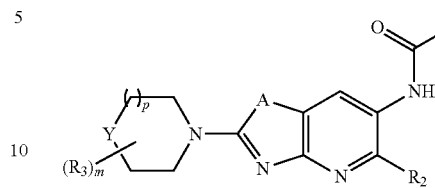

(IIA)

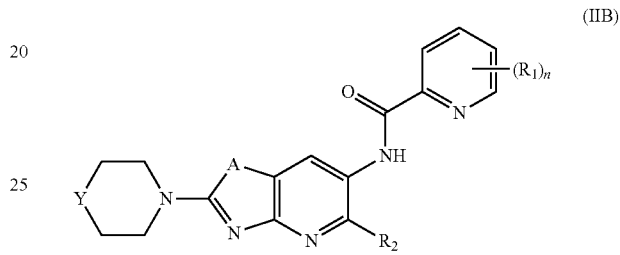

or a pharmaceutically acceptable salt thereof.

In certain embodiments, the IRAK4 inhibitor has a structure represented by formula (IIB):

(IIB)

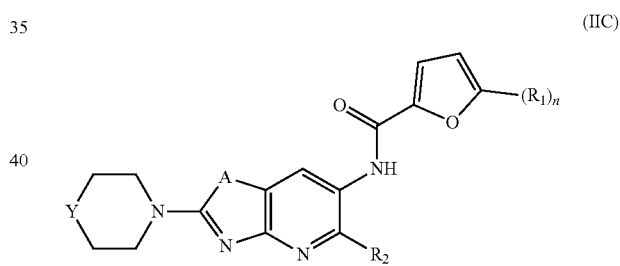

or a pharmaceutically acceptable salt thereof.

In certain embodiments, the IRAK4 inhibitor has a structure represented by formula (IIC):

(IIC)

or a pharmaceutically acceptable salt thereof.

In certain embodiments, Y is O or CH$_2$.

In certain embodiments, R$_1$ is optionally substituted heterocyclyl; wherein the substituent is alkyl, alkoxy, aminoalkyl, halo, hydroxyl, hydroxyalkyl or —NR$_a$R$_b$; R$_a$ and R$_b$ are independently hydrogen, alkyl or acyl.

In certain embodiments, R$_1$ is pyridyl, pyrazolyl, pyrrolidinyl or piperidinyl; each of which is optionally substituted with alkyl, alkoxy, halo, hydroxyl, hydroxyalkyl or —NR$_a$R$_b$; R$_a$ and R$_b$ are independently hydrogen or acyl.

In certain embodiments, R$_2$ is hydrogen.

In certain embodiments, R$_2$ is optionally substituted cycloalkyl.

In certain embodiments, R$_2$ is cyclopropyl.

In certain embodiments, R$_2$ is optionally substituted heterocyclyl; wherein the substituent is alkyl, amino, halo or hydroxyl.

In certain embodiments, R$_2$ is piperidinyl, pyrrolidinyl, morpholinyl, piperazinyl, azetidinyl, pyrazolyl, furanyl, pyridyl, azepanyl or azabicyclo[3.2.1]octanyl; wherein the substituent is alkyl, amino, halo or hydroxyl.

In certain embodiments, $R_2$ is optionally substituted aryl; wherein the substituent is halo.

In certain embodiments, $R_2$ is optionally substituted phenyl; wherein the substituent is fluoro.

In certain embodiments, $R_2$ is —$NR_aR_b$; wherein $R_a$ and $R_b$ are independently hydrogen or heterocyclyl.

In certain embodiments, $R_2$ is —$NR_aR_b$; wherein $R_a$ and $R_b$ are independently hydrogen or pyrrolidinyl.

In certain embodiments, A is O or S; Y is —$CH_2$— or O; $R_1$ is halo, pyridyl, pyrazolyl, pyrrolidinyl each of which is optionally substituted with alkyl, alkoxy, halo, hydroxyl, hydroxyalkyl or —$NR_aR_b$; $R_2$ is hydrogen, optionally substituted cycloalkyl, optionally substituted aryl, optionally substituted heterocyclyl or —$NR_aR_b$; wherein the substituent is alkyl, amino, halo or hydroxyl; $R_a$ and $R_b$ are independently hydrogen or alkyl.

In certain embodiments, A is O or S; Y is —$CH_2$— or O; $R_1$ is pyridyl, pyrazolyl, pyrrolidinyl; each of which is optionally substituted with alkyl, hydroxyl, hydroxyalkyl or —$NR_aR_b$; $R_a$ and $R_b$ are independently hydrogen; $R_2$ is hydrogen, optionally substituted cycloalkyl, optionally substituted aryl, optionally substituted heterocyclyl or —$NR_aR_b$; wherein the substituent is alkyl, amino, halo or hydroxyl; $R_a$ and $R_b$ are independently hydrogen, alkyl, acyl or heterocyclyl.

In certain embodiments, 'n' is 0, 1 or 2.

In certain embodiments, 'p' is 0 or 1.

In certain embodiments, 'm' is 0 or 2.

In certain embodiments, the IRAK4 inhibitor is selected from:

6'-amino-N-(2-morpholinooxazolo[4,5-b]pyridin-6-yl)-[2,3'-bipyridine]-6-carboxamide;
6'-amino-N-(5-cyclopropyl-2-morpholinooxazolo[4,5-b]pyridin-6-yl)-[2,3'-bipyridine]-6-carboxamide hydrochloride;
N-(5-cyclopropyl-2-morpholinooxazolo[4,5-b]pyridin-6-yl)-2-(2-methylpyridin-4-yl)oxazole-4-carboxamide hydrochloride;
N-(2,5-di(piperidin-1-yl)oxazolo[4,5-b]pyridin-6-yl)-6-(1H-pyrazol-4-yl)picolinamide hydrochloride;
N-(2,5-di(piperidin-1-yl)oxazolo[4,5-b]pyridin-6-yl)-2-(2-methylpyridin-4-yl)oxazole-4-carboxamide;
N-(2-morpholino-5-(piperidin-1-yl)oxazolo[4,5-b]pyridin-6-yl)-6-(1H-pyrazol-4-yl)picolinamide;
2-(2-methylpyridin-4-yl)-N-(2-morpholino-5-(piperidin-1-yl)oxazolo[4,5-b]pyridin-6-yl)oxazole-4-carboxamide;
6-chloro-N-(2-morpholino-5-(piperidin-1-yl)oxazolo[4,5-b]pyridin-6-yl)picolinamide;
N-(2,5-di(piperidin-1-yl)oxazolo[4,5-b]pyridin-6-yl)-6-(1-methyl-1H-pyrazol-4-yl)picolinamide;
2-(2-chloropyridin-4-yl)-N-(2,5-di(piperidin-1-yl)oxazolo[4,5-b]pyridin-6-yl)oxazole-4-carboxamide;
(S)-2-(2-methylpyridin-4-yl)-N-(2-morpholino-5-(pyrrolidin-3-ylamino)oxazolo[4,5-b]pyridin-6-yl)oxazole-4-carboxamide;
6'-amino-N-(2-morpholinooxazolo[5,4-b]pyridin-5-yl)-[2,3'-bipyridine]-6-carboxamide;
6'-amino-N-(2-morpholinothiazolo[4,5-c]pyridin-6-yl)-[2,3'-bipyridine]-6-carboxamide;
6'-amino-N-(2-morpholinothiazolo[5,4-b]pyridin-5-yl)-[2,3'-bipyridine]-6-carboxamide;
2-(2-methylpyridin-4-yl)-N-(2-morpholinothiazolo[4,5-b]pyridin-6-yl)oxazole-4-carboxamide;
6'-amino-N-(2-morpholinothiazolo[4,5-b]pyridin-6-yl)-[2,3'-bipyridine]-6-carboxamide;
N-(2-morpholinothiazolo[4,5-b]pyridin-6-yl)-6-(1H-pyrazol-4-yl)picolinamide;
3-(4-(aminomethyl)piperidin-1-yl)-5-fluoro-N-(2-morpholinothiazolo[4,5-b]pyridin-6-yl)benzamide;
2-(4-(aminomethyl)piperidin-1-yl)-5-fluoro-N-(2-morpholinothiazolo[4,5-b]pyridin-6-yl)benzamide;
2-(2-methylpyridin-4-yl)-N-(2-morpholino-5-(piperidin-1-yl)thiazolo[4,5-b]pyridin-6-yl)oxazole-4-carboxamide;
N-(2-morpholino-5-(piperidin-1-yl)thiazolo[4,5-b]pyridin-6-yl)-6-(1H-pyrazol-4-yl)picolinamide;
N-(2,5-di(piperidin-1-yl)thiazolo[4,5-b]pyridin-6-yl)-6-(1H-pyrazol-4-yl)picolinamide;
N-(2,5-di(piperidin-1-yl)thiazolo[4,5-b]pyridin-6-yl)-2-(2-methylpyridin-4-yl)oxazole-4-carboxamide;
N-(2,5-dimorpholinooxazolo[4,5-b]pyridin-6-yl)-2-(2-methylpyridin-4-yl)oxazole-4-carboxamide;
N-(5-(4-methylpiperazin-1-yl)-2-morpholinooxazolo[4,5-b]pyridin-6-yl)-2-(2-methylpyridin-4-yl)oxazole-4-carboxamide;
N-(2,5-di(piperidin-1-yl)oxazolo[4,5-b]pyridin-6-yl)-2-(6-methoxypyridin-3-yl)oxazole-4-carboxamide;
N-(2,5-di(piperidin-1-yl)oxazolo[4,5-b]pyridin-6-yl)-2-(2-methylpyridin-3-yl)oxazole-4-carboxamide;
N-(2,5-di(piperidin-1-yl)oxazolo[4,5-b]pyridin-6-yl)-2-(2-hydroxypyridin-3-yl)oxazole-4-carboxamide;
2-(2-hydroxypyridin-3-yl)-N-(2-morpholino-5-(piperidin-1-yl)oxazolo[4,5-b]pyridin-6-yl)oxazole-4-carboxamide;
N-(2,5-di(piperidin-1-yl)oxazolo[4,5-b]pyridin-6-yl)-2-(6-hydroxypyridin-3-yl)oxazole-4-carboxamide;

2-(2-methoxypyridin-4-yl)-N-(2-morpholino-5-(piperidin-1-yl)oxazolo[4,5-b]pyridin-6-yl)oxazole-4-carboxamide;
2-(2-methylpyridin-3-yl)-N-(2-morpholino-5-(piperidin-1-yl)oxazolo[4,5-b]pyridin-6-yl)oxazole-4-carboxamide;
2-(3-methylpyridin-4-yl)-N-(2-morpholino-5-(piperidin-1-yl)oxazolo[4,5-b]pyridin-6-yl)oxazole-4-carboxamide;
N-(2,5-di(piperidin-1-yl)oxazolo[4,5-b]pyridin-6-yl)-2-(3-methylpyridin-4-yl)oxazole-4-carboxamide;
2-(6-methylpyridin-3-yl)-N-(2-morpholino-5-(piperidin-1-yl)oxazolo[4,5-b]pyridin-6-yl)oxazole-4-carboxamide;
6-(1-methyl-1H-pyrazol-4-yl)-N-(2-morpholino-5-(piperidin-1-yl)oxazolo[4,5-b]pyridin-6-yl)picolinamide;
N-(2,5-di(piperidin-1-yl)oxazolo[4,5-b]pyridin-6-yl)-2-(6-methylpyridin-3-yl)oxazole-4-carboxamide;
(S)-N-(5-(3-aminopyrrolidin-1-yl)-2-morpholinooxazolo[4,5-b]pyridin-6-yl)-2-(2-methylpyridin-4-yl)oxazole-4-carboxamide;
(S)-N-(5-(3-hydroxypyrrolidin-1-yl)-2-morpholinooxazolo[4,5-b]pyridin-6-yl)-2-(2-methylpyridin-4-yl)oxazole-4-carboxamide;
(R)-N-(5-(3-aminopyrrolidin-1-yl)-2-morpholinooxazolo[4,5-b]pyridin-6-yl)-2-(2-methylpyridin-4-yl)oxazole-4-carboxamide;
(R)-N-(5-(3-hydroxypyrrolidin-1-yl)-2-morpholinooxazolo[4,5-b]pyridin-6-yl)-2-(2-methylpyridin-4-yl)oxazole-4-carboxamide;
(S)-2-(3-aminopyrrolidin-1-yl)-N-(2-morpholino-5-(piperidin-1-yl)oxazolo[4,5-b]pyridin-6-yl)oxazole-4-carboxamide;
(S)-6-(3-hydroxypyrrolidin-1-yl)-N-(2-morpholino-5-(piperidin-1-yl)oxazolo[4,5-b]pyridin-6-yl)picolinamide;
(S)-6-(3-aminopyrrolidin-1-yl)-N-(2-morpholino-5-(piperidin-1-yl)oxazolo[4,5-b]pyridin-6-yl)picolinamide;
(S)-2-(3-hydroxypyrrolidin-1-yl)-N-(2-morpholino-5-(piperidin-1-yl)oxazolo[4,5-b]pyridin-6-yl)oxazole-4-carboxamide;
(S)-N-(5-cyclopropyl-2-morpholinooxazolo[4,5-b]pyridin-6-yl)-2-(3-hydroxypyrrolidin-1-yl)oxazole-4-carboxamide;
(S)-2-(3-aminopyrrolidin-1-yl)-N-(5-cyclopropyl-2-morpholinooxazolo[4,5-b]pyridin-6-yl)oxazole-4-carboxamide;
2-(2-methylpyridin-4-yl)-N-(5-(piperidin-1-yl)-2-(pyrrolidin-1-yl)oxazolo[4,5-b]pyridin-6-yl)oxazole-4-carboxamide hydrochloride;
N-(2-(2,6-dimethylmorpholino)-5-(piperidin-1-yl)oxazolo[4,5-b]pyridin-6-yl)-2-(2-methylpyridin-4-yl)oxazole-4-carboxamide hydrochloride;
N-(2,5-di(piperidin-1-yl)thiazolo[4,5-b]pyridin-6-yl)-6-(1-methyl-1H-pyrazol-4-yl)picolinamide hydrochloride;
6-(1-methyl-1H-pyrazol-4-yl)-N-(2-morpholino-5-(piperidin-1-yl)thiazolo[4,5-b]pyridin-6-yl)picolinamide;
N-(2,5-di(piperidin-1-yl)thiazolo[4,5-b]pyridin-6-yl)-2-(2-methylpyridin-3-yl)oxazole-4-carboxamide hydrochloride;
N-(2-((2S,6R)-2,6-dimethylmorpholino)-5-(piperidin-1-yl)thiazolo[4,5-b]pyridin-6-yl)-2-(2-methylpyridin-4-yl)oxazole-4-carboxamide;
2-(2-methylpyridin-3-yl)-N-(2-morpholino-5-(piperidin-1-yl)thiazolo[4,5-b]pyridin-6-yl)oxazole-4-carboxamide;
2-(2-hydroxypyridin-3-yl)-N-(2-morpholino-5-(piperidin-1-yl)thiazolo[4,5-b]pyridin-6-yl)oxazole-4-carboxamide;
N-(2,5-di(piperidin-1-yl)thiazolo[4,5-b]pyridin-6-yl)-2-(2-methoxypyridin-4-yl)oxazole-4-carboxamide;
2-(6-methoxypyridin-3-yl)-N-(2-morpholino-5-(piperidin-1-yl)thiazolo[4,5-b]pyridin-6-yl)oxazole-4-carboxamide;
2-(2-methoxypyridin-4-yl)-N-(2-morpholino-5-(piperidin-1-yl)thiazolo[4,5-b]pyridin-6-yl)oxazole-4-carboxamide;
(S)-N-(5-(3-fluoropiperidin-1-yl)-2-morpholinothiazolo[4,5-b]pyridin-6-yl)-2-(2-methylpyridin-4-yl)oxazole-4-carboxamide;
2-(6-methylpyridin-3-yl)-N-(2-morpholino-5-(piperidin-1-yl)thiazolo[4,5-b]pyridin-6-yl)oxazole-4-carboxamide;
2-(3-methylpyridin-4-yl)-N-(2-morpholino-5-(piperidin-1-yl)thiazolo[4,5-b]pyridin-6-yl)oxazole-4-carboxamide;
(S)-6-(3-aminopyrrolidin-1-yl)-N-(2-morpholino-5-(piperidin-1-yl)thiazolo[4,5-b]pyridin-6-yl)picolinamide;
(S)-6-(3-hydroxypyrrolidin-1-yl)-N-(2-morpholino-5-(piperidin-1-yl)thiazolo[4,5-b]pyridin-6-yl)picolinamide;
(S)-6-(3-aminopyrrolidin-1-yl)-N-(2,5-di(piperidin-1-yl)thiazolo[4,5-b]pyridin-6-yl)picolinamide;
(S)-N-(2,5-di(piperidin-1-yl)thiazolo[4,5-b]pyridin-6-yl)-6-(3-hydroxypyrrolidin-1-yl)picolinamide;
(S)-2-(3-aminopyrrolidin-1-yl)-N-(2-morpholino-5-(piperidin-1-yl)thiazolo[4,5-b]pyridin-6-yl)oxazole-4-carboxamide;
(S)-N-(5-(3-aminopyrrolidin-1-yl)-2-morpholinothiazolo[4,5-b]pyridin-6-yl)-2-(2-methylpyridin-4-yl)oxazole-4-carboxamide;
(S)-2-(3-aminopyrrolidin-1-yl)-N-(5-cyclopropyl-2-morpholinothiazolo[4,5-b]pyridin-6-yl)oxazole-4-carboxamide;
N-(5-cyclopropyl-2-morpholinothiazolo[4,5-b]pyridin-6-yl)-2-(2-methylpyridin-4-yl)oxazole-4-carboxamide;

(S)-2-(3-hydroxypyrrolidin-1-yl)-N-(2-morpholino-5-(piperidin-1-yl)thiazolo[4,5-b]pyridin-6-yl)oxazole-4-carboxamide;
(S)-N-(5-(3-hydroxypyrrolidin-1-yl)-2-morpholinothiazolo[4,5-b]pyridin-6-yl)-2-(2-methylpyridin-4-yl)oxazole-4-carboxamide;
(S)-N-(5-cyclopropyl-2-morpholinothiazolo[4,5-b]pyridin-6-yl)-6-(3-hydroxypyrrolidin-1-yl)picolinamide;
(S)-N-(5-cyclopropyl-2-morpholinothiazolo[4,5-b]pyridin-6-yl)-2-(3-hydroxypyrrolidin-1-yl)oxazole-4-carboxamide;
(S)-N-(5-cyclopropyl-2-morpholinothiazolo[4,5-b]pyridin-6-yl)-6-(1-(2-hydroxypropyl)-1H-pyrazol-4-yl)picolinamide;
(S)-N-(5-cyclopropyl-2-morpholinothiazolo[4,5-b]pyridin-6-yl)-2-(1-(2-hydroxypropyl)-1H-pyrazol-4-yl)oxazole-4-carboxamide;
N-(5-(3-hydroxypyrrolidin-1-yl)-2-morpholinothiazolo[4,5-b]pyridin-6-yl)-2-(6-methoxypyridin-3-yl)oxazole-4-carboxamide;
(S)-N-(5-(3-hydroxypyrrolidin-1-yl)-2-morpholinothiazolo[4,5-b]pyridin-6-yl)-2-(6-methoxypyridin-3-yl)oxazole-4-carboxamide;
(R)-N-(5-(3-hydroxypyrrolidin-1-yl)-2-morpholinothiazolo[4,5-b]pyridin-6-yl)-2-(6-methoxypyridin-3-yl)oxazole-4-carboxamide;
(S)-N-(5-(azetidin-1-yl)-2-morpholinothiazolo[4,5-b]pyridin-6-yl)-6-(3-hydroxypyrrolidin-1-yl)picolinamide;
N-(5-(3-hydroxyazetidin-1-yl)-2-morpholinothiazolo[4,5-b]pyridin-6-yl)-2-(2-methylpyridin-4-yl)oxazole-4-carboxamide;
(S)-N-(5-(3-hydroxypyrrolidin-1-yl)-2-morpholinothiazolo[4,5-b]pyridin-6-yl)-5-(2-methylpyridin-4-yl)thiophene-2-carboxamide;
(S)-N-(5-(3-hydroxypyrrolidin-1-yl)-2-morpholinothiazolo[4,5-b]pyridin-6-yl)-5-(2-methylpyridin-4-yl)furan-2-carboxamide;
(S)-N-(5-(3-hydroxypiperidin-1-yl)-2-morpholinothiazolo[4,5-b]pyridin-6-yl)-2-(2-methylpyridin-4-yl)oxazole-4-carboxamide;
N-(5-(4-hydroxypiperidin-1-yl)-2-morpholinothiazolo[4,5-b]pyridin-6-yl)-2-(2-methylpyridin-4-yl)oxazole-4-carboxamide;
(R)-N-(5-(3-hydroxypyrrolidin-1-yl)-2-morpholinothiazolo[4,5-b]pyridin-6-yl)-2-(2-methylpyridin-4-yl)oxazole-4-carboxamide;
N-(5-(4-hydroxypiperidin-1-yl)-2-morpholinothiazolo[4,5-b]pyridin-6-yl)-5-(2-methylpyridin-4-yl)furan-2-carboxamide;
N-(5-(azetidin-1-yl)-2-(piperidin-1-yl)thiazolo[4,5-b]pyridin-6-yl)-2-(2-methylpyridin-4-yl)oxazole-4-carboxamide;
2-(2-methylpyridin-4-yl)-N-(2-(piperidin-1-yl)-5-(pyrrolidin-1-yl)thiazolo[4,5-b]pyridin-6-yl)oxazole-4-carboxamide;
2-(2-methylpyridin-4-yl)-N-(2-morpholino-5-(pyrrolidin-1-yl)thiazolo[4,5-b]pyridin-6-yl)oxazole-4-carboxamide;
5-(2-methylpyridin-4-yl)-N-(2-morpholino-5-(piperidin-1-yl)thiazolo[4,5-b]pyridin-6-yl)furan-2-carboxamide;
N-(5-(azepan-1-yl)-2-morpholinothiazolo[4,5-b]pyridin-6-yl)-2-(2-methylpyridin-4-yl)oxazole-4-carboxamide;
2-(2-aminopyridin-4-yl)-N-(2-morpholino-5-(piperidin-1-yl)thiazolo[4,5-b]pyridin-6-yl)oxazole-4-carboxamide hydrochloride;
N-(5-(azetidin-1-yl)-2-morpholinothiazolo[4,5-b]pyridin-6-yl)-2-(2-methylpyridin-4-yl)oxazole-4-carboxamide;
(R)-N-(5-(3-hydroxypiperidin-1-yl)-2-morpholinothiazolo[4,5-b]pyridin-6-yl)-2-(2-methylpyridin-4-yl)oxazole-4-carboxamide;
(R)-N-(5-(3-hydroxypiperidin-1-yl)-2-morpholinothiazolo[4,5-b]pyridin-6-yl)-5-(2-methylpyridin-4-yl)furan-2-carboxamide;
(S)-6-(1-(2-hydroxypropyl)-1H-pyrazol-4-yl)-N-(2-morpholino-5-(piperidin-1-yl)thiazolo[4,5-b]pyridin-6-yl)picolinamide;
N-(5-(4-fluoropiperidin-1-yl)-2-morpholinothiazolo[4,5-b]pyridin-6-yl)-5-(2-methylpyridin-4-yl)furan-2-carboxamide;
N-(5-(4-fluoropiperidin-1-yl)-2-morpholinothiazolo[4,5-b]pyridin-6-yl)-2-(2-methylpyridin-4-yl)oxazole-4-carboxamide hydrochloride;
N-(5-(1-methyl-1H-pyrazol-4-yl)-2-morpholinothiazolo[4,5-b]pyridin-6-yl)-2-(2-methylpyridin-4-yl)oxazole-4-carboxamide;
N-(5-(3-fluorophenyl)-2-morpholinothiazolo[4,5-b]pyridin-6-yl)-2-(2-methylpyridin-4-yl)oxazole-4-carboxamide;
N-(5-(4-hydroxypiperidin-1-yl)-2-morpholinothiazolo[4,5-b]pyridin-6-yl)-5-(2-methylpyridin-4-yl)furan-2-carboxamide;
N-(5-(3-fluoropiperidin-1-yl)-2-morpholinothiazolo[4,5-b]pyridin-6-yl)-5-(2-methylpyridin-4-yl)furan-2-carboxamide;
(S)-N-(5-(3-hydroxypyrrolidin-1-yl)-2-morpholinoooxazolo[4,5-b]pyridin-6-yl)-2-(6-methoxypyridin-3-yl)oxazole-4-carboxamide;
N-(5-(3-hydroxypyrrolidin-1-yl)-2-morpholinoooxazolo[4,5-b]pyridin-6-yl)-2-(2-methylpyridin-4-yl)oxazole-4-carboxamide;
(R)-N-(5-(3-hydroxypyrrolidin-1-yl)-2-morpholinoooxazolo[4,5-b]pyridin-6-yl)-2-(6-methoxypyridin-3-yl)oxazole-4-carboxamide;
N-(5-(3-hydroxypyrrolidin-1-yl)-2-morpholinoooxazolo[4,5-b]pyridin-6-yl)-2-(6-methoxypyridin-3-yl)oxazole-4-carboxamide;
(S)-N-(5-(3-hydroxypyrrolidin-1-yl)-2-morpholinoooxazolo[4,5-b]pyridin-6-yl)-5-(2-methylpyridin-4-yl)furan-2-carboxamide;
(S)-N-(5-(3-hydroxypyrrolidin-1-yl)-2-morpholinoooxazolo[4,5-b]pyridin-6-yl)-5-(2-methylpyridin-4-yl)thiophene-2-carboxamide;

N-(5-(azetidin-1-yl)-2-(piperidin-1-yl)oxazolo[4,5-b]pyridin-6-yl)-2-(2-methylpyridin-4-yl)oxazole-4-carboxamide;
2-(2-methylpyridin-4-yl)-N-(2-(piperidin-1-yl)-5-(pyrrolidin-1-yl)oxazolo[4,5-b]pyridin-6-yl)oxazole-4-carboxamide;
5-(2-methylpyridin-4-yl)-N-(2-morpholino-5-(piperidin-1-yl)oxazolo[4,5-b]pyridin-6-yl)furan-2-carboxamide;
N-(5-(azetidin-1-yl)-2-morpholinooxazolo[4,5-b]pyridin-6-yl)-2-(2-methylpyridin-4-yl)oxazole-4-carboxamide;
2-(2-methylpyridin-4-yl)-N-(2-morpholino-5-(pyrrolidin-1-yl)oxazolo[4,5-b]pyridin-6-yl)oxazole-4-carboxamide;
N-(5-(4-hydroxypiperidin-1-yl)-2-morpholinooxazolo[4,5-b]pyridin-6-yl)-5-(2-methylpyridin-4-yl)furan-2-carboxamide;
(R)-N-(5-(3-hydroxypiperidin-1-yl)-2-morpholinooxazolo[4,5-b]pyridin-6-yl)-5-(2-methylpyridin-4-yl)furan-2-carboxamide;
N-(5-(furan-3-yl)-2-morpholinooxazolo[4,5-b]pyridin-6-yl)-2-(2-methylpyridin-4-yl)oxazole-4-carboxamide;
N-(5-(3-fluoropiperidin-1-yl)-2-morpholinooxazolo[4,5-b]pyridin-6-yl)-2-(2-methylpyridin-4-yl)oxazole-4-carboxamide;
N-(5-(4-hydroxypiperidin-1-yl)-2-morpholinooxazolo[4,5-b]pyridin-6-yl)-2-(2-methylpyridin-4-yl)oxazole-4-carboxamide;
N-(5-(4-fluoropiperidin-1-yl)-2-morpholinooxazolo[4,5-b]pyridin-6-yl)-2-(2-methylpyridin-4-yl)oxazole-4-carboxamide;
(S)-N-(5-(3-aminopiperidin-1-yl)-2-morpholinothiazolo[4,5-b]pyridin-6-yl)-2-(2-methylpyridin-4-yl)oxazole-4-carboxamide;
2-(2-methylpyridin-4-yl)-N-(2-morpholino-5-(1H-pyrazol-4-yl)thiazolo[4,5-b]pyridin-6-yl)oxazole-4-carboxamide;
N-(5-(6-fluoropyridin-3-yl)-2-morpholinothiazolo[4,5-b]pyridin-6-yl)-2-(2-methylpyridin-4-yl)oxazole-4-carboxamide;
N-(5-(3-hydroxy-8-azabicyclo[3.2.1]octan-8-yl)-2-morpholinothiazolo[4,5-b]pyridin-6-yl)-2-(2-methylpyridin-4-yl)oxazole-4-carboxamide;
N-(2-(3-hydroxypiperidin-1-yl)-5-(piperidin-1-yl)thiazolo[4,5-b]pyridin-6-yl)-2-(2-methylpyridin-4-yl)oxazole-4-carboxamide;
2-(2-acetamidopyridin-4-yl)-N-(5-(4-hydroxypiperidin-1-yl)-2-morpholinothiazolo[4,5-b]pyridin-6-yl)oxazole-4-carboxamide;
N-(2-(3-hydroxypiperidin-1-yl)-5-(4-hydroxypiperidin-1-yl)thiazolo[4,5-b]pyridin-6-yl)-2-(2-methylpyridin-4-yl)oxazole-4-carboxamide;
2-(2-acetamidopyridin-4-yl)-N-(5-(3-hydroxypiperidin-1-yl)-2-morpholinothiazolo[4,5-b]pyridin-6-yl)oxazole-4-carboxamide;
2-(2-aminopyridin-4-yl)-N-(5-(3-hydroxypiperidin-1-yl)-2-morpholinothiazolo[4,5-b]pyridin-6-yl)oxazole-4-carboxamide hydrochloride;
5-(2-aminopyridin-4-yl)-N-(5-(4-hydroxypiperidin-1-yl)-2-morpholinothiazolo[4,5-b]pyridin-6-yl)furan-3-carboxamide hydrochloride;
2-(2-aminopyridin-4-yl)-N-(5-(4-hydroxypiperidin-1-yl)-2-morpholinothiazolo[4,5-b]pyridin-6-yl)oxazole-4-carboxamide hydrochloride;
2-(2-aminopyridin-4-yl)-N-(5-(4-fluoropiperidin-1-yl)-2-morpholinothiazolo[4,5-b]pyridin-6-yl)oxazole-4-carboxamide hydrochloride;
N-(5-(2-fluoropyridin-4-yl)-2-morpholinothiazolo[4,5-b]pyridin-6-yl)-2-(2-methylpyridin-4-yl)oxazole-4-carboxamide;
N-(5-(4-fluoropiperidin-1-yl)-2-(3-hydroxypiperidin-1-yl)thiazolo[4,5-b]pyridin-6-yl)-2-(2-methylpyridin-4-yl)oxazole-4-carboxamide;
N-(5-(4-aminopiperidin-1-yl)-2-(3-hydroxypiperidin-1-yl)thiazolo[4,5-b]pyridin-6-yl)-2-(2-methylpyridin-4-yl)oxazole-4-carboxamide hydrochloride; and
N-(5-(2-hydroxypyridin-4-yl)-2-morpholinothiazolo[4,5-b]pyridin-6-yl)-2-(2-methylpyridin-4-yl)oxazole-4-carboxamide hydrochloride;

or a pharmaceutically acceptable salt or a stereoisomer thereof.

In certain preferred embodiments, the IRAK4 inhibitor is

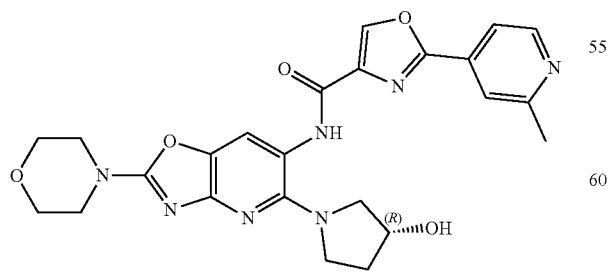

(i.e., Compound 1) or a pharmaceutically acceptable salt thereof.

In another embodiment, the IRAK4 inhibitor has a structure represented by formula (III):

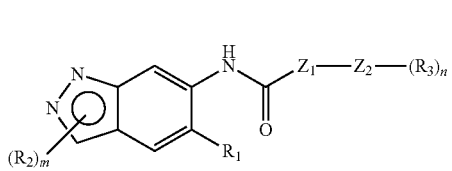

(III)

or a pharmaceutically acceptable salt thereof;
wherein,
$Z_1$ represents optionally substituted cycloalkyl, optionally substituted aryl, optionally substituted heterocyclyl or is absent;
$Z_2$ represents optionally substituted cycloalkyl, optionally substituted aryl or optionally substituted heterocyclyl;

R₁ is hydrogen, optionally substituted alkyl, amino, halo, cyano, optionally substituted cycloalkyl, optionally substituted aryl, optionally substituted heterocyclyl, optionally substituted arylalkyl or optionally substituted heterocyclylalkyl;

R₂ at each occurrence is amino, optionally substituted alkyl, optionally substituted cycloalkyl, optionally substituted aryl, optionally substituted heterocyclyl, optionally substituted arylalkyl or optionally substituted heterocyclylalkyl;

R₃ at each occurrence is hydroxy, halo, optionally substituted alkyl, optionally substituted alkoxy, optionally substituted cycloalkyl or —NR$_a$R$_b$;

R$_a$ and R$_b$, independently for each occurrence, are hydrogen, optionally substituted alkyl, optionally substituted acyl, optionally substituted cycloalkyl, optionally substituted aryl, optionally substituted heterocyclyl, optionally substituted arylalkyl or optionally substituted heterocyclylalkyl;

m, at ach occurrence, is 0, 1 or 2; and n, at each occurrence, is 0, 1, or 2.

In certain embodiments, Z₁ is an optionally substituted heterocyclyl.

In certain embodiments, Z₁ represents cycloalkyl, aryl, or heterocyclyl, optionally substituted by one or more substituents selected, independently for each occurrence, from hydroxy, halo, alkyl, cycloalkyl, or NR$_a$R$_b$.

In certain embodiments, Z₁ is an optionally substituted heteroaryl; wherein the optional substituent is alkyl or cycloalkyl.

In certain embodiments, Z₁ is tetrazolyl, thienyl, triazolyl, pyrrolyl, pyridyl, pyranyl, pyrazinyl, pyridazinyl, pyrimidyl, imidazolyl, oxadiazolyl, thiadiazolyl, thiazolyl, isothiazolyl, oxazolyl, furanyl, pyrazolyl, benzisoxazolyl, benzothiazolyl, benzofuranyl, benzothienyl, benzotriazinyl, phthalazinyl, thianthrene, dibenzofuranyl, dibenzothienyl, benzimidazolyl, indolyl, isoindolyl, indazolyl, quinolinyl, isoquinolinyl, quinazolinyl, quinoxalinyl, purinyl, pteridinyl, 9H-carbazolyl, α-carboline, indolizinyl, benzoisothiazolyl, benzoxazolyl, pyrrolopyridyl, furopyridinyl, purinyl, benzothiadiazolyl, benzooxadiazolyl, benzotriazolyl, benzotriadiazolyl, carbazolyl, dibenzothienyl, acridinyl and pyrazolopyrimidyl; each of which is optionally substituted.

In certain embodiments, Z₁ is tetrazolyl, thienyl, triazolyl, pyrrolyl, pyridyl, pyranyl, pyrazinyl, pyridazinyl, pyrimidyl, imidazolyl, oxadiazolyl, thiadiazolyl, thiazolyl, isothiazolyl, oxazolyl, furanyl or pyrazolyl.

In certain embodiments, Z₁ is pyridyl or oxazolyl; wherein the oxazolyl group is optionally substituted with alkyl; in particular alkyl is methyl.

In certain embodiments, Z₁ is absent.

In certain embodiments, Z₂ is cycloalkyl, aryl or heterocyclyl.

In certain embodiments, Z₂ represents cycloalkyl, aryl, or heterocyclyl, optionally substituted by one or more substituents selected from hydroxy, halo, alkyl, alkoxyl, cycloalkyl, —NR$_a$R$_b$, or cycloalkoxy.

In certain embodiments, Z₂ is heterocyclyl.

In certain embodiments, Z₂ is azetidinyl, oxetanyl, furanyl, piperidinyl, morpholinyl, piperazinyl, thiomorpholinyl, 1,4-dioxanyl, tetrahydropyranyl, tetrahydrofuranyl, tetrahydropyridyl, tetrazolyl, thienyl, triazolyl, pyrrolyl, pyridyl, pyranyl, pyrazinyl, pyridazinyl, pyrimidyl, imidazolyl, imidazolyl, thiadiazolyl, thiazolyl, thiazolidinyl, isothiazolyl, oxadiazolyl, oxazolyl, pyrazolyl, pyrrolidinyl, oxazolidinyl, pyrazolidinyl, benzisoxazolyl, benzothiazolyl, benzofuranyl, benzothienyl, benzotriazinyl, indolyl, isoindolyl, indazolyl, quinolinyl, isoquinolinyl pyrrolopyridyl or pyrazolopyrimidyl.

In certain embodiments, Z₂ is pyridyl, piperazinyl, pyrimidyl, pyrrolidinyl, 1,2,3,4-tetrahydropyridyl, piperidinyl, pyrazolopyrimidyl or pyrrolopyridyl.

In certain embodiments, the IRAK4 inhibitor has a structure represented by formula (IIIA):

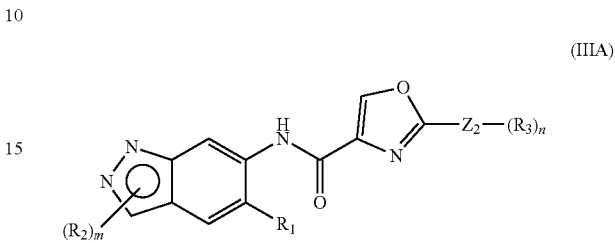

or a pharmaceutically acceptable salt thereof.

In certain embodiments, the IRAK4 inhibitor has a structure represented by formula (IIIB):

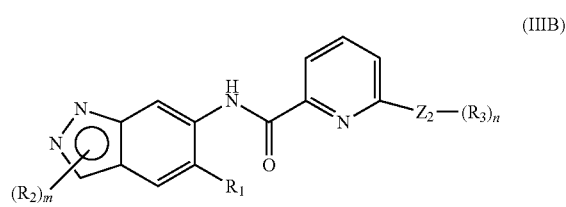

or a pharmaceutically acceptable salt thereof.

In certain embodiments, the group

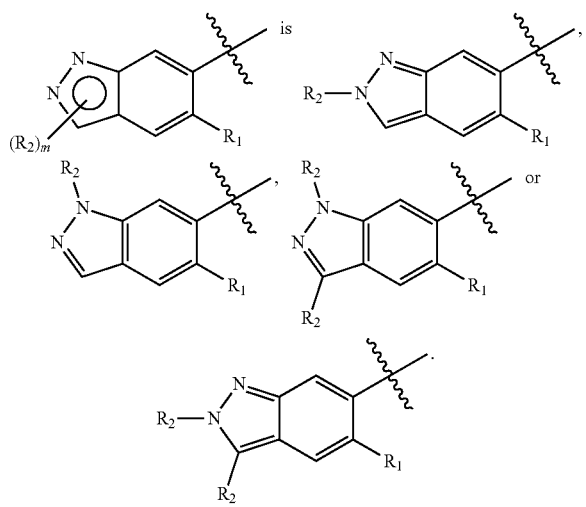

In certain embodiments, Z₂ is pyridyl.

In certain embodiments, Z₂ is pyrrolidinyl.

In certain embodiments, Z₂ is piperidinyl, piperazinyl, tetrahydropyridyl, pyrimidyl or pyrazolopyridyl.

In certain embodiments, R₁ is hydrogen, optionally substituted alkyl, amino, halo, cyano, optionally substituted cycloalkyl, optionally substituted aryl, optionally substituted heterocyclyl, optionally substituted arylalkyl or optionally substituted heterocyclylalkyl.

In certain embodiments, the present methods include a compound of formula (III) or a pharmaceutically acceptable salt, wherein $R_1$ is alkyl, cycloalkyl, aryl, heterocyclyl, arylalkyl, optionally substituted with one or more substituents selected, independently for each occurrence, from hydroxy, halo, alkyl, or hydroxyalkyl.

In certain embodiments, $R_1$ is heterocyclyl; optionally substituted with halogen, hydroxyl or hydroxyalkyl.

In certain embodiments, $R_1$ is optionally substituted azetidinyl, piperidinyl, morpholinyl, pyrrolidinyl or azepanyl.

In certain embodiments, $R_1$ is piperidinyl, optionally substituted with hydroxyl.

In certain embodiments, $R_1$ is pyrrolidinyl, optionally substituted with hydroxyl.

In certain embodiments, $R_2$, at each occurrence, is amino, optionally substituted alkyl, optionally substituted cycloalkyl, optionally substituted aryl, optionally substituted heterocyclyl, optionally substituted arylalkyl or optionally substituted heterocyclylalkyl.

In certain embodiments, $R_2$ is alkyl, cycloalkyl, aryl, heterocyclyl, arylalkyl, or heterocyclylalkyl, optionally substituted with one or more substituents selected, independently for each occurrence, from alkyl, cycloalkyl, or heterocyclyl.

In certain embodiments, $R_2$ is optionally substituted alkyl, preferably methyl.

In certain embodiments, $R_2$ is optionally substituted cycloalkyl, preferably, cyclopropyl.

In certain embodiments, $R_3$, at each occurrence, is hydroxy, halo, optionally substituted alkyl, optionally substituted alkoxy, optionally substituted cycloalkyl or —$NR_aR_b$; wherein $R_a$ is hydrogen or optionally substituted alkyl; and $R_b$ is hydrogen, optionally substituted alkyl, optionally substituted acyl, hydroxyalkyl or —$SO_2$-alkyl.

In certain embodiments, $Z_1$ is optionally substituted pyridyl; $Z_2$ is pyrrolidinyl; $R_1$ is an optionally substituted groups selected from piperidinyl or pyrrolidinyl; $R_2$ is optionally substituted alkyl; $R_3$ is halogen, alkyl, —$NR_aR_b$, hydroxyl or hydroxyalkyl; $R_a$ is hydrogen or alkyl; and $R_b$ is hydrogen or hydroxyalkyl.

In certain embodiments, $Z_1$ is oxazolyl; $Z_2$ is pyridyl, pyrimidyl or pyrrolidinyl, piperidinyl, tetrahydropyridyl, piperazinyl, pyrrolopyridyl; $R_1$ is an optionally substituted group selected from piperidinyl or pyrrolidinyl; $R_2$ is optionally substituted alkyl or cyclopropyl; $R_3$ is halogen, alkyl, alkoxy, —$NR_aR_b$, hydroxyl, hydroxyalkyl optionally substituted cyclopropyl; $R_a$ is hydrogen or alkyl; and $R_b$ is hydrogen, alkyl, acyl, hydroxyalkyl, —$SO_2$-alkyl or optionally substituted cycloalkyl.

In certain embodiments, 'm' is 0.
In certain embodiments, 'm' is 1.
In certain embodiments, 'm' is 2.
In certain embodiments, 'n' is 0.
In certain embodiments, 'n' is 1.
In certain embodiments, 'n' is 2.
In certain embodiments, the IRAK4 inhibitor is selected from:

N-(1-methyl-5-(piperidin-1-yl)-1H-indazol-6-yl)-2-(2-methylpyridin-4-yl)oxazole-4-carboxamide hydrochloride;
N-(2-methyl-5-(piperidin-1-yl)-2H-indazol-6-yl)-2-(2-methylpyridin-4-yl)oxazole-4-carboxamide hydrochloride;
(S)-6-(3-hydroxypyrrolidin-1-yl)-N-(2-methyl-5-(piperidin-1-yl)-2H-indazol-6-yl)picolinamide;
(S)-2-(3-aminopyrrolidin-1-yl)-N-(1-methyl-5-(piperidin-1-yl)-1H-indazol-6-yl)oxazole-4-carboxamide;
(S)-2-(3-aminopyrrolidin-1-yl)-N-(2-methyl-5-(piperidin-1-yl)-2H-indazol-6-yl)oxazole-4-carboxamide;
(S)-2-(3-hydroxypyrrolidin-1-yl)-N-(2-methyl-5-(piperidin-1-yl)-2H-indazol-6-yl)oxazole-4-carboxamide;
(S)-6-(3-aminopyrrolidin-1-yl)-N-(2-methyl-5-(piperidin-1-yl)-2H-indazol-6-yl)picolinamide;
(S)-6-(3-aminopyrrolidin-1-yl)-N-(1-methyl-5-(piperidin-1-yl)-1H-indazol-6-yl)picolinamide;
(S)-6-(3-hydroxypyrrolidin-1-yl)-N-(1-methyl-5-(piperidin-1-yl)-1H-indazol-6-yl)picolinamide;
(S)-2-(3-hydroxypyrrolidin-1-yl)-N-(1-methyl-5-(piperidin-1-yl)-1H-indazol-6-yl)oxazole-4-carboxamide;
(S)-N-(5-(3-hydroxypyrrolidin-1-yl)-1-methyl-1H-indazol-6-yl)-2-(2-methylpyridin-4-yl)oxazole-4-carboxamide;
N-(5-(3-hydroxypiperidin-1-yl)-1-methyl-1H-indazol-6-yl)-2-(2-methylpyridin-4-yl)oxazole-4-carboxamide;
N-(5-(3-hydroxypiperidin-1-yl)-2-methyl-2H-indazol-6-yl)-2-(2-methylpyridin-4-yl)oxazole-4-carboxamide;
N-(5-(3-fluoropiperidin-1-yl)-2-methyl-2H-indazol-6-yl)-2-(2-methylpyridin-4-yl)oxazole-4-carboxamide;
(S)-2-(2-acetamidopyridin-4-yl)-N-(5-(3-hydroxypyrrolidin-1-yl)-1-methyl-1H-indazol-6-yl)oxazole-4-carboxamide;
N-(5-(3-fluoropiperidin-1-yl)-1-methyl-1H-indazol-6-yl)-2-(2-methylpyridin-4-yl)oxazole-4-carboxamide;
N-(5-(4-hydroxypiperidin-1-yl)-1-methyl-1H-indazol-6-yl)-2-(2-methylpyridin-4-yl)oxazole-4-carboxamide;
(S)-2-(2-aminopyridin-4-yl)-N-(5-(3-hydroxypyrrolidin-1-yl)-1-methyl-1H-indazol-6-yl)oxazole-4-carboxamide;
N-(5-(4-fluoropiperidin-1-yl)-1-methyl-1H-indazol-6-yl)-2-(2-methylpyridin-4-yl)oxazole-4-carboxamide;
N-(5-(4-(hydroxymethyl)piperidin-1-yl)-1-methyl-1H-indazol-6-yl)-2-(2-methylpyridin-4-yl)oxazole-4-carboxamide;
(S)-2-(2,6-dimethylpyridin-4-yl)-N-(5-(3-hydroxypyrrolidin-1-yl)-1-methyl-1H-indazol-6-yl)oxazole-4-carboxamide;
(R)-N-(5-(3-hydroxypyrrolidin-1-yl)-1-methyl-1H-indazol-6-yl)-2-(2-methylpyridin-4-yl)oxazole-4-carboxamide;
(S)-2-(2-aminopyridin-3-yl)-N-(5-(3-hydroxypyrrolidin-1-yl)-1-methyl-1H-indazol-6-yl)oxazole-4-carboxamide Hydrochloride;
6-((S)-3-hydroxypyrrolidin-1-yl)-N-(5-((R)-3-hydroxypyrrolidin-1-yl)-1-methyl-1H-indazol-6-yl)picolinamide;
(S)-N-(5-(3-hydroxypyrrolidin-1-yl)-1-methyl-1H-indazol-6-yl)pyrazolo[1,5-a]pyrimidine-3-carboxamide;
6-((S)-3-hydroxypyrrolidin-1-yl)-N-(5-((S)-3-hydroxypyrrolidin-1-yl)-1-methyl-1H-indazol-6-yl)picolinamide;
(S)-N-(5-(3-hydroxypyrrolidin-1-yl)-1-methyl-1H-indazol-6-yl)-2-(1H-pyrrolo[2,3-b]pyridin-4-yl)oxazole-4-carboxamide;
(S)-N-(5-(3-hydroxypyrrolidin-1-yl)-1H-indazol-6-yl)-2-(2-methylpyridin-4-yl)oxazole-4-carboxamide;
(S)-2-(2-amino-3-fluoropyridin-4-yl)-N-(5-(3-hydroxypyrrolidin-1-yl)-1-methyl-1H-indazol-6-yl)oxazole-4-carboxamide;
(R)-2-(2-aminopyridin-3-yl)-N-(5-(3-hydroxypyrrolidin-1-yl)-1-methyl-1H-indazol-6-yl)oxazole-4-carboxamide hydrochloride;
(S)-N-(5-(3-hydroxypyrrolidin-1-yl)-1-methyl-1H-indazol-6-yl)-2-(4-methylpiperazin-1-yl)oxazole-4-carboxamide;
(S)-N-(5-(3-hydroxypyrrolidin-1-yl)-1-methyl-1H-indazol-6-yl)-2-(piperazin-1-yl)oxazole-4-carboxamide;
(S)-N-(1-ethyl-5-(3-hydroxypyrrolidin-1-yl)-1H-indazol-6-yl)-2-(2-methylpyridin-4-yl)oxazole-4-carboxamide hydrochloride;
(S)-N-(1-cyclopropyl-5-(3-hydroxypyrrolidin-1-yl)-1H-indazol-6-yl)-2-(2-methylpyridin-4-yl)oxazole-4-carboxamide hydrochloride;
(S)-N-(5-(3-hydroxypyrrolidin-1-yl)-1-methyl-1H-indazol-6-yl)-2-(1,2,3,6-tetrahydropyridin-4-yl)oxazole-4-carboxamide hydrochloride;
(S)-N-(5-(3-hydroxypyrrolidin-1-yl)-1-methyl-1H-indazol-6-yl)-2-(2-methylpyrimidin-4-yl)oxazole-4-carboxamide;
(S)-N-(5-(3-hydroxypyrrolidin-1-yl)-1-methyl-1H-indazol-6-yl)-4-methyl-2-(2-methylpyridin-4-yl)oxazole-5-carboxamide;
(S)-N-(5-(3-hydroxypyrrolidin-1-yl)-1-methyl-1H-indazol-6-yl)-2-(piperidin-4-yl)oxazole-4-carboxamide hydrochloride;
N-(5-(3-hydroxy-8-azabicyclo[3.2.1]octan-8-yl)-1-methyl-1H-indazol-6-yl)-2-(2-methylpyridin-4-yl)oxazole-4-carboxamide;
(S)-N-(5-(3-hydroxypyrrolidin-1-yl)-1-methyl-1H-indazol-6-yl)-2-(2-methylpyridin-4-yl)oxazole-5-carboxamide;
N-(5-(4-hydroxy-4-(hydroxymethyl)piperidin-1-yl)-1-methyl-1H-indazol-6-yl)-2-(2-methylpyridin-4-yl)oxazole-4-carboxamide hydrochloride;
(S)-N-(5-(3-hydroxypyrrolidin-1-yl)-1-methyl-1H-indazol-6-yl)-5-methyl-2-(2-methylpyridin-4-yl)oxazole-4-carboxamide;
(S)-2-(2-ethylpyridin-4-yl)-N-(5-(3-hydroxypyrrolidin-1-yl)-1-methyl-1H-indazol-6-yl)oxazole-4-carboxamide;

2-(2-aminopyridin-4-yl)-N-(5-(4-(hydroxymethyl)piperidin-1-yl)-1,3-dimethyl-1H-indazol-6-yl)oxazole-4-carboxamide hydrochloride;
(S)-N-(5-(3-hydroxypyrrolidin-1-yl)-1-(piperidin-4-ylmethyl)-1H-indazol-6-yl)-2-(2-methylpyridin-4-yl)oxazole-4-carboxamide;
N-(5-(4-(hydroxymethyl)piperidin-1-yl)-1,3-dimethyl-1H-indazol-6-yl)-2-(2-methylpyridin-4-yl)oxazole-4-carboxamide;
(S)-2-(2-cyclopropylpyridin-4-yl)-N-(5-(3-hydroxypyrrolidin-1-yl)-1-methyl-1H-indazol-6-yl)oxazole-4-carboxamide; and
N-(5-(4-hydroxypiperidin-1-yl)-2-methyl-2H-indazol-6-yl)pyrazolo[1,5-a]pyrimidine-3-carboxamide;

or a pharmaceutically acceptable salt thereof.

In other embodiments, the IRAK4 inhibitor is PF-06650833, BAY1830839, BAY1834845, R835, GS-5718, or ND-2158.

The IRAK4 inhibitor (e.g., Compound 1) may be administered in any amount or manner that elicits the desired response in the subject. For example, 100-400 mg of the IRAK4 inhibitor can be administered to the subject twice per day or 200-1000 mg of the IRAK4 inhibitor can be administered to the subject once per day. In certain embodiments, 100-400 mg of the IRAK4 inhibitor is administered to the subject twice per day. In certain embodiments, 200-400 mg of the IRAK4 inhibitor is administered to the subject twice per day. In certain preferred embodiments, 250-350 mg of the IRAK4 inhibitor is administered to the subject twice per day. In certain embodiments, about 50 mg, about 75 mg, about 100 mg, about 125 mg, about 150 mg, about 175 mg, about 200 mg, about 225 mg, about 250 mg, about 275 mg, about 300 mg, about 325 mg, about 350 mg, about 375 mg, about 400 mg, about 425 mg, about 450 mg, about 475 mg, or about 500 mg of the IRAK4 inhibitor is administered to the subject twice per day. In certain embodiments, about 50 mg, about 75 mg, about 100 mg, about 200 mg, about 225 mg, about 250 mg, about 275 mg, about 300 mg, about 325 mg, about 350 mg, about 375 mg, or about 400 mg of the IRAK4 inhibitor is administered to the subject twice per day. In certain embodiments, about 50 mg, about 100 mg, about 200 mg, or about 300 mg of the IRAK4 inhibitor is administered to the subject twice per day. In certain embodiments, about 50 mg of the IRAK4 inhibitor is administered to the subject twice per day. In other embodiments, about 200 mg of the IRAK4 inhibitor is administered to the subject twice per day. In other embodiments, about 225 mg of the IRAK4 inhibitor is administered to the subject twice per day. In other embodiments, about 250 mg of the IRAK4 inhibitor is administered to the subject twice per day. In other embodiments, about 275 mg of the IRAK4 inhibitor is administered to the subject twice per day. In particularly preferred embodiments, about 300 mg of the IRAK4 inhibitor is administered to the subject twice per day. In other embodiments, about 325 mg of the IRAK4 inhibitor is administered to the subject twice per day. In other embodiments, about 350 mg of the IRAK4 inhibitor is administered to the subject twice per day. In other embodiments, about 375 mg of the IRAK4 inhibitor is administered to the subject twice per day. In other embodiments, about 400 mg of the IRAK4 inhibitor is administered to the subject twice per day.

In certain embodiments, about 25 mg, about 50 mg, about 75 mg, about 100 mg, about 125 mg, about 150 mg, about 175 mg, about 200 mg, about 225 mg, about 250 mg, about 275 mg, about 300 mg, about 325 mg, about 350 mg, about 375 mg, about 400 mg, about 425 mg, about 450 mg, about 475 mg, or about 500 mg of the IRAK4 inhibitor to the subject once per day. In certain embodiments, about 50 mg of the IRAK4 inhibitor to the subject once per day. In certain embodiments, about 75 mg of the IRAK4 inhibitor to the subject once per day. In certain embodiments, about 100 mg of the IRAK4 inhibitor to the subject once per day. In certain embodiments, about 125 mg of the IRAK4 inhibitor to the subject once per day. In certain embodiments, about 150 mg of the IRAK4 inhibitor to the subject once per day.

In certain preferred embodiments, the IRAK4 inhibitor is orally administered to the subject. In certain embodiments, about 50 mg of the IRAK4 inhibitor is orally administered to the subject twice per day. In other embodiments, about 200 mg of the IRAK4 inhibitor is orally administered to the subject twice per day. In other embodiments, about 250 mg of the IRAK4 inhibitor is orally administered to the subject twice per day. In particularly preferred embodiments, about 300 mg of the IRAK4 inhibitor is orally administered to the subject twice per day. In other embodiments, about 325 mg of the IRAK4 inhibitor is orally administered to the subject twice per day. In other embodiments, about 350 mg of the IRAK4 inhibitor is orally administered to the subject twice per day. In other embodiments, about 375 mg of the IRAK4 inhibitor is orally administered to the subject twice per day. In other embodiments, about 400 mg of the IRAK4 inhibitor is orally administered to the subject twice per day. In other embodiments, about 50 mg of the IRAK4 inhibitor to the subject once per day. In yet other embodiments, about 75 mg of the IRAK4 inhibitor to the subject once per day. In yet other embodiments, about 100 mg of the IRAK4 inhibitor to the subject once per day. In yet other embodiments, about 125 mg of the IRAK4 inhibitor to the subject once per day. In yet other embodiments, about 150 mg of the IRAK4 inhibitor to the subject once per day.

IRAK4 Degraders of the Disclosure

In certain embodiments, the method comprises administering an IRAK4 degrader. In certain embodiments, the IRAK4 degrader is KT-474, KYM-001, or IRAKMiD. In certain embodiments, the IRAK4 degrader is an IRAK4 degrader disclosed in US 2019/0151295 A1, WO 2019/133531 A1, WO 2020/113233 A1, and WO 2021/011868 A1, the contents of each of which is hereby incorporated by reference in its entirety.

BCL-2 Inhibitors of the Disclosure

The combinations disclosed herein may be utilized in connection with any BCL-2 inhibitor. In certain preferred embodiments, the BCL-2 inhibitor is ventoclax. In certain embodiments, 400 mg of venetoclax is administered daily. In certain embodiments, the venetoclax is administered orally.

Nucleoside Analogs of the Disclosure

The combinations disclosed herein may be utilized in connection with any nucleoside analog. In certain embodiments, the nucleoside analog is an analog of cytidine. In certain embodiments, the nucleoside analog is azacitidine, decitabine, cytarabine, gemcitabine, 5'-deoxy-5-fluorouridine, fludarabine, cladribine, troxacitabine, or clofarabine. In certain preferred embodiments, the nucleoside analog is azacitidine. In certain embodiments, the azacitidine is administered at a dose of 75 mg/m$^2$ daily. In certain embodiments, the azacitidine is administered at a dose of 100 mg/m$^2$ daily. In certain embodiments, the azacitidine is administered subcutaneously. In other embodiments, the azacitidine is administered at a dose of 300 mg daily. In certain embodiments, the azacitidine is administered orally.

Cancers of the Disclosure

In certain embodiments, the cancer is a hematological malignancy, such as a leukemia or lymphoma, for example a non-Hodgkin's lymphoma. In certain embodiments, the hematological malignancy is myelogenous leukemia, myeloid leukemia (e.g., acute myeloid leukemia), myelodysplastic syndrome, lymphoblastic leukemia (e.g., acute lymphoblastic leukemia), chronic lymphocytic leukemia (CLL), small lymphocytic lymphoma (SLL), high risk CLL, follicular lymphoma, diffuse large B-cell lymphoma (DLBCL) (e.g., DLBCL or ABC-DLBLC), mantle cell lymphoma (MCL), Waldenstrom's macroglobulinemia (WM), multiple myeloma, marginal zone lymphoma (MZL), Burkitt's lymphoma, non-Burkitt high grade B cell lymphoma, extranodal marginal zone B cell lymphoma, transformed high grade B-cell lymphoma (HGBL), lymphoplasmacytic lymphoma (LPL), central nervous system lymphoma (CNSL), or MALT lymphoma. In certain embodiments, the hematological malignancy is myelogenous leukemia. In other embodiments, the hematological malignancy is myeloid leukemia (e.g., acute myeloid leukemia). In certain embodiments, the hematological malignancy is acute myeloid leukemia (e.g., AML). In certain embodiments, the AML is primary AML. In other embodiments, the AML is secondary AML. In certain embodiments, the AML is resistant to treatment with an fms related receptor tyrosine kinase 3 (FLT3) inhibitor. In certain embodiments, the AML is associated with a mutation in FLT3 kinase. In certain embodiments, the mutation is an internal tandem duplication (ITD). In certain embodiments, the mutation is a D835H, D835V, D835Y, K663Q, N841L, or F691L mutation. In certain embodiments, the mutation is a D835Y mutation. In yet other embodiments, the hematological malignancy is myelodysplastic syndromes (MDS). In certain embodiments, the MDS is high grade. In other embodiments, the MDS is low grade. In certain embodiments, the MDS is high risk. In yet other embodiments, the hematological malignancy is lymphoblastic leukemia (e.g., acute lymphoblastic leukemia). In yet other embodiments, the hematological malignancy is chronic lymphocytic leukemia (CLL). In certain embodiments, the CLL is high risk CLL. In yet other embodiments, the hematological malignancy is small lymphocytic lymphoma (SLL). In yet other embodiments, the hematological malignancy is follicular lymphoma. In yet other embodiments, the hematological malignancy is diffuse large B-cell lymphoma (DLBCL). In yet other embodiments, the hematological malignancy is activated B cell-like (ABC) DLBCL. In yet other embodiments, the hematological malignancy is germinal center B cell-like (GCB) DLBCL. In certain embodiments, the DLBCL is extranodal. In certain embodiments, the DLBCL is extranodal leg lymphoma, extranodal testicle lymphoma, or extra nodal not otherwise specified (NOS) type lymphoma. In yet other embodiments, the hematological malignancy is mantle cell lymphoma. In further embodiments, the hematological malignancy is Waldenstrom's macroglobulinemia. In certain embodiments, the DLBCL or WM is characterized by a L265P mutation in MYD88. In yet other embodiments, the hematological malignancy is multiple myeloma. In still other embodiments, the hematological malignancy is marginal zone lymphoma. In yet other embodiments, the hematological malignancy is Burkitt's lymphoma. In yet other embodiments, the hematological malignancy is non-Burkitt high grade B cell lymphoma. In still other embodiments, the hematological malignancy is extranodal marginal zone B cell lymphoma. In yet other embodiments, the hematological malignancy is transformed high grade B-cell lymphoma (HGBL). In yet other embodiments, the hematological malignancy is lymphoplasmacytic lymphoma (LPL). In yet other embodiments, the hematological malignancy is CNS lymphoma. In yet other embodiments, the CNS lymphoma is primary CNS lymphoma (PCNSL). In yet other embodiments, the hematological malignancy is MALT lymphoma. In certain embodiments, the hematological malignancies described above may be relapsed or refractory. In certain embodiments, the hematological malignancies described above are resistant to treatment with a BTK inhibitor. In certain embodiments, the hematological malignancies described above are resistant to treatment with a BTK inhibitor as a monotherapy. In certain embodiments, the hematological malignancies is resistant to treatment with ibrutinib, acalabrutinib, zanubrutinib, evobrutinib, ONO-4059, spebrutinib, or HM7 1224. In certain preferred embodiments, the hematological malignancy is resistant to treatment with ibrutinib.

In certain embodiments, the cancer is selected from brain cancer, kidney cancer, liver cancer, stomach cancer, penile cancer, vaginal cancer, ovarian cancer, gastric cancer, breast cancer, bladder cancer, colon cancer, prostate cancer, pancreatic cancer, lung cancer, cervical cancer, epidermal cancer, prostate cancer, head or neck cancer. In certain preferred embodiments, the cancer is pancreatic cancer. In other embodiments, the cancer is colon cancer. In certain embodiments, the cancer is a solid tumor. In various such embodiments, the cancer may be relapsed or refractory.

The combinations disclosed herein may be used as a first line therapy or they may be administered to patients who have failed to achieve a response, either partial or full, using one or more previous anti-cancer therapies or anti-inflammatory therapies. In certain embodiments, the subject has previously received at least one anti-cancer therapy. In certain embodiments, the patient has previously received one anti-cancer therapy. In other embodiments, the patient has previously received two anti-cancer therapies. In yet other embodiments, the patient has previously received three anti-cancer therapies. In yet other embodiments, the patient has previously received four anti-cancer therapies. In yet other embodiments, the patient has previously received five anti-cancer therapies. In certain embodiments, the at least one anti-cancer therapy is selected from an anti-CD20 antibody, a nitrogen mustard, a steroid, a purine analog, a DNA a topoisomerase inhibitor, a DNA intercalator, a tubulin inhibitor, a BCL-2 inhibitor, a proteasome inhibitor, a toll-like receptor inhibitor, a kinase inhibitor, an SRC kinase inhibitor, a PI3K kinase inhibitor, BTK inhibitor, a glutaminase inhibitor, a PD-1 inhibitor, a PD-L1 inhibitor and a methylating agent; or a combination thereof. In certain embodiments, the anti-cancer therapy is selected from ibrutinib, rituximab, bendamustine, bortezomib, dexamethasone, chlorambucil, cladribine, cyclophosphamide, doxorubicin, vincristine, venetoclax, ifosfamide, prednisone, oprozomib, ixazomib, acalabrutinib, zanubrutinib, IMO-08400, idelalisib, umbrelasib, CB-839, fludarabine, and thalidomide; or a combination thereof. In certain embodiments, the anti-cancer therapy is ibrutinib. In certain embodiments, the anti-cancer therapy is ibrutinib and rituximab. In certain embodiments, the anti-cancer therapy is bendamustine. In certain embodiments, the anti-cancer therapy is bendamustine and rituximab. In certain embodiments, the anti-cancer therapy is bortezomib. In certain embodiments, the anti-cancer therapy is bortezomib and dexamethasone. In certain embodiments, the anti-cancer therapy is bortezomib and rituximab. In certain embodiments, the anti-cancer therapy is bortezomib, rituximab, and dexamethasone. In certain embodiments, chlorambucil. In certain embodiments, the anti-cancer therapy is cladribine. In certain embodiments, the anti-cancer therapy is cladribine and rituximab. In certain embodiments, the anti-cancer therapy is cyclophosphamide, doxorubicin, vincristine, prednisone, and rituximab (i.e., CHOP-R). In certain embodiments, the anti-cancer therapy is cyclophosphamide, prednisone, and rituximab (i.e., CPR). In certain embodiments, the anti-cancer therapy is fludarabine. In certain embodiments, the anti-cancer therapy is fludarabine and rituximab. In certain embodiments, the anti-cancer therapy is fludarabine, cyclophosphamide, and rituximab. In certain preferred embodiments, the anti-cancer therapy is rituximab. In certain preferred embodiments, the anti-cancer therapy comprises rituximab. In certain embodiments, the anti-cancer therapy is rituximab, cyclophosphamide, and dexamethasone (i.e., RCD). In certain embodiments, the anti-cancer therapy is thalidomide. In certain embodiments, the anti-cancer therapy is thalidomide and rituximab. In certain embodiments, the anti-cancer therapy is venetoclax. In certain embodiments, the anti-cancer therapy is cyclophosphamide, bortezomib, and dexamethasone (i.e., R-CyBorD). In certain embodiments, the anti-cancer therapy is a hypomethylating agent. In certain embodiments, the subject has previously received at least 6 cycles of a hypomethylating agent. In certain embodiments, the anti-cancer therapy is a combination of any of the foregoing, for example the subject may first receive rituximab and then at a later date receive a combination of rituximab, cyclophosphamide, and dexamethasone (i.e., RCD).

The subject may also have received or been prepared for other, non-chemotherapeutic treatments, such as surgery, radiation, or a bone marrow transplant. In certain embodiments, the subject has previously received etoposide chemomobilization therapy. In certain embodiments, the subject has previously received a bone marrow transplant. In certain embodiments, the subject has previously received a stem cell transplant. In certain embodiments, the subject has previously received an autologous cell transplant. In certain embodiments, the subject has previously received an allogenic stem cell transplant. In certain embodiments, the subject has previously received a hematopoietic cell transplantation. In certain embodiments, the subject has previously received carmustine, etoposide, cytarabine, and melphalan (i.e., BEAM conditioning). In certain embodiments, the subject has previously received re-induction therapy.

The subject may have also previously exhibited a favorable outcome to prior therapy only to require additional treatment at a later date. In certain embodiments, the subject has previously achieved a partial response. In certain embodiments, the subject has previously achieved a good partial response. In certain embodiments, the subject has previously achieved a complete response. In certain embodiments, the cancer is relapsed. In certain embodiments, the cancer is refractory.

The subject may also have preexisting or developed one or more genetic mutations that render the subjects cancer more or less resistant to therapy. In certain embodiments, the subject has a mutation in RICTOR. In certain embodiments, the subject has a N1065S mutation in RICTOR. In certain preferred embodiments, the subject has a mutation in MYD88. In certain even further preferred embodiments, the subject has a L265P mutation in MYD88. In certain embodiments, the subject has a mutation in TET2. In certain embodiments, the subject does not have a mutation in CXCR4. In other embodiments, the subject has a mutation in CXCR4. In certain embodiments, the subject shows early progression. In certain embodiments, the subject has not previously received a BTK inhibitor.

In certain embodiments, following administration of the combinations, the subject achieves a partial response. In certain embodiments, following administration of the combinations, the subject achieves a good partial response. In other embodiments, following administration of the combinations, the subject achieves a complete response. In certain embodiments, the subject achieves a partial response within 7 days of receiving the combinations. In certain embodiments, the subject achieves a good partial response within 7 days of receiving the combinations. In certain embodiments, the subject achieves a complete response within 7 days of receiving the combinations. In certain embodiments, the subject's tumor volume is reduced by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, or about 95%. In certain embodiments, the subject's tumor volume is reduced by 5%. In certain embodiments, the subject's tumor volume is reduced by 10%. In certain embodiments, the subject's tumor volume is reduced by 15%. In certain embodiments, the subject's tumor volume is reduced by 20%. In certain embodiments, the subject's tumor volume is reduced by 25%. In certain embodiments, the subject's tumor volume is reduced by 30%. In certain embodiments, the subject's tumor volume is reduced by 35%. In certain embodiments, the subject's tumor volume is reduced by 40%. In certain embodiments, the subject's tumor volume is reduced by 45%. In certain embodiments, the subject's tumor volume is reduced by 50%. In certain embodiments, the subject's tumor volume is reduced by 55%. In certain embodiments, the subject's tumor volume is reduced by 60%. In certain embodiments, the subject's tumor volume is reduced by 65%. In certain embodiments, the subject's tumor volume is reduced by 70%. In certain embodiments, the subject's tumor volume is reduced by 80%. In certain embodiments, the subject's tumor volume is reduced by 85%. In certain embodiments, the subject's tumor volume is reduced by 90%. In certain embodiments, the subject's tumor volume is reduced by 95%.

Methods of Administration

The IRAK4 inhibitor or IRAK4 degrader, the BCL-2 inhibitor, and the nucleoside analog may be administered in a number of ways. For example, the IRAK4 inhibitor or IRAK4 degrader, BCL-2 inhibitor, and the nucleoside analog may be administered simultaneously.

In other embodiments, the IRAK4 inhibitor or IRAK4 degrader may be administered first, the BCL-2 inhibitor second, and the nucleoside analog third.

In yet other embodiments, the IRAK4 inhibitor or IRAK4 degrader may be administered first, the BCL-2 inhibitor third, and the nucleoside analog second. In yet other embodiments, the IRAK4 inhibitor or IRAK4 degrader may be administered second, the BCL-2 inhibitor first, and the nucleoside analog third. In yet other embodiments, the IRAK4 inhibitor or IRAK4 degrader may be administered second, the BCL-2 inhibitor third, and the nucleoside analog first. In yet other embodiments, the IRAK4 inhibitor or IRAK4 degrader may be administered third, the BCL-2 inhibitor first, and the nucleoside analog second. In yet other embodiments, the IRAK4 inhibitor or IRAK4 degrader may be administered third, the BCL-2 inhibitor second, and the nucleoside analog first. In certain embodiments, the IRAK4 inhibitor or IRAK4 degrader, the BCL-2 inhibitor, and the nucleoside analog are administered within about 5 minutes to within about 168 hours of each other.

In certain embodiments, the IRAK4 inhibitor, the BCL-2 inhibitor, and the nucleoside analog are administered simultaneously. In yet other embodiments, the IRAK4 inhibitor may be administered first, the BCL-2 inhibitor third, and the nucleoside analog second. In yet other embodiments, the IRAK4 inhibitor may be administered second, the BCL-2 inhibitor first, and the nucleoside analog third. In yet other embodiments, the IRAK4 inhibitor may be administered second, the BCL-2 inhibitor third, and the nucleoside analog first. In yet other embodiments, the IRAK4 inhibitor may be administered third, the BCL-2 inhibitor first, and the nucleoside analog second. In yet other embodiments, the IRAK4 inhibitor may be administered third, the BCL-2 inhibitor second, and the nucleoside analog first. In certain embodiments, the IRAK4 inhibitor, the BCL-2 inhibitor, and the nucleoside analog are administered within about 5 minutes to within about 168 hours of each other.

In certain embodiments, the IRAK4 inhibitor or IRAK4 degrader and the nucleoside analog are administered simultaneously. In other embodiments, the IRAK4 inhibitor and the nucleoside analog are administered within about 5 minutes to within about 168 hours of each other.

In certain embodiments, the IRAK4 inhibitor and the nucleoside analog are administered simultaneously. In other embodiments, the IRAK4 inhibitor and the nucleoside analog are administered within about 5 minutes to within about 168 hours of each other.

Pharmaceutical Compositions

The compositions and methods of the present disclosure may be utilized to treat an individual in need thereof. In certain embodiments, the individual is a mammal such as a human, or a non-human mammal. When administered to an animal, such as a human, the composition or the compound is preferably administered as a pharmaceutical composition comprising, for example, a compound of the invention and a pharmaceutically acceptable carrier. Pharmaceutically acceptable carriers are well known in the art and include, for example, aqueous solutions such as water or physiologically buffered saline or other solvents or vehicles such as glycols, glycerol, oils such as olive oil, or injectable organic esters. In preferred embodiments, when such pharmaceutical compositions are for human administration, particularly for invasive routes of administration (i.e., routes, such as injection or implantation, that circumvent transport or diffusion through an epithelial barrier), the aqueous solution is pyrogen-free, or substantially pyrogen-free. The excipients can be chosen, for example, to effect delayed release of an agent or to selectively target one or more cells, tissues or organs. The pharmaceutical composition can be in dosage unit form such as tablet, capsule (including sprinkle capsule and gelatin capsule), granule, lyophile for reconstitution, powder, solution, syrup, suppository, injection or the like. The composition can also be present in a transdermal delivery system, e.g., a skin patch. The composition can also be present in a solution suitable for topical administration, such as a lotion, cream, or ointment.

A pharmaceutically acceptable carrier can contain physiologically acceptable agents that act, for example, to stabilize, increase solubility or to increase the absorption of a compound such as a compound of the invention. Such physiologically acceptable agents include, for example, carbohydrates, such as glucose, sucrose or dextrans, antioxidants, such as ascorbic acid or glutathione, chelating agents, low molecular weight proteins or other stabilizers or excipients. The choice of a pharmaceutically acceptable carrier, including a physiologically acceptable agent, depends, for example, on the route of administration of the composition. The preparation or pharmaceutical composition can be a selfemulsifying drug delivery system or a selfmicroemulsifying drug delivery system. The pharmaceutical composition (preparation) also can be a liposome or other polymer matrix, which can have incorporated therein, for example, a compound of the invention. Liposomes, for example, which comprise phospholipids or other lipids, are nontoxic, physiologically acceptable and metabolizable carriers that are relatively simple to make and administer.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

A pharmaceutical composition (preparation) can be administered to a subject by any of a number of routes of administration including, for example, orally (for example, drenches as in aqueous or non-aqueous solutions or suspensions, tablets, capsules (including sprinkle capsules and gelatin capsules), boluses, powders, granules, pastes for application to the tongue); absorption through the oral mucosa (e.g., sublingually); subcutaneously; transdermally (for example as a patch applied to the skin); and topically (for example, as a cream, ointment or spray applied to the skin). The compound may also be formulated for inhalation. In certain embodiments, a compound may be simply dissolved or suspended in sterile water. Details of appropriate routes of administration and compositions suitable for same can be found in, for example, U.S. Pat. Nos. 6,110,973, 5,763,493, 5,731,000, 5,541,231, 5,427,798, 5,358,970 and 4,172,896, as well as in patents cited therein.

The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient that can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an active compound, such as a compound of the invention, with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules (including sprinkle capsules and gelatin capsules), cachets, pills, tablets, lozenges (using a flavored basis, usually sucrose and acacia or tragacanth), lyophile, powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. Compositions or compounds may also be administered as a bolus, electuary or paste.

To prepare solid dosage forms for oral administration (capsules (including sprinkle capsules and gelatin capsules), tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; (10) complexing agents, such as, modified and unmodified cyclodextrins; and (11) coloring agents. In the case of capsules (including sprinkle capsules and gelatin capsules), tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions, such as dragees, capsules (including sprinkle capsules and gelatin capsules), pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms useful for oral administration include pharmaceutically acceptable emulsions, lyophiles for reconstitution, microemulsions, solutions, suspensions, syrups and elixirs. In addition to the active ingredient, the liquid dosage forms may contain inert diluents commonly used in the art, such as, for example, water or other solvents, cyclodextrins and derivatives thereof, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Dosage forms for the topical or transdermal administration include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The ointments, pastes, creams and gels may contain, in addition to an active compound, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an active compound, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the active compound in the proper medium. Absorption enhancers can also be used to increase the flux of the compound across the skin. The rate of such flux can be controlled by either providing a rate controlling membrane or dispersing the compound in a polymer matrix or gel.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion. Pharmaceutical compositions suitable for parenteral administration comprise one or more active compounds in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle.

Injectable depot forms are made by forming microencapsulated matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissue.

For use in the methods of this invention, active compounds can be given per se or as a pharmaceutical composition containing, for example, 0.1 to 99.5% (more preferably, 0.5 to 90%) of active ingredient in combination with a pharmaceutically acceptable carrier.

Methods of introduction may also be provided by rechargeable or biodegradable devices. Various slow release polymeric devices have been developed and tested in vivo in recent years for the controlled delivery of drugs, including proteinaceous biopharmaceuticals. A variety of biocompatible polymers (including hydrogels), including both biodegradable and non-degradable polymers, can be used to form an implant for the sustained release of a compound at a particular target site.

Actual dosage levels of the active ingredients in the pharmaceutical compositions may be varied so as to obtain the active ingredient that is effective to achieve the desired therapeutic response for a particular patient, composition, and mode of administration, without being toxic to the patient.

The selected dosage level will depend upon a variety of factors including the activity of the particular compound or combination of compounds employed, or the ester, salt or amide thereof, the route of administration, the time of administration, the rate of excretion of the particular compound(s) being employed, the duration of the treatment, other drugs, compounds and/or materials used in combination with the particular compound(s) employed, the age, sex, weight, condition, general health and prior medical history of the patient being treated, and like factors well known in the medical arts.

A physician or veterinarian having ordinary skill in the art can readily determine and prescribe the therapeutically effective amount of the pharmaceutical composition required. For example, the physician or veterinarian could start doses of the pharmaceutical composition or compound at levels lower than that required in order to achieve the desired therapeutic effect and gradually increase the dosage until the desired effect is achieved. By "therapeutically effective amount" is meant the concentration of a compound that is sufficient to elicit the desired therapeutic effect. It is generally understood that the effective amount of the compound will vary according to the weight, sex, age, and medical history of the subject. Other factors which influence the effective amount may include, but are not limited to, the severity of the patient's condition, the disorder being treated, the stability of the compound, and, if desired, another type of therapeutic agent being administered with the compound of the invention. A larger total dose can be delivered by multiple administrations of the agent. Methods to determine efficacy and dosage are known to those skilled in the art (Isselbacher et al. (1996) Harrison's Principles of Internal Medicine 13 ed., 1814-1882, herein incorporated by reference).

In general, a suitable daily dose of an active compound used in the compositions and methods of the invention will be that amount of the compound that is the lowest dose effective to produce a therapeutic effect. Such an effective dose will generally depend upon the factors described above.

If desired, the effective daily dose of the active compound may be administered as one, two, three, four, five, six or more sub-doses administered separately at appropriate intervals throughout the day, optionally, in unit dosage forms. In certain embodiments of the present invention, the active compound may be administered two or three times daily. In preferred embodiments, the active compound will be administered once daily.

The patient receiving this treatment is any animal in need, including primates, in particular humans; and other mammals such as equines, cattle, swine, sheep, cats, and dogs; poultry; and pets in general.

In certain embodiments, compounds of the invention may be used alone or conjointly administered with another type of therapeutic agent.

The present disclosure includes the use of pharmaceutically acceptable salts of compounds of the invention in the compositions and methods of the present invention. In certain embodiments, contemplated salts of the invention include, but are not limited to, alkyl, dialkyl, trialkyl or tetra-alkyl ammonium salts. In certain embodiments, contemplated salts of the invention include, but are not limited to, L-arginine, benenthamine, benzathine, betaine, calcium hydroxide, choline, deanol, diethanolamine, diethylamine, 2-(diethylamino)ethanol, ethanolamine, ethylenediamine, N-methylglucamine, hydrabamine, 1H-imidazole, lithium, L-lysine, magnesium, 4-(2-hydroxyethyl)morpholine, piperazine, potassium, 1-(2-hydroxyethyl)pyrrolidine, sodium, triethanolamine, tromethamine, and zinc salts. In certain embodiments, contemplated salts of the invention include, but are not limited to, Na, Ca, K, Mg, Zn or other metal salts. In certain embodiments, contemplated salts of the invention include, but are not limited to, 1-hydroxy-2-naphthoic acid, 2,2-dichloroacetic acid, 2-hydroxyethanesulfonic acid, 2-oxoglutaric acid, 4-acetamidobenzoic acid, 4-aminosalicylic acid, acetic acid, adipic acid, 1-ascorbic acid, 1-aspartic acid, benzenesulfonic acid, benzoic acid, (+)-camphoric acid, (+)-camphor-10-sulfonic acid, capric acid (decanoic acid), caproic acid (hexanoic acid), caprylic acid (octanoic acid), carbonic acid, cinnamic acid, citric acid, cyclamic acid, dodecylsulfuric acid, ethane-1,2-disulfonic acid, ethanesulfonic acid, formic acid, fumaric acid, galactaric acid, gentisic acid, d-glucoheptonic acid, d-gluconic acid, d-glucuronic acid, glutamic acid, glutaric acid, glycerophosphoric acid, glycolic acid, hippuric acid, hydrobromic acid, hydrochloric acid, isobutyric acid, lactic acid, lactobionic acid, lauric acid, maleic acid, 1-malic acid, malonic acid, mandelic acid, methanesulfonic acid, naphthalene-1,5-disulfonic acid, naphthalene-2-sulfonic acid, nicotinic acid, nitric acid, oleic acid, oxalic acid, palmitic acid, pamoic acid, phosphoric acid, proprionic acid, 1-pyroglutamic acid, salicylic acid, sebacic acid, stearic acid, succinic acid, sulfuric acid, 1-tartaric acid, thiocyanic acid, p-toluenesulfonic acid, trifluoroacetic acid, and undecylenic acid acid salts.

The pharmaceutically acceptable acid addition salts can also exist as various solvates, such as with water, methanol, ethanol, dimethylformamide, and the like. Mixtures of such solvates can also be prepared. The source of such solvate can be from the solvent of crystallization, inherent in the solvent of preparation or crystallization, or adventitious to such solvent.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water-soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetraacetic acid (EDTA), sorbitol, tartaric acid, phosphoric acid, and the like.

Definitions

Unless otherwise defined herein, scientific and technical terms used in this application shall have the meanings that are commonly understood by those of ordinary skill in the art. Generally, nomenclature used in connection with, and techniques of, chemistry, cell and tissue culture, molecular biology, cell and cancer biology, neurobiology, neurochemistry, virology, immunology, microbiology, pharmacology, genetics and protein and nucleic acid chemistry, described herein, are those well known and commonly used in the art.

The methods and techniques of the present disclosure are generally performed, unless otherwise indicated, according to conventional methods well known in the art and as described in various general and more specific references that are cited and discussed throughout this specification. See, e.g. "Principles of Neural Science", McGraw-Hill Medical, New York, N.Y. (2000); Motulsky, "Intuitive Biostatistics", Oxford University Press, Inc. (1995); Lodish et al., "Molecular Cell Biology, 4th ed.", W. H. Freeman & Co., New York (2000); Griffiths et al., "Introduction to Genetic Analysis, 7th ed.", W. H. Freeman & Co., N.Y. (1999); and Gilbert et al., "Developmental Biology, 6th ed.", Sinauer Associates, Inc., Sunderland, MA (2000).

Chemistry terms used herein, unless otherwise defined herein, are used according to conventional usage in the art, as exemplified by "The McGraw-Hill Dictionary of Chemical Terms", Parker S., Ed., McGraw-Hill, San Francisco, C.A. (1985).

All of the above, and any other publications, patents and published patent applications referred to in this application are specifically incorporated by reference herein. In case of conflict, the present specification, including its specific definitions, will control.

The term "agent" is used herein to denote a chemical compound (such as an organic or inorganic compound, a mixture of chemical compounds), a biological macromolecule (such as a nucleic acid, an antibody, including parts thereof as well as humanized, chimeric and human antibodies and monoclonal antibodies, a protein or portion thereof, e.g., a peptide, a lipid, a carbohydrate), or an extract made from biological materials such as bacteria, plants, fungi, or animal (particularly mammalian) cells or tissues. Agents include, for example, agents whose structure is known, and those whose structure is not known. The ability of such agents to inhibit AR or promote AR degradation may render them suitable as "therapeutic agents" in the methods and compositions of this disclosure.

A "patient," "subject," or "individual" are used interchangeably and refer to either a human or a non-human animal. These terms include mammals, such as humans, primates, livestock animals (including bovines, porcines, etc.), companion animals (e.g., canines, felines, etc.) and rodents (e.g., mice and rats).

"Treating" a condition or patient refers to taking steps to obtain beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, and remission (whether partial or total), whether detectable or undetectable. "Treatment" can also mean prolonging survival as compared to expected survival if not receiving treatment.

The term "preventing" is art-recognized, and when used in relation to a condition, such as a local recurrence (e.g., pain), a disease such as cancer, a syndrome complex such as heart failure or any other medical condition, is well understood in the art, and includes administration of a composition which reduces the frequency of, or delays the onset of, symptoms of a medical condition in a subject relative to a subject which does not receive the composition. Thus, prevention of cancer includes, for example, reducing the number of detectable cancerous growths in a population of patients receiving a prophylactic treatment relative to an untreated control population, and/or delaying the appearance of detectable cancerous growths in a treated population versus an untreated control population, e.g., by a statistically and/or clinically significant amount.

"Administering" or "administration of" a substance, a compound or an agent to a subject can be carried out using one of a variety of methods known to those skilled in the art. For example, a compound or an agent can be administered, intravenously, arterially, intradermally, intramuscularly, intraperitoneally, subcutaneously, ocularly, sublingually, orally (by ingestion), intranasally (by inhalation), intraspinally, intracerebrally, and transdermally (by absorption, e.g., through a skin duct). A compound or agent can also appropriately be introduced by rechargeable or biodegradable polymeric devices or other devices, e.g., patches and pumps, or formulations, which provide for the extended, slow or controlled release of the compound or agent. Administering can also be performed, for example, once, a plurality of times, and/or over one or more extended periods.

Appropriate methods of administering a substance, a compound or an agent to a subject will also depend, for example, on the age and/or the physical condition of the subject and the chemical and biological properties of the compound or agent (e.g., solubility, digestibility, bioavailability, stability and toxicity). In certain embodiments, a compound or an agent is administered orally, e.g., to a subject by ingestion. In certain embodiments, the orally administered compound or agent is in an extended release or slow release formulation, or administered using a device for such slow or extended release.

As used herein, the phrase "conjoint administration" refers to any form of administration of two or more different therapeutic agents such that the second agent is administered while the previously administered therapeutic agent is still effective in the body (e.g., the two agents are simultaneously effective in the patient, which may include synergistic effects of the two agents). For example, the different therapeutic compounds can be administered either in the same formulation or in separate formulations, either concomitantly or sequentially. Thus, an individual who receives such treatment can benefit from a combined effect of different therapeutic agents.

A "therapeutically effective amount" or a "therapeutically effective dose" of a drug or agent is a drug or an agent that, when administered to a subject will have the intended therapeutic effect. The full therapeutic effect does not necessarily occur by administration of one dose, and may occur only after administration of a series of doses. Thus, a therapeutically effective amount may be administered in one or more administrations. The precise effective amount needed for a subject will depend upon, for example, the subject's size, health and age, and the nature and extent of the condition being treated, such as cancer or MDS. The skilled worker can readily determine the effective amount for a given situation by routine experimentation.

As used herein, the terms "optional" or "optionally" mean that the subsequently described event or circumstance may occur or may not occur, and that the description includes instances where the event or circumstance occurs as well as instances in which it does not. For example, "optionally substituted alkyl" refers to the alkyl may be substituted as well as where the alkyl is not substituted.

It is understood that substituents and substitution patterns on the compounds of the present invention can be selected by one of ordinary skilled person in the art to result chemically stable compounds which can be readily synthesized by techniques known in the art, as well as those methods set forth below, from readily available starting materials. If a substituent is itself substituted with more than one group, it is understood that these multiple groups may be on the same carbon or on different carbons, so long as a stable structure results.

As used herein, the term "optionally substituted" refers to the replacement of one to six hydrogen radicals in a given structure with the radical of a specified substituent including, but not limited to: hydroxyl, hydroxyalkyl, alkoxy, halogen, alkyl, nitro, silyl, acyl, acyloxy, aryl, cycloalkyl, heterocyclyl, amino, aminoalkyl, cyano, haloalkyl, haloalkoxy, —OCO—CH$_2$—O-alkyl, —OP(O)(O-alkyl)$_2$ or —CH$_2$—OP(O)(O-alkyl)$_2$. Preferably, "optionally substituted" refers to the replacement of one to four hydrogen radicals in a given structure with the substituents mentioned above. More preferably, one to three hydrogen radicals are replaced by the substituents as mentioned above. It is understood that the substituent can be further substituted.

As used herein, the term "alkyl" refers to saturated aliphatic groups, including but not limited to $C_1$-$C_{10}$ straight-chain alkyl groups or $C_1$-$C_{10}$ branched-chain alkyl groups. Preferably, the "alkyl" group refers to $C_1$-$C_6$ straight-chain alkyl groups or $C_1$-$C_6$ branched-chain alkyl groups. Most preferably, the "alkyl" group refers to $C_1$-$C_4$ straight-chain alkyl groups or $C_1$-$C_4$ branched-chain alkyl groups. Examples of "alkyl" include, but are not limited to, methyl, ethyl, 1-propyl, 2-propyl, n-butyl, sec-butyl, tert-butyl, 1-pentyl, 2-pentyl, 3-pentyl, neo-pentyl, 1-hexyl, 2-hexyl, 3-hexyl, 1-heptyl, 2-heptyl, 3-heptyl, 4-heptyl, 1-octyl, 2-octyl, 3-octyl or 4-octyl and the like. The "alkyl" group may be optionally substituted.

The term "acyl" is art-recognized and refers to a group represented by the general formula hydrocarbylC(O)—, preferably alkylC(O)—.

The term "acylamino" is art-recognized and refers to an amino group substituted with an acyl group and may be represented, for example, by the formula hydrocarbylC(O)NH—.

The term "acyloxy" is art-recognized and refers to a group represented by the general formula hydrocarbylC(O)O—, preferably alkylC(O)O—.

The term "alkoxy" refers to an alkyl group having an oxygen attached thereto. Representative alkoxy groups include methoxy, ethoxy, propoxy, tert-butoxy and the like.

The term "alkoxyalkyl" refers to an alkyl group substituted with an alkoxy group and may be represented by the general formula alkyl-O-alkyl.

The term "alkyl" refers to saturated aliphatic groups, including straight-chain alkyl groups, branched-chain alkyl groups, cycloalkyl (alicyclic) groups, alkyl-substituted cycloalkyl groups, and cycloalkyl-substituted alkyl groups.

In preferred embodiments, a straight chain or branched chain alkyl has 30 or fewer carbon atoms in its backbone (e.g., $C_{1-30}$ for straight chains, $C_{3-30}$ for branched chains), and more preferably 20 or fewer.

Moreover, the term "alkyl" as used throughout the specification, examples, and claims is intended to include both unsubstituted and substituted alkyl groups, the latter of which refers to alkyl moieties having substituents replacing a hydrogen on one or more carbons of the hydrocarbon backbone, including haloalkyl groups such as trifluoromethyl and 2,2,2-trifluoroethyl, etc.

The term "$C_{x-y}$" or "$C_x$-$C_y$", when used in conjunction with a chemical moiety, such as, acyl, acyloxy, alkyl, alkenyl, alkynyl, or alkoxy is meant to include groups that contain from x to y carbons in the chain. $C_0$alkyl indicates a hydrogen where the group is in a terminal position, a bond if internal. A $C_{1-6}$alkyl group, for example, contains from one to six carbon atoms in the chain.

The term "alkylamino", as used herein, refers to an amino group substituted with at least one alkyl group.

The term "alkylthio", as used herein, refers to a thiol group substituted with an alkyl group and may be represented by the general formula alkylS—.

The term "amide", as used herein, refers to a group

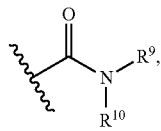

wherein $R^9$ and $R^{10}$ each independently represent a hydrogen or hydrocarbyl group, or $R^9$ and $R^{10}$ taken together with the N atom to which they are attached complete a heterocycle having from 4 to 8 atoms in the ring structure.

The terms "amine" and "amino" are art-recognized and refer to both unsubstituted and substituted amines and salts thereof, e.g., a moiety that can be represented by

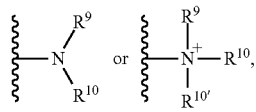

wherein $R^9$, $R^{10}$, and $R^{10'}$ each independently represent a hydrogen or a hydrocarbyl group, or $R^9$ and $R^{10}$ taken together with the N atom to which they are attached complete a heterocycle having from 4 to 8 atoms in the ring structure.

The term "aminoalkyl", as used herein, refers to an alkyl group substituted with an amino group.

The term "aralkyl", as used herein, refers to an alkyl group substituted with an aryl group.

The term "aryl" as used herein include substituted or unsubstituted single-ring aromatic groups in which each atom of the ring is carbon. Preferably the ring is a 5- to 7-membered ring, more preferably a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

The term "carbamate" is art-recognized and refers to a group

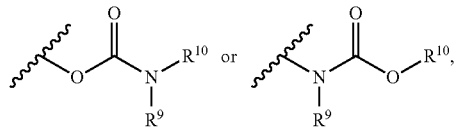

wherein $R^9$ and $R^{10}$ independently represent hydrogen or a hydrocarbyl group.

The term "carbocyclylalkyl", as used herein, refers to an alkyl group substituted with a carbocycle group.

The term "carbocycle" includes 5-7 membered monocyclic and 8-12 membered bicyclic rings. Each ring of a bicyclic carbocycle may be selected from saturated, unsaturated and aromatic rings. Carbocycle includes bicyclic molecules in which one, two or three or more atoms are shared between the two rings. The term "fused carbocycle" refers to a bicyclic carbocycle in which each of the rings shares two adjacent atoms with the other ring. Each ring of a fused carbocycle may be selected from saturated, unsaturated and aromatic rings. In an exemplary embodiment, an aromatic ring, e.g., phenyl, may be fused to a saturated or unsaturated ring, e.g., cyclohexane, cyclopentane, or cyclohexene. Any combination of saturated, unsaturated and aromatic bicyclic rings, as valence permits, is included in the definition of carbocyclic. Exemplary "carbocycles" include cyclopentane, cyclohexane, bicyclo[2.2.1]heptane, 1,5-cyclooctadiene, 1,2,3,4-tetrahydronaphthalene, bicyclo[4.2.0]oct-3-ene, naphthalene and adamantane. Exemplary fused carbocycles include decalin, naphthalene, 1,2,3,4-tetrahydronaphthalene, bicyclo[4.2.0]octane, 4,5,6,7-tetrahydro-1H-indene and bicyclo[4.1.0]hept-3-ene. "Carbocycles" may be substituted at any one or more positions capable of bearing a hydrogen atom.

The term "carbocyclylalkyl", as used herein, refers to an alkyl group substituted with a carbocycle group.

The term "carbonate" is art-recognized and refers to a group —$OCO_2$—.

The term "carboxy", as used herein, refers to a group represented by the formula —$CO_2H$.

The term "cycloalkyl" includes substituted or unsubstituted non-aromatic single ring structures, preferably 4- to 8-membered rings, more preferably 4- to 6-membered rings. The term "cycloalkyl" also includes polycyclic ring systems having two or more cyclic rings in which two or more carbons are common to two adjoining rings wherein at least one of the rings is cycloalkyl and the substituent (e.g., $R^{1000}$) is attached to the cycloalkyl ring, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, pyrazole, pyridine, pyrazine, pyridazine, pyrimidine, denzodioxane, tetrahydroquinoline, and the like.

The term "ester", as used herein, refers to a group —$C(O)OR^9$ wherein $R^9$ represents a hydrocarbyl group.

The term "ether", as used herein, refers to a hydrocarbyl group linked through an oxygen to another hydrocarbyl group. Accordingly, an ether substituent of a hydrocarbyl group may be hydrocarbyl-O—. Ethers may be either symmetrical or unsymmetrical. Examples of ethers include, but are not limited to, heterocycle-O-heterocycle and aryl-O- heterocycle. Ethers include "alkoxyalkyl" groups, which may be represented by the general formula alkyl-O-alkyl.

The terms "halo" and "halogen" as used herein means halogen and includes chloro, fluoro, bromo, and iodo.

The terms "heteroalkyl" and "heteroaralkyl", as used herein, refers to an alkyl group substituted with a hetaryl group.

The terms "heteroaryl" and "hetaryl" include substituted or unsubstituted aromatic single ring structures, preferably 5- to 7-membered rings, more preferably 5- to 6-membered rings, whose ring structures include at least one heteroatom, preferably one to four heteroatoms, more preferably one or two heteroatoms. The terms "heteroaryl" and "hetaryl" also include polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, pyrazole, pyridine, pyrazine, pyridazine, and pyrimidine, and the like.

The term "heteroatom" as used herein means an atom of any element other than carbon or hydrogen. Preferred heteroatoms are nitrogen, oxygen, and sulfur.

The term "heterocyclylalkyl", as used herein, refers to an alkyl group substituted with a heterocycle group.

The terms "heterocyclyl", "heterocycle", and "heterocyclic" refer to substituted or unsubstituted non-aromatic ring structures, preferably 3- to 10-membered rings, more preferably 3- to 7-membered rings, whose ring structures include at least one heteroatom, preferably one to four heteroatoms, more preferably one or two heteroatoms. The terms "heterocyclyl" and "heterocyclic" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, morpholine, lactones, lactams, and the like.

The term "hydrocarbyl", as used herein, refers to a group that is bonded through a carbon atom that does not have a =O or =S substituent, and typically has at least one carbon-hydrogen bond and a primarily carbon backbone, but may optionally include heteroatoms. Thus, groups like methyl, ethoxyethyl, 2-pyridyl, and even trifluoromethyl are considered to be hydrocarbyl for the purposes of this application, but substituents such as acetyl (which has a =O substituent on the linking carbon) and ethoxy (which is linked through oxygen, not carbon) are not. Hydrocarbyl groups include, but are not limited to aryl, heteroaryl, carbocycle, heterocycle, alkyl, alkenyl, alkynyl, and combinations thereof.

The term "hydroxyalkyl", as used herein, refers to an alkyl group substituted with a hydroxy group.

The term "lower" when used in conjunction with a chemical moiety, such as, acyl, acyloxy, alkyl, alkenyl, alkynyl, or alkoxy is meant to include groups where there are ten or fewer atoms in the substituent, preferably six or fewer. A "lower alkyl", for example, refers to an alkyl group that contains ten or fewer carbon atoms, preferably six or fewer. In certain embodiments, acyl, acyloxy, alkyl, alkenyl, alkynyl, or alkoxy substituents defined herein are respectively lower acyl, lower acyloxy, lower alkyl, lower alkenyl, lower alkynyl, or lower alkoxy, whether they appear alone or in combination with other substituents, such as in the recitations hydroxyalkyl and aralkyl (in which case, for example, the atoms within the aryl group are not counted when counting the carbon atoms in the alkyl substituent).

The terms "polycyclyl", "polycycle", and "polycyclic" refer to two or more rings (e.g., cycloalkyls, cycloalkenyls, cycloalkynyls, aryls, heteroaryls, and/or heterocyclyls) in which two or more atoms are common to two adjoining rings, e.g., the rings are "fused rings". Each of the rings of the polycycle can be substituted or unsubstituted. In certain embodiments, each ring of the polycycle contains from 3 to 10 atoms in the ring, preferably from 5 to 7.

The term "sulfate" is art-recognized and refers to the group —OSO$_3$H, or a pharmaceutically acceptable salt thereof.

The term "sulfonamide" is art-recognized and refers to the group represented by the general formulae

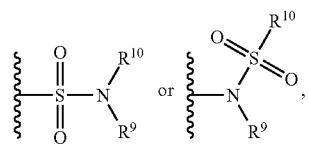

wherein $R^9$ and $R^{10}$ independently represents hydrogen or hydrocarbyl.

The term "sulfoxide" is art-recognized and refers to the group —S(O)—.

The term "sulfonate" is art-recognized and refers to the group SO$_3$H, or a pharmaceutically acceptable salt thereof.

The term "sulfone" is art-recognized and refers to the group —S(O)$_2$—.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate.

The term "thioalkyl", as used herein, refers to an alkyl group substituted with a thiol group.

The term "thioester", as used herein, refers to a group —C(O)SR⁹ or —SC(O)R⁹
wherein R⁹ represents a hydrocarbyl.

The term "thioether", as used herein, is equivalent to an ether, wherein the oxygen is replaced with a sulfur.

The term "urea" is art-recognized and may be represented by the general formula

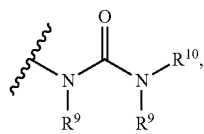

wherein R⁹ and R¹⁰ independently represent hydrogen or a hydrocarbyl.

The term "modulate" as used herein includes the inhibition or suppression of a function or activity (such as cell proliferation) as well as the enhancement of a function or activity.

The phrase "pharmaceutically acceptable" is art-recognized. In certain embodiments, the term includes compositions, excipients, adjuvants, polymers and other materials and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable salt" or "salt" is used herein to refer to an acid addition salt or a basic addition salt which is suitable for or compatible with the treatment of patients.

The term "pharmaceutically acceptable acid addition salt" as used herein means any non-toxic organic or inorganic salt of any base compounds represented by Formula I. Illustrative inorganic acids which form suitable salts include hydrochloric, hydrobromic, sulfuric and phosphoric acids, as well as metal salts such as sodium monohydrogen orthophosphate and potassium hydrogen sulfate. Illustrative organic acids that form suitable salts include mono-, di-, and tricarboxylic acids such as glycolic, lactic, pyruvic, malonic, succinic, glutaric, fumaric, malic, tartaric, citric, ascorbic, maleic, benzoic, phenylacetic, cinnamic and salicylic acids, as well as sulfonic acids such as p-toluene sulfonic and methanesulfonic acids. Either the mono or di-acid salts can be formed, and such salts may exist in either a hydrated, solvated or substantially anhydrous form. In general, the acid addition salts of compounds of Formula I are more soluble in water and various hydrophilic organic solvents, and generally demonstrate higher melting points in comparison to their free base forms. The selection of the appropriate salt will be known to one skilled in the art. Other non-pharmaceutically acceptable salts, e.g., oxalates, may be used, for example, in the isolation of compounds of Formula I for laboratory use, or for subsequent conversion to a pharmaceutically acceptable acid addition salt.

The term "pharmaceutically acceptable basic addition salt" as used herein means any non-toxic organic or inorganic base addition salt of any acid compounds represented by Formula I or any of their intermediates. Illustrative inorganic bases which form suitable salts include lithium, sodium, potassium, calcium, magnesium, or barium hydroxide. Illustrative organic bases which form suitable salts include aliphatic, alicyclic, or aromatic organic amines such as methylamine, trimethylamine and picoline or ammonia. The selection of the appropriate salt will be known to a person skilled in the art.

Many of the compounds useful in the methods and compositions of this disclosure have at least one stereogenic center in their structure. This stereogenic center may be present in a R or a S configuration, said R and S notation is used in correspondence with the rules described in Pure Appl. Chem. (1976), 45, 11-30. The disclosure contemplates all stereoisomeric forms such as enantiomeric and diastereoisomeric forms of the compounds, salts, prodrugs or mixtures thereof (including all possible mixtures of stereoisomers). See, e.g., WO 01/062726.

Furthermore, certain compounds which contain alkenyl groups may exist as Z (zusammen) or E (entgegen) isomers. In each instance, the disclosure includes both mixture and separate individual isomers.

Some of the compounds may also exist in tautomeric forms. Such forms, although not explicitly indicated in the formulae described herein, are intended to be included within the scope of the present disclosure.

"Prodrug" or "pharmaceutically acceptable prodrug" refers to a compound that is metabolized, for example hydrolyzed or oxidized, in the host after administration to form the compound of the present disclosure (e.g., compounds of formula I). Typical examples of prodrugs include compounds that have biologically labile or cleavable (protecting) groups on a functional moiety of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, or dephosphorylated to produce the active compound. Examples of prodrugs using ester or phosphoramidate as biologically labile or cleavable (protecting) groups are disclosed in U.S. Pat. Nos. 6,875,751, 7,585,851, and 7,964,580, the disclosures of which are incorporated herein by reference. The prodrugs of this disclosure are metabolized to produce a compound of Formula I. The present disclosure includes within its scope, prodrugs of the compounds described herein. Conventional procedures for the selection and preparation of suitable prodrugs are described, for example, in "Design of Prodrugs" Ed. H. Bundgaard, Elsevier, 1985.

The phrase "pharmaceutically acceptable carrier" as used herein means a pharmaceutically acceptable material, composition or vehicle, such as a liquid or solid filter, diluent, excipient, solvent or encapsulating material useful for formulating a drug for medicinal or therapeutic use.

The term "Log of solubility", "Log S" or "log S" as used herein is used in the art to quantify the aqueous solubility of a compound. The aqueous solubility of a compound significantly affects its absorption and distribution characteristics. A low solubility often goes along with a poor absorption. Log S value is a unit stripped logarithm (base 10) of the solubility measured in mol/liter.

The term "partial response" as used herein means an objective response in at least one organ or tissue in the subject with no evidence of progression elsewhere. For example, a partial response may refer to a 50% or more reduction in the disease state (e.g., tumor volume).

The term "complete response" as used herein means a complete disappearance of the measurable evidence of the disease in the subject. For example, in certain embodiments a complete response may refer to the complete measurable disappearance of the subject's cancer. In other embodiments, a complete response may refer to the complete measurable disappearance of the subject's symptoms (e.g., the subject's cytokine count may return to normal).

The term "Compound 1" refers to

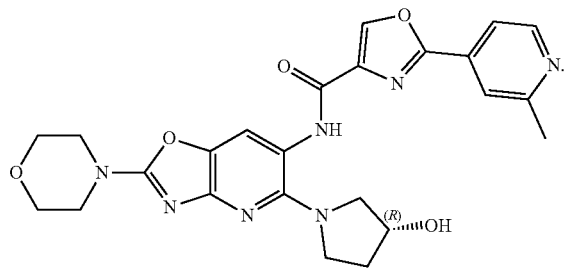

EXAMPLES

The invention now being generally described, it will be more readily understood by reference to the following examples which are included merely for purposes of illustration of certain aspects and embodiments of the present invention, and are not intended to limit the invention.

Example 1: Exemplary Treatment of Cancer with a Combination of an IRAK-4 Inhibitor, a Bcl-2 Inhibitor, and a Nucleoside Analog

Materials and Methods

CellTiter Glo cell viability assay was used to evaluate the antitumor effects of Compound 1 in combination with AML SOC drugs daunorubicin, Ara-C, decitabine, azacitidine and venetoclax in FLT3-WT AML cell lines THP-1, F-36P, OCl-AML2 and GDM-1. $GI_{50}$ (the concentration for 50% of maximal inhibition of cell proliferation) was determined for each drug in AML cell lines. Either $GI_{50}$ (below peak plasma concentration) or peak plasma concentration (if $GI_{50}$ was higher than peak plasma concentration) of each drug was used as clinically relevant concentration for combination experiments.

Results

We identified THP-1 and F-36P cell lines as resistant to clinically relevant concentrations of venetoclax, whereas OCl-AML2 cell line was resistant to the treatment with azacytidine (Table 1). Synergistic effect of combining Compound 1 with Ara-C was observed in THP-1 cell line. We found that Compound 1 potentiated antitumor effects of azacitidine in 3 of 4 FLT3-WT AML cell lines whereas we did not observe any additive or synergistic effect of combining Compound 1 with decitabine (Table 2). The combination of venetoclax and Compound 1 inhibited the cell growth in 2 of 4 AML FLT3-WT cell lines more effectively than either of the two agents alone. Moreover, we found that Compound 1 significantly potentiated antitumor effects of azacitidine+venetoclax in all AML FLT3-WT cell lines (Table 2).

TABLE 1

| GI50 (μM) for Compound 1 and AML Standard of Care Drugs | | | | | | |
|---|---|---|---|---|---|---|
| AML cell line | Compound 1 (μM) | Decitabine | Azacitidine | Ara-C | Daunorubicin | Venetoclax |
| THP-1 | >20 | 0.15 | 3 | 0.15 | 0.005 | 18 |
| F-36P | >20 | 0.20 | 4 | 0.15 | 0.1 | 18 |
| OCl-AML2 | 13 | 18 | 30 | 4 | 0.005 | 0.002 |
| GDM-1 | >20 | 0.08 | 2 | 0.005 | 0.01 | 0.005 |

Cells were treated for 72 hrs. Relative cell viability was measured by CellTiter Glo assay (Promega, Madison, WI) at 0 and at 72 hrs. $GI_{50}$ was calculated using GraphPad Prism 8.0 software.

TABLE 2

| Exemplary Combination Therapies | | | | | |
|---|---|---|---|---|---|
| AML cell line | Decitabine + Compound 1 | Azacitidine + Compound 1 | Venetoclax + Compound 1 | Venetoclax + Decitabine + Compound 1 | Venetoclax + Azacitidine + Compound 1 |
| THP-1 | NS | ++ | + | NS | +++ |
| F-36P | NS | ++ | NS | NS | ++ |
| OCl-AML2 | NS | + | ++ | ND | +++ |
| GDM-1 | NS | ++ | NS | NS | ++ |

| AML cell line | Ara-C + Compound 1 | Venetoclax + Ara-C + Compound 1 | Daunorubicin + Compound 1 | Daunorubicin + Ara-C + Compound 1 | |
|---|---|---|---|---|---|
| THP-1 | + | ++ | NS | ++ | — |
| F-36P | ++ | NS | NS | NS | — |
| OCl-AML2 | NS | ND | +++ | ND | — |
| GDM-1 | NS | NS | NS | NS | — |

Cells were treated continuously with clinically relevant drug concentration for 96 hrs. Relative cell viability was measured by CellTiter Glo assay (Promega, Madison, WI) at 0 and at 96 hrs according to manufacturer's instructions. All values are presented as mean±SE. Cell viability assay data were analyzed with one-way ANOVA. P values less than 0.05 were considered significant. Statistical analysis was performed using GraphPad Prism 8.0 software. + Less than 50% growth inhibition, p<0.05; ++ 50-100% growth inhibition, p<0.05; +++ Induction of cell death (cytotoxic effect), p<0.05; NS, not significant; ND, not defined. *Venetoclax resistant cell line, **Azacitidine/Decitabine resistant cell line. Clinically relevant conc (peak plasma conc): Compound 1-10 µM; Venetoclax—1 µM; and Azacitidine—4 µM.

Summary

These exemplary results demonstrate that combination of Compound 1, azacitidine and venetoclax exhibits synergistic activity in FLT3-WT leukemia cells providing a rationale for clinical testing of this combination in FLT3-WT AML patients.

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

We claim:
1. A method of treating cancer in a subject, comprising conjointly administering to a subject in need thereof a pyrimidinyl nucleoside analog, a BCL-2 inhibitor and an IRAK4 inhibitor with a structure represented by formula (II):

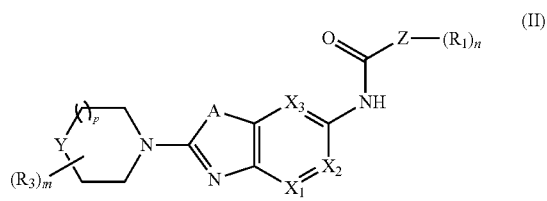

or a pharmaceutically acceptable salt thereof;
wherein
$X_1$ and $X_3$ independently are CH or N; $X_2$ is $CR_2$ or N; provided one and not more than one of $X_1$, $X_2$ or $X_3$ is N;
A is O or S;
Y is —CH$_2$— or O;
Z is aryl or heterocyclyl;
$R_1$, at each occurrence, is independently halo or optionally substituted heterocyclyl; wherein the substituent is alkyl, alkoxy, aminoalkyl, halo, hydroxyl, hydroxyalkyl or —NR$_a$R$_b$;
$R_2$ is hydrogen, optionally substituted cycloalkyl, optionally substituted aryl, optionally substituted heterocyclyl or —NR$_a$R$_b$; wherein the substituent is alkyl, amino, halo or hydroxyl;
$R_3$, at each occurrence, is alkyl or hydroxyl;
$R_a$ and $R_b$ are independently hydrogen, alkyl, acyl or heterocyclyl;
'm' and 'n' are independently 0, 1 or 2;
'p' is 0 or 1.
2. The method of claim 1, wherein
A is O or S;
Y is —CH$_2$— or O;
Z is aryl or heterocyclyl;
$R_1$, at each occurrence, is independently halo or optionally substituted heterocyclyl, wherein the substituent is alkyl, aminoalkyl, halo, or —NR$_a$R$_b$; where $R_a$ and $R_b$ are independently hydrogen, alkyl, or heterocyclyl;
$R_2$ is hydrogen, cycloalkyl, heterocyclyl or —NR$_a$R$_b$;
'm' is 0; and
'n' is 1.
3. The method of claim 1, wherein
A is O or S;
Y is —CH$_2$— or O;
Z is aryl or heterocyclyl;
$R_1$, at each occurrence, is independently halo or optionally substituted heterocyclyl; wherein the substituent is alkyl, alkoxy, aminoalkyl, halo, hydroxyl or —NR$_a$R$_b$; where $R_a$ and $R_b$ are independently hydrogen, alkyl, or heterocyclyl;
$R_2$ is hydrogen, cycloalkyl, optionally substituted heterocyclyl or —NR$_a$R$_b$, where the substituent is selected from amino, halo or hydroxyl;
'm' and 'n' are independently 0, 1 or 2; and
'p' is 0 or 1.
4. The method of claim 1, wherein the moiety

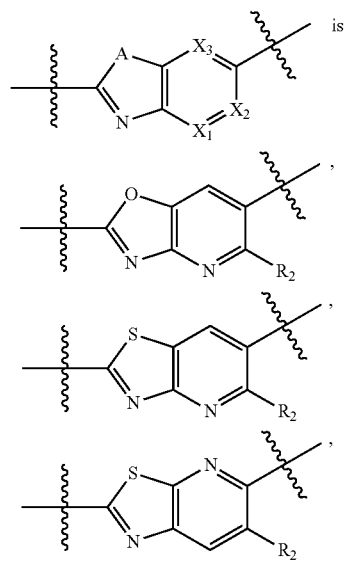

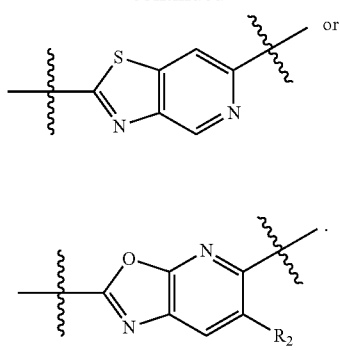

5. The method of claim 1, wherein Z is an optionally substituted heterocyclyl selected from phenyl, furanyl, thienyl, pyrrolyl, pyrazolyl, imidazolyl, oxazolyl, isoxazolyl, thiazolyl, isothiazolyl, 1H-tetrazolyl, oxadiazolyl, triazolyl, pyridyl, pyrimidinyl, pyrazinyl, pyridazinyl, azetidinyl, oxetanyl, imidazolidinyl, pyrrolidinyl, oxazolidinyl, thiazolidinyl, pyrazolidinyl, tetrahydrofuranyl, piperidinyl, piperazinyl, tetrahydropyranyl, morpholinyl, thiomorpholinyl, 1,4-dioxanyl, dioxidothiomorpholinyl, oxapiperazinyl, oxapiperidinyl, tetrahydrofuryl, tetrahydropyranyl, tetrahydrothiophenyl, dihydropyranyl and azabicyclo[3.2.1]octanyl; each of which is optionally substituted with alkyl, alkoxy, halo, hydroxyl, hydroxyalkyl or —NR$_a$R$_b$; and R$_a$ and R$_b$ are independently hydrogen, alkyl or acyl.

6. The method of claim 1, wherein the compound has a structure represented by formula (IIA):

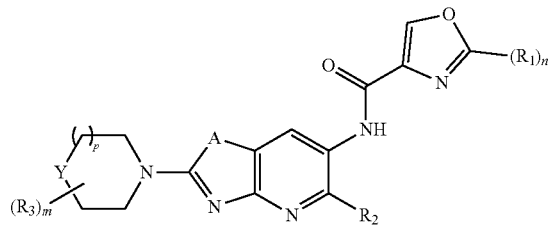

or a pharmaceutically acceptable salt thereof.

7. The method of claim 6, wherein

A is O or S;

Y is —CH$_2$— or O;

R$_1$, at each occurrence, is independently halo or optionally substituted heterocyclyl; wherein the substituent is alkyl, alkoxy, aminoalkyl, halo, hydroxyl or —NR$_a$R$_b$; where R$_a$ and R$_b$ are independently hydrogen, alkyl, or heterocyclyl;

R$_2$ is hydrogen, cycloalkyl, optionally substituted heterocyclyl or —NR$_a$R$_b$; wherein the optional substituent is selected from amino, halo or hydroxyl; and 'm' and 'n' are independently 0, 1 or 2.

8. The method of claim 1, wherein the compound has a structure represented by formula (IIB):

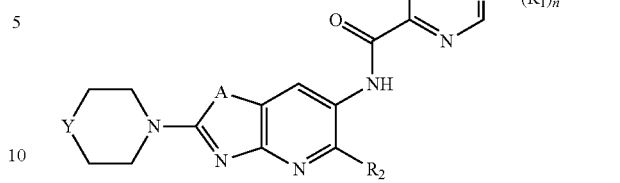

or a pharmaceutically acceptable salt thereof.

9. The method of claim 8, wherein

A is O or S;

Y is —CH$_2$— or O;

R$_1$, at each occurrence, is independently halo or optionally substituted heterocyclyl; wherein the substituent is alkyl, alkoxy, aminoalkyl, halo, hydroxyl or —NR$_a$R$_b$; where R$_a$ and R$_b$ are independently hydrogen, alkyl, or heterocyclyl;

R$_2$ is hydrogen, cycloalkyl, optionally substituted heterocyclyl or —NR$_a$R$_b$, where the optional substituent is selected from amino, halo or hydroxyl; and 'm' and 'n' are independently 0, 1 or 2.

10. The method of claim 1, wherein the compound has a structure represented by formula (IIC)

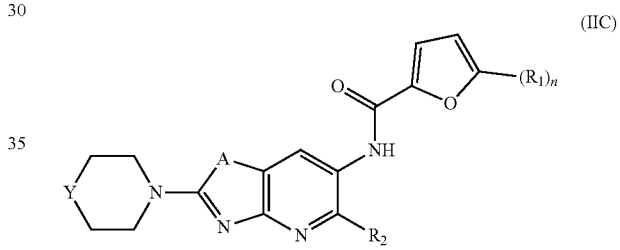

or a pharmaceutically acceptable salt thereof.

11. The method of claim 1, wherein R$_1$ is optionally substituted heterocyclyl;

wherein the substituent is alkyl, alkoxy, aminoalkyl, halo, hydroxyl, hydroxyalkyl or —NR$_a$R$_b$; and R$_a$ and R$_b$ are independently hydrogen, acyl, or heterocyclyl.

12. The method of claim 11, wherein R$_1$ is pyridyl, pyrazolyl, pyrrolidinyl or piperidinyl.

13. The method of claim 11, wherein R$_1$ is optionally substituted pyrazolyl, wherein the substituent is alkyl, hydroxyl or —NR$_a$R$_b$.

14. The method of claim 1, wherein R$_1$ is halo.

15. The method of claim 1, wherein R$_2$ is hydrogen, cycloalkyl, optionally substituted heterocyclyl or —NR$_a$R$_b$, where the substituent is selected from amino, halo or hydroxyl.

16. The method of claim 1, wherein R$_2$ is optionally substituted heterocyclyl selected from piperidinyl, pyrrolidinyl, morpholinyl, piperazinyl, azetidinyl, pyrazolyl, furanyl or azabicyclo[3.2.1]octanyl; wherein the substituent is hydroxyl, halo, alkyl or amino.

17. The method of claim 1, wherein R$_2$ is piperidinyl, pyrrolidinyl, morpholinyl, or piperazinyl.

18. The method of claim 1, wherein R$_2$ is hydrogen.

19. The method of claim 1, wherein R$_2$ is cycloalkyl.

20. The method of claim 19, wherein R$_2$ is cyclopropyl.

21. The method of claim 1, wherein R₃ is alkyl.

22. The method of claim 1, wherein m is 0 and p is 1.

23. The method of claim 1, wherein the compound of formula (II) is selected from:

6'-amino-N-(2-morpholinooxazolo[4,5-b]pyridin-6-yl)-[2,3'-bipyridine]-6-carboxamide;
6'-amino-N-(5-cyclopropyl-2-morpholinooxazolo[4,5-b]pyridin-6-yl)-[2,3'-bipyridine]-6-carboxamide hydrochloride;
N-(5-cyclopropyl-2-morpholinooxazolo[4,5-b]pyridin-6-yl)-2-(2-methylpyridin-4-yl)oxazole-4-carboxamide hydrochloride;
N-(2,5-di(piperidin-1-yl)oxazolo[4,5-b]pyridin-6-yl)-6-(1H-pyrazol-4-yl)picolinamide hydrochloride;
N-(2,5-di(piperidin-1-yl)oxazolo[4,5-b]pyridin-6-yl)-2-(2-methylpyridin-4-yl)oxazole-4-carboxamide;
N-(2-morpholino-5-(piperidin-1-yl)oxazolo[4,5-b]pyridin-6-yl)-6-(1H-pyrazol-4-yl)picolinamide;
2-(2-methylpyridin-4-yl)-N-(2-morpholino-5-(piperidin-1-yl)oxazolo[4,5-b]pyridin-6-yl)oxazole-4-carboxamide;
6-chloro-N-(2-morpholino-5-(piperidin-1-yl)oxazolo[4,5-b]pyridin-6-yl)picolinamide;
N-(2,5-di(piperidin-1-yl)oxazolo[4,5-b]pyridin-6-yl)-6-(1-methyl-1H-pyrazol-4-yl)picolinamide;
2-(2-chloropyridin-4-yl)-N-(2,5-di(piperidin-1-yl)oxazolo[4,5-b]pyridin-6-yl)oxazole-4-carboxamide;
(S)-2-(2-methylpyridin-4-yl)-N-(2-morpholino-5-(pyrrolidin-3-ylamino)oxazolo[4,5-b]pyridin-6-yl)oxazole-4-carboxamide;
6'-amino-N-(2-morpholinooxazolo[5,4-b]pyridin-5-yl)-[2,3'-bipyridine]-6-carboxamide;
6'-amino-N-(2-morpholinothiazolo[4,5-c]pyridin-6-yl)-[2,3'-bipyridine]-6-carboxamide;
6'-amino-N-(2-morpholinothiazolo[5,4-b]pyridin-5-yl)-[2,3'-bipyridine]-6-carboxamide;
2-(2-methylpyridin-4-yl)-N-(2-morpholinothiazolo[4,5-b]pyridin-6-yl)oxazole-4-carboxamide;
6'-amino-N-(2-morpholinothiazolo[4,5-b]pyridin-6-yl)-[2,3'-bipyridine]-6-carboxamide;
N-(2-morpholinothiazolo[4,5-b]pyridin-6-yl)-6-(1H-pyrazol-4-yl)picolinamide;
3-(4-(aminomethyl)piperidin-1-yl)-5-fluoro-N-(2-morpholinothiazolo[4,5-b]pyridin-6-yl)benzamide;
2-(4-(aminomethyl)piperidin-1-yl)-5-fluoro-N-(2-morpholinothiazolo[4,5-b]pyridin-6-yl)benzamide;
2-(2-methylpyridin-4-yl)-N-(2-morpholino-5-(piperidin-1-yl)thiazolo[4,5-b]pyridin-6-yl)oxazole-4-carboxamide;
N-(2-morpholino-5-(piperidin-1-yl)thiazolo[4,5-b]pyridin-6-yl)-6-(1H-pyrazol-4-yl)picolinamide;
N-(2,5-di(piperidin-1-yl)thiazolo[4,5-b]pyridin-6-yl)-6-(1H-pyrazol-4-yl)picolinamide;
N-(2,5-di(piperidin-1-yl)thiazolo[4,5-b]pyridin-6-yl)-2-(2-methylpyridin-4-yl)oxazole-4-carboxamide;
N-(2,5-dimorpholinooxazolo[4,5-b]pyridin-6-yl)-2-(2-methylpyridin-4-yl)oxazole-4-carboxamide;
N-(5-(4-methylpiperazin-1-yl)-2-morpholinooxazolo[4,5-b]pyridin-6-yl)-2-(2-methylpyridin-4-yl)oxazole-4-carboxamide;
N-(2,5-di(piperidin-1-yl)oxazolo[4,5-b]pyridin-6-yl)-2-(6-methoxypyridin-3-yl)oxazole-4-carboxamide;
N-(2,5-di(piperidin-1-yl)oxazolo[4,5-b]pyridin-6-yl)-2-(2-methylpyridin-3-yl)oxazole-4-carboxamide;
N-(2,5-di(piperidin-1-yl)oxazolo[4,5-b]pyridin-6-yl)-2-(2-hydroxypyridin-3-yl)oxazole-4-carboxamide;
2-(2-hydroxypyridin-3-yl)-N-(2-morpholino-5-(piperidin-1-yl)oxazolo[4,5-b]pyridin-6-yl)oxazole-4-carboxamide;
N-(2,5-di(piperidin-1-yl)oxazolo[4,5-b]pyridin-6-yl)-2-(6-hydroxypyridin-3-yl)oxazole-4-carboxamide;
2-(2-methoxypyridin-4-yl)-N-(2-morpholino-5-(piperidin-1-yl)oxazolo[4,5-b]pyridin-6-yl)oxazole-4-carboxamide;
2-(2-methylpyridin-3-yl)-N-(2-morpholino-5-(piperidin-1-yl)oxazolo[4,5-b]pyridin-6-yl)oxazole-4-carboxamide;
2-(3-methylpyridin-4-yl)-N-(2-morpholino-5-(piperidin-1-yl)oxazolo[4,5-b]pyridin-6-yl)oxazole-4-carboxamide;
N-(2,5-di(piperidin-1-yl)oxazolo[4,5-b]pyridin-6-yl)-2-(3-methylpyridin-4-yl)oxazole-4-carboxamide;
2-(6-methylpyridin-3-yl)-N-(2-morpholino-5-(piperidin-1-yl)oxazolo[4,5-b]pyridin-6-yl)oxazole-4-carboxamide;
6-(1-methyl-1H-pyrazol-4-yl)-N-(2-morpholino-5-(piperidin-1-yl)oxazolo[4,5-b]pyridin-6-yl)picolinamide;
N-(2,5-di(piperidin-1-yl)oxazolo[4,5-b]pyridin-6-yl)-2-(6-methylpyridin-3-yl)oxazole-4-carboxamide;
(S)-N-(5-(3-aminopyrrolidin-1-yl)-2-morpholinooxazolo[4,5-b]pyridin-6-yl)-2-(2-methylpyridin-4-yl)oxazole-4-carboxamide;
(S)-N-(5-(3-hydroxypyrrolidin-1-yl)-2-morpholinooxazolo[4,5-b]pyridin-6-yl)-2-(2-methylpyridin-4-yl)oxazole-4-carboxamide;

(R)-N-(5-(3-aminopyrrolidin-1-yl)-2-morpholinooxazolo[4,5-b]pyridin-6-yl)-2-(2-methylpyridin-4-yl)oxazole-4-carboxamide;
(R)-N-(5-(3-hydroxypyrrolidin-1-yl)-2-morpholinooxazolo[4,5-b]pyridin-6-yl)-2-(2-methylpyridin-4-yl)oxazole-4-carboxamide;
(S)-2-(3-aminopyrrolidin-1-yl)-N-(2-morpholino-5-(piperidin-1-yl)oxazolo[4,5-b]pyridin-6-yl)oxazole-4-carboxamide;
(S)-6-(3-hydroxypyrrolidin-1-yl)-N-(2-morpholino-5-(piperidin-1-yl)oxazolo[4,5-b]pyridin-6-yl)picolinamide;
(S)-6-(3-aminopyrrolidin-1-yl)-N-(2-morpholino-5-(piperidin-1-yl)oxazolo[4,5-b]pyridin-6-yl)picolinamide;
(S)-2-(3-hydroxypyrrolidin-1-yl)-N-(2-morpholino-5-(piperidin-1-yl)oxazolo[4,5-b]pyridin-6-yl)oxazole-4-carboxamide;
(S)-N-(5-cyclopropyl-2-morpholinooxazolo[4,5-b]pyridin-6-yl)-2-(3-hydroxypyrrolidin-1-yl)oxazole-4-carboxamide;
(S)-2-(3-aminopyrrolidin-1-yl)-N-(5-cyclopropyl-2-morpholinooxazolo[4,5-b]pyridin-6-yl)oxazole-4-carboxamide;
2-(2-methylpyridin-4-yl)-N-(5-(piperidin-1-yl)-2-(pyrrolidin-1-yl)oxazolo[4,5-b]pyridin-6-yl)oxazole-4-carboxamide hydrochloride;
N-(2-(2,6-dimethylmorpholino)-5-(piperidin-1-yl)oxazolo[4,5-b]pyridin-6-yl)-2-(2-methylpyridin-4-yl)oxazole-4-carboxamide hydrochloride;
N-(2,5-di(piperidin-1-yl)thiazolo[4,5-b]pyridin-6-yl)-6-(1-methyl-1H-pyrazol-4-yl)picolinamide hydrochloride;
6-(1-methyl-1H-pyrazol-4-yl)-N-(2-morpholino-5-(piperidin-1-yl)thiazolo[4,5-b]pyridin-6-yl)picolinamide;
N-(2,5-di(piperidin-1-yl)thiazolo[4,5-b]pyridin-6-yl)-2-(2-methylpyridin-3-yl)oxazole-4-carboxamide hydrochloride;
N-(2-((2S,6R)-2,6-dimethylmorpholino)-5-(piperidin-1-yl)thiazolo[4,5-b]pyridin-6-yl)-2-(2-methylpyridin-4-yl)oxazole-4-carboxamide;
2-(2-methylpyridin-3-yl)-N-(2-morpholino-5-(piperidin-1-yl)thiazolo[4,5-b]pyridin-6-yl)oxazole-4-carboxamide;
2-(2-hydroxypyridin-3-yl)-N-(2-morpholino-5-(piperidin-1-yl)thiazolo[4,5-b]pyridin-6-yl)oxazole-4-carboxamide;
N-(2,5-di(piperidin-1-yl)thiazolo[4,5-b]pyridin-6-yl)-2-(2-methoxypyridin-4-yl)oxazole-4-carboxamide;
2-(6-methoxypyridin-3-yl)-N-(2-morpholino-5-(piperidin-1-yl)thiazolo[4,5-b]pyridin-6-yl)oxazole-4-carboxamide;
2-(2-methoxypyridin-4-yl)-N-(2-morpholino-5-(piperidin-1-yl)thiazolo[4,5-b]pyridin-6-yl)oxazole-4-carboxamide;
(S)-N-(5-(3-fluoropiperidin-1-yl)-2-morpholinothiazolo[4,5-b]pyridin-6-yl)-2-(2-methylpyridin-4-yl)oxazole-4-carboxamide;
2-(6-methylpyridin-3-yl)-N-(2-morpholino-5-(piperidin-1-yl)thiazolo[4,5-b]pyridin-6-yl)oxazole-4-carboxamide;
2-(3-methylpyridin-4-yl)-N-(2-morpholino-5-(piperidin-1-yl)thiazolo[4,5-b]pyridin-6-yl)oxazole-4-carboxamide;
(S)-6-(3-aminopyrrolidin-1-yl)-N-(2-morpholino-5-(piperidin-1-yl)thiazolo[4,5-b]pyridin-6-yl)picolinamide;
(S)-6-(3-hydroxypyrrolidin-1-yl)-N-(2-morpholino-5-(piperidin-1-yl)thiazolo[4,5-b]pyridin-6-yl)picolinamide;
(S)-6-(3-aminopyrrolidin-1-yl)-N-(2,5-di(piperidin-1-yl)thiazolo[4,5-b]pyridin-6-yl)picolinamide;
(S)-N-(2,5-di(piperidin-1-yl)thiazolo[4,5-b]pyridin-6-yl)-6-(3-hydroxypyrrolidin-1-yl)picolinamide;
(S)-2-(3-aminopyrrolidin-1-yl)-N-(2-morpholino-5-(piperidin-1-yl)thiazolo[4,5-b]pyridin-6-yl)oxazole-4-carboxamide;
(S)-N-(5-(3-aminopyrrolidin-1-yl)-2-morpholinothiazolo[4,5-b]pyridin-6-yl)-2-(2-methylpyridin-4-yl)oxazole-4-carboxamide;
(S)-2-(3-aminopyrrolidin-1-yl)-N-(5-cyclopropyl-2-morpholinothiazolo[4,5-b]pyridin-6-yl)oxazole-4-carboxamide;
N-(5-cyclopropyl-2-morpholinothiazolo[4,5-b]pyridin-6-yl)-2-(2-methylpyridin-4-yl)oxazole-4-carboxamide;
(S)-2-(3-hydroxypyrrolidin-1-yl)-N-(2-morpholino-5-(piperidin-1-yl)thiazolo[4,5-b]pyridin-6-yl)oxazole-4-carboxamide;
(S)-N-(5-(3-hydroxypyrrolidin-1-yl)-2-morpholinothiazolo[4,5-b]pyridin-6-yl)-2-(2-methylpyridin-4-yl)oxazole-4-carboxamide;
(S)-N-(5-cyclopropyl-2-morpholinothiazolo[4,5-b]pyridin-6-yl)-6-(3-hydroxypyrrolidin-1-yl)picolinamide;
(S)-N-(5-cyclopropyl-2-morpholinothiazolo[4,5-b]pyridin-6-yl)-2-(3-hydroxypyrrolidin-1-yl)oxazole-4-carboxamide;
(S)-N-(5-cyclopropyl-2-morpholinothiazolo[4,5-b]pyridin-6-yl)-6-(1-(2-hydroxypropyl)-1H-pyrazol-4-yl)picolinamide;
(S)-N-(5-cyclopropyl-2-morpholinothiazolo[4,5-b]pyridin-6-yl)-2-(1-(2-hydroxypropyl)-1H-pyrazol-4-yl)oxazole-4-carboxamide;
N-(5-(3-hydroxypyrrolidin-1-yl)-2-morpholinothiazolo[4,5-b]pyridin-6-yl)-2-(6-methoxypyridin-3-yl)oxazole-4-carboxamide;
(S)-N-(5-(3-hydroxypyrrolidin-1-yl)-2-morpholinothiazolo[4,5-b]pyridin-6-yl)-2-(6-methoxypyridin-3-yl)oxazole-4-carboxamide;
(R)-N-(5-(3-hydroxypyrrolidin-1-yl)-2-morpholinothiazolo[4,5-b]pyridin-6-yl)-2-(6-methoxypyridin-3-yl)oxazole-4-carboxamide;

-continued (S)-N-(5-(azetidin-1-yl)-2-morpholinothiazolo[4,5-b]pyridin-6-yl)-6-(3-hydroxypyrrolidin-1-yl)picolinamide;
N-(5-(3-hydroxyazetidin-1-yl)-2-morpholinothiazolo[4,5-b]pyridin-6-yl)-2-(2-methylpyridin-4-yl)oxazole-4-carboxamide;
(S)-N-(5-(3-hydroxypyrrolidin-1-yl)-2-morpholinothiazolo[4,5-b]pyridin-6-yl)-5-(2-methylpyridin-4-yl)thiophene-2-carboxamide;
(S)-N-(5-(3-hydroxypyrrolidin-1-yl)-2-morpholinothiazolo[4,5-b]pyridin-6-yl)-5-(2-methylpyridin-4-yl)furan-2-carboxamide;
(S)-N-(5-(3-hydroxypiperidin-1-yl)-2-morpholinothiazolo[4,5-b]pyridin-6-yl)-2-(2-methylpyridin-4-yl)oxazole-4-carboxamide;
N-(5-(4-hydroxypiperidin-1-yl)-2-morpholinothiazolo[4,5-b]pyridin-6-yl)-2-(2-methylpyridin-4-yl)oxazole-4-carboxamide;
(R)-N-(5-(3-hydroxypyrrolidin-1-yl)-2-morpholinothiazolo[4,5-b]pyridin-6-yl)-2-(2-methylpyridin-4-yl)oxazole-4-carboxamide;
N-(5-(4-hydroxypiperidin-1-yl)-2-morpholinothiazolo[4,5-b]pyridin-6-yl)-5-(2-methylpyridin-4-yl)furan-2-carboxamide;
N-(5-(azetidin-1-yl)-2-(piperidin-1-yl)thiazolo[4,5-b]pyridin-6-yl)-2-(2-methylpyridin-4-yl)oxazole-4-carboxamide;
2-(2-methylpyridin-4-yl)-N-(2-(piperidin-1-yl)-5-(pyrrolidin-1-yl)thiazolo[4,5-b]pyridin-6-yl)oxazole-4-carboxamide;
2-(2-methylpyridin-4-yl)-N-(2-morpholino-5-(pyrrolidin-1-yl)thiazolo[4,5-b]pyridin-6-yl)oxazole-4-carboxamide;
5-(2-methylpyridin-4-yl)-N-(2-morpholino-5-(piperidin-1-yl)thiazolo[4,5-b]pyridin-6-yl)furan-2-carboxamide;
N-(5-(azepan-1-yl)-2-morpholinothiazolo[4,5-b]pyridin-6-yl)-2-(2-methylpyridin-4-yl)oxazole-4-carboxamide;
2-(2-aminopyridin-4-yl)-N-(2-morpholino-5-(piperidin-1-yl)thiazolo[4,5-b]pyridin-6-yl)oxazole-4-carboxamide hydrochloride;
N-(5-(azetidin-1-yl)-2-morpholinothiazolo[4,5-b]pyridin-6-yl)-2-(2-methylpyridin-4-yl)oxazole-4-carboxamide;
(R)-N-(5-(3-hydroxypiperidin-1-yl)-2-morpholinothiazolo[4,5-b]pyridin-6-yl)-2-(2-methylpyridin-4-yl)oxazole-4-carboxamide;
(R)-N-(5-(3-hydroxypiperidin-1-yl)-2-morpholinothiazolo[4,5-b]pyridin-6-yl)-5-(2-methylpyridin-4-yl)furan-2-carboxamide;
(S)-6-(1-(2-hydroxypropyl)-1H-pyrazol-4-yl)-N-(2-morpholino-5-(piperidin-1-yl)thiazolo[4,5-b]pyridin-6-yl)picolinamide;
N-(5-(4-fluoropiperidin-1-yl)-2-morpholinothiazolo[4,5-b]pyridin-6-yl)-5-(2-methylpyridin-4-yl)furan-2-carboxamide;
N-(5-(4-fluoropiperidin-1-yl)-2-morpholinothiazolo[4,5-b]pyridin-6-yl)-2-(2-methylpyridin-4-yl)oxazole-4-carboxamide hydrochloride;
N-(5-(1-methyl-1H-pyrazol-4-yl)-2-morpholinothiazolo[4,5-b]pyridin-6-yl)-2-(2-methylpyridin-4-yl)oxazole-4-carboxamide;
N-(5-(3-fluorophenyl)-2-morpholinothiazolo[4,5-b]pyridin-6-yl)-2-(2-methylpyridin-4-yl)oxazole-4-carboxamide;
N-(5-(4-hydroxypiperidin-1-yl)-2-morpholinothiazolo[4,5-b]pyridin-6-yl)-5-(2-methylpyridin-4-yl)furan-2-carboxamide;
N-(5-(3-fluoropiperidin-1-yl)-2-morpholinothiazolo[4,5-b]pyridin-6-yl)-5-(2-methylpyridin-4-yl)furan-2-carboxamide;
(S)-N-(5-(3-hydroxypyrrolidin-1-yl)-2-morpholinooxazolo[4,5-b]pyridin-6-yl)-2-(6-methoxypyridin-3-yl)oxazole-4-carboxamide;
N-(5-(3-hydroxypyrrolidin-1-yl)-2-morpholinooxazolo[4,5-b]pyridin-6-yl)-2-(2-methylpyridin-4-yl)oxazole-4-carboxamide;
(R)-N-(5-(3-hydroxypyrrolidin-1-yl)-2-morpholinooxazolo[4,5-b]pyridin-6-yl)-2-(6-methoxypyridin-3-yl)oxazole-4-carboxamide;
N-(5-(3-hydroxypyrrolidin-1-yl)-2-morpholinooxazolo[4,5-b]pyridin-6-yl)-2-(6-methoxypyridin-3-yl)oxazole-4-carboxamide;
(S)-N-(5-(3-hydroxypyrrolidin-1-yl)-2-morpholinooxazolo[4,5-b]pyridin-6-yl)-5-(2-methylpyridin-4-yl)furan-2-carboxamide;
(S)-N-(5-(3-hydroxypyrrolidin-1-yl)-2-morpholinooxazolo[4,5-b]pyridin-6-yl)-5-(2-methylpyridin-4-yl)thiophene-2-carboxamide;
N-(5-(azetidin-1-yl)-2-(piperidin-1-yl)oxazolo[4,5-b]pyridin-6-yl)-2-(2-methylpyridin-4-yl)oxazole-4-carboxamide;
2-(2-methylpyridin-4-yl)-N-(2-(piperidin-1-yl)-5-(pyrrolidin-1-yl)oxazolo[4,5-b]pyridin-6-yl)oxazole-4-carboxamide;
5-(2-methylpyridin-4-yl)-N-(2-morpholino-5-(piperidin-1-yl)oxazolo[4,5-b]pyridin-6-yl)furan-2-carboxamide;
N-(5-(azetidin-1-yl)-2-morpholinooxazolo[4,5-b]pyridin-6-yl)-2-(2-methylpyridin-4-yl)oxazole-4-carboxamide;
2-(2-methylpyridin-4-yl)-N-(2-morpholino-5-(pyrrolidin-1-yl)oxazolo[4,5-b]pyridin-6-yl)oxazole-4-carboxamide;
N-(5-(4-hydroxypiperidin-1-yl)-2-morpholinooxazolo[4,5-b]pyridin-6-yl)-5-(2-methylpyridin-4-yl)furan-2-carboxamide;
(R)-N-(5-(3-hydroxypiperidin-1-yl)-2-morpholinooxazolo[4,5-b]pyridin-6-yl)-5-(2-methylpyridin-4-yl)furan-2-carboxamide;
N-(5-(furan-3-yl)-2-morpholinooxazolo[4,5-b]pyridin-6-yl)-2-(2-methylpyridin-4-yl)oxazole-4-carboxamide;
N-(5-(3-fluoropiperidin-1-yl)-2-morpholinooxazolo[4,5-b]pyridin-6-yl)-2-(2-methylpyridin-4-yl)oxazole-4-carboxamide;

-continued

N-(5-(4-hydroxypiperidin-1-yl)-2-morpholinooxazolo[4,5-b]pyridin-6-yl)-2-(2-methylpyridin-4-yl)oxazole-4-carboxamide;
N-(5-(4-fluoropiperidin-1-yl)-2-morpholinooxazolo[4,5-b]pyridin-6-yl)-2-(2-methylpyridin-4-yl)oxazole-4-carboxamide;
(S)-N-(5-(3-aminopiperidin-1-yl)-2-morpholinothiazolo[4,5-b]pyridin-6-yl)-2-(2-methylpyridin-4-yl)oxazole-4-carboxamide;
2-(2-methylpyridin-4-yl)-N-(2-morpholino-5-(1H-pyrazol-4-yl)thiazolo[4,5-b]pyridin-6-yl)oxazole-4-carboxamide;
N-(5-(6-fluoropyridin-3-yl)-2-morpholinothiazolo[4,5-b]pyridin-6-yl)-2-(2-methylpyridin-4-yl)oxazole-4-carboxamide;
N-(5-(3-hydroxy-8-azabicyclo[3.2.1]octan-8-yl)-2-morpholinothiazolo[4,5-b]pyridin-6-yl)-2-(2-methylpyridin-4-yl)oxazole-4-carboxamide;
N-(2-(3-hydroxypiperidin-1-yl)-5-(piperidin-1-yl)thiazolo[4,5-b]pyridin-6-yl)-2-(2-methylpyridin-4-yl)oxazole-4-carboxamide;
2-(2-acetamidopyridin-4-yl)-N-(5-(4-hydroxypiperidin-1-yl)-2-morpholinothiazolo[4,5-b]pyridin-6-yl)oxazole-4-carboxamide;
N-(2-(3-hydroxypiperidin-1-yl)-5-(4-hydroxypiperidin-1-yl)thiazolo[4,5-b]pyridin-6-yl)-2-(2-methylpyridin-4-yl)oxazole-4-carboxamide;
2-(2-acetamidopyridin-4-yl)-N-(5-(3-hydroxypiperidin-1-yl)-2-morpholinothiazolo[4,5-b]pyridin-6-yl)oxazole-4-carboxamide;
2-(2-aminopyridin-4-yl)-N-(5-(3-hydroxypiperidin-1-yl)-2-morpholinothiazolo[4,5-b]pyridin-6-yl)oxazole-4-carboxamide hydrochloride;
5-(2-aminopyridin-4-yl)-N-(5-(4-hydroxypiperidin-1-yl)-2-morpholinothiazolo[4,5-b]pyridin-6-yl)furan-3-carboxamide hydrochloride;
2-(2-aminopyridin-4-yl)-N-(5-(4-hydroxypiperidin-1-yl)-2-morpholinothiazolo[4,5-b]pyridin-6-yl)oxazole-4-carboxamide hydrochloride;
2-(2-aminopyridin-4-yl)-N-(5-(4-fluoropiperidin-1-yl)-2-morpholinothiazolo[4,5-b]pyridin-6-yl)oxazole-4-carboxamide hydrochloride;
N-(5-(2-fluoropyridin-4-yl)-2-morpholinothiazolo[4,5-b]pyridin-6-yl)-2-(2-methylpyridin-4-yl)oxazole-4-carboxamide;
N-(5-(4-fluoropiperidin-1-yl)-2-(3-hydroxypiperidin-1-yl)thiazolo[4,5-b]pyridin-6-yl)-2-(2-methylpyridin-4-yl)oxazole-4-carboxamide;
N-(5-(4-aminopiperidin-1-yl)-2-(3-hydroxypiperidin-1-yl)thiazolo[4,5-b]pyridin-6-yl)-2-(2-methylpyridin-4-yl)oxazole-4-carboxamide hydrochloride; and
N-(5-(2-hydroxypyridin-4-yl)-2-morpholinothiazolo[4,5-b]pyridin-6-yl)-2-(2-methylpyridin-4-yl)oxazole-4-carboxamide hydrochloride;

or a pharmaceutically acceptable salt or a stereoisomer thereof.

24. The method of claim 1, wherein the nucleoside analog is azacitidine, decitabine, cytarabine, gemcitabine, 5'-deoxy-5-fluorouridine, fludarabine, cladribine, troxacitabine, or clofarabine.

25. The method of claim 1, wherein the cancer is a hematological malignancy.

26. The method of claim 25, wherein the hematological malignancy is a non-Hodgkin's lymphoma.

27. The method of claim 25, wherein the hematological malignancy is a leukemia or lymphoma.

28. The method of claim 25, wherein the is hematological malignancy is myelogenous leukemia, myeloid leukemia, myelodysplastic syndrome, lymphoblastic leukemia, chronic lymphocytic leukemia (CLL), small lymphocytic lymphoma (SLL), high risk CLL, follicular lymphoma, diffuse large B-cell lymphoma (DLBCL), mantle cell lymphoma (MCL), Waldenstrom's macroglobulinemia (WM), multiple myeloma, marginal zone lymphoma (MZL), Burkitt's lymphoma, non-Burkitt high grade B cell lymphoma, extranodal marginal zone B cell lymphoma, transformed high grade B-cell lymphoma (HGBL), lymphoplasmacytic lymphoma (LPL), central nervous system lymphoma (CNSL), or MALT lymphoma.

29. The method of claim 25, wherein the hematological malignancy is relapsed or refractory.

30. The method of claim 1, wherein the BCL-2 inhibitor is venetoclax.

* * * * *